(12) United States Patent
Chong

(10) Patent No.: US 10,441,669 B2
(45) Date of Patent: Oct. 15, 2019

(54) MULTIFUNCTIONAL CHELATORS, COMPLEXES, AND COMPOSITIONS THEREOF, AND METHODS OF USING SAME

(71) Applicant: ILLINOIS INSTITUTE OF TECHNOLOGY, Chicago, IL (US)

(72) Inventor: Hyun-Soon Chong, Chicago, IL (US)

(73) Assignee: ILLINOIS INSTITUTE OF TECHNOLOGY, Chicago, IL (US)

( * ) Notice: Subject to any disclaimer, the term of this patent is extended or adjusted under 35 U.S.C. 154(b) by 364 days.

(21) Appl. No.: 15/027,104

(22) PCT Filed: Oct. 6, 2014

(86) PCT No.: PCT/US2014/059276
§ 371 (c)(1),
(2) Date: Apr. 4, 2016

(87) PCT Pub. No.: WO2015/051362
PCT Pub. Date: Apr. 9, 2015

(65) Prior Publication Data
US 2016/0235870 A1    Aug. 18, 2016

Related U.S. Application Data

(60) Provisional application No. 61/886,992, filed on Oct. 4, 2013.

(51) Int. Cl.
| | | |
|---|---|---|
| A61K 51/00 | (2006.01) | |
| A61M 36/14 | (2006.01) | |
| A61K 51/04 | (2006.01) | |
| C07D 401/12 | (2006.01) | |
| C07D 255/02 | (2006.01) | |
| C07D 257/02 | (2006.01) | |

(52) U.S. Cl.
CPC ........ *A61K 51/0482* (2013.01); *C07D 255/02* (2013.01); *C07D 257/02* (2013.01); *C07D 401/12* (2013.01); *A61K 51/0474* (2013.01)

(58) Field of Classification Search
None
See application file for complete search history.

(56) References Cited

U.S. PATENT DOCUMENTS

| | | | |
|---|---|---|---|
| 4,831,175 A | 5/1989 | Gansow et al. | |
| 5,554,749 A | 9/1996 | Wallace et al. | |
| 5,847,216 A | 12/1998 | Ott-Dembrowski et al. | |
| 6,207,858 B1 | 3/2001 | Chinn et al. | |
| 6,252,076 B1 | 6/2001 | Hong et al. | |
| 6,875,866 B2 | 4/2005 | Dahanukar et al. | |
| 7,081,452 B2 | 7/2006 | Brechbiel et al. | |
| 7,163,935 B2 | 1/2007 | Brechbiel et al. | |
| 7,354,568 B1 | 4/2008 | Meade et al. | |
| 7,368,100 B2 | 5/2008 | Brechbiel et al. | |
| 7,563,433 B2 | 7/2009 | McBride et al. | |
| 7,597,876 B2 | 10/2009 | McBride et al. | |
| 7,799,934 B2 | 9/2010 | Antilla et al. | |
| 7,993,626 B2 | 8/2011 | McBride et al. | |
| 8,153,101 B2 | 4/2012 | McBride et al. | |
| 9,115,094 B2 | 8/2015 | Chong | |
| 9,446,995 B2 | 9/2016 | Chong | |
| 2003/0108486 A1 | 6/2003 | Platzek et al. | |
| 2009/0155166 A1 | 6/2009 | McBride et al. | |
| 2009/0162290 A1 | 6/2009 | Benes et al. | |
| 2010/0322855 A1* | 12/2010 | Chong | C07D 255/02 424/1.65 |
| 2011/0110854 A1 | 5/2011 | McBride et al. | |
| 2016/0052894 A1 | 2/2016 | Chong | |

FOREIGN PATENT DOCUMENTS

| | | |
|---|---|---|
| CN | 102743770 A | 10/2012 |
| DE | 36 25 417 C2 | 10/1998 |
| DE | 198 49 465 A1 | 4/2000 |
| EP | 0628316 | 6/1993 |
| WO | WO 01/52898 | 7/2001 |

OTHER PUBLICATIONS

Wainwright, K.P. Coord. Chem. Rev. 1997, 166, 35-90.*
Rizzo, F. et al., "Synthesis of 8-hydroxyquinoline functionalised DO3A ligand and Eu(III) and Er(III) complexes: Luminescence properties," Synthetic Metals, Mar. 2009, 159, pp. 356-360.
Chong, H., "A novel cholic acid-based contrast enhancement agent for targeted MRI," Bioorganic & Medicinal Chemistry Letters, Jan. 18, 2008, pp. 2505-2508.
Birch, N. et al., "Expert Opinion-Iron chelators as therapeutic iron depletion agents," Expert Opin. Ther. Patents, 2006, vol. 16, No. 11, pp. 1533-1556.
Chong, H., et al., "Synthesis and Evaluation of Novel Polyaminocarboxylate-Based Antitumor Agents," J. Med. Chem., Mar. 2008, 51 (7), pp. 2208-2215.
Chong, H., et al., "Novel synthetic ligands for targeted PET imaging and radiotherapy of copper," Bio. & Med. Chem. Letters, Sep. 2007, vol. 17, No. 22, pp. 6107-6110.

* cited by examiner

*Primary Examiner* — Michael G. Hartley
*Assistant Examiner* — Melissa J Perreira
(74) *Attorney, Agent, or Firm* — Pauley Erickson & Kottis

(57) ABSTRACT

Multifunctional chelators, metal complexes thereof, compositions thereof, and methods of making and use in diagnostic imaging and treatment of cellular disorders.

25 Claims, 13 Drawing Sheets

MULTIFUNCTIONAL CHELATORS, COMPLEXES, AND COMPOSITIONS THEREOF, AND METHODS OF USING SAME

CROSS REFERENCE TO RELATED APPLICATION

This patent application is a National Stage entry of PCT Patent Application PCT/US2014/059276, filed on 6 Oct. 2014, which claims priority to, and the benefit of, U.S. Provisional. Patent Application Ser. No. 61/886,992, filed on 4 Oct. 2013. The co-pending PCT Patent Application is hereby incorporated by reference herein in its entirety and is made a part hereof, including but not limited to those portions which specifically appear hereinafter.

GOVERNMENT SUPPORT CLAUSE

This research was supported by the National Institutes of Health (Grant Numbers NIH2RO1CA112503 and NIHRO1CA136695). The U.S. government has certain rights in this invention.

BACKGROUND OF THE INVENTION

Macrocyclic and acyclic chelating agents have been employed for biomedical, environmental, and radiopharmaceutical applications such as magnetic resonance (MR) and positron emission tomography (PET) imaging and iron chelation therapy (ICT) and antibody targeted radiation therapy (Radioimmunotherapy, RIT) of cancer and nuclear remediation. Research efforts have been directed towards development of effective metal binding chelating agents, a critical component for such applications.

RIT holds great promise for treatment of many diseases including cancers, evidenced by Zevalin® (1B4M-DTPA) therapy. However, active clinical exploration of RIT using a variety of antibodies and cytotoxic radionuclides has been challenged by the absence of adequate bifunctional ligands that can bind the radionuclides with clinically acceptable kinetics and in vivo stability. The currently available bifunctional ligands, C-DOTA and C-DTPA analogues have limitations such as slow kinetics and low complex stability in vivo.

A sensitive diagnostic modality, positron emission tomography (PET) has been demonstrated to give highly sensitive detection and staging of various cancers. PET is known to provide imaging of solid tumors with better sensitivity, resolution, and quantification as compared to gamma ray and SPECT. Although various antibody or peptide conjugates based on TETA, DOTA, or CB-TE2TA radiolabeled with a radioactive metal have been explored for PET imaging of solid tumors in the preclinical settings, the currently available metal binding chelators do not present optimal chelation chemistry with the metals. Development of bifunctional ligand to rapidly and stably bind a radionuclide will allow for targeted and highly sensitive PET imaging of cancers.

MRI, a non-invasive and high resolution imaging technique has become a powerful cancer diagnostic technique. The paramagnetic Gd(II) complexes available in the clinic including DOTA and DTPA are the first generation of clinically approved MR contrast agents. However, Gd(DTPA) and Gd(DOTA) are non-specific contrast agents with extracellular distribution and have the disadvantages of low relaxivity, low tissue specificity, and rapid clearance. The contrast agents with high relaxitivty and tissue-specificity are required for sensitive MRI to the targeted tissues. Considerable research efforts have been made to develop contrast agents with high target-specificity and relaxivity.

Internal contamination with radionuclides that can occur during a nuclear accident or attack can lead to life-threatening diseases, and the radiocontaminants present in the human body must be rapidly and safely eliminated. Research efforts have been made to develop chelators as decorporation agents that can efficiently remove radionuclides from the body. Two metal complexes of diethylenetriaminepentaacetic acid (DTPA), Ca(II)-DTPA and Zn(II)-DTPA are clinically available as decorporation agents of diverse radioactinides including $^{241}$Am, $^{252}$Cf, $^{141}$Ce, and $^{144}$Ce, $^{238}$Pu, $^{239}$Pu, and $^{244}$Cm. DTPA is known to display rapid complexation kinetics with a wide range of radioactive metals. However, low binding selectivity, zinc stripping, poor kinetic stability, and poor aqueous solubility of DTPA limits its practical use for biomedical applications.

Development of better drugs for targeted therapy and imaging of cancers is a critical need. Multifunctional nanomedicines as theranostic drugs and dual modality diagnostics are expected to provide targeted therapy and sensitive imaging of the cancers. Although multifunctional theranostic and dual imaging technology is available in the clinic, less progress has been made on development of multifunctional chelators that can tightly and rapidly hold biologically important metals. There is thus a continuing need for improved chelators and multifunctional ligands, such as for use as discussed above.

SUMMARY OF THE INVENTION

The invention provides new chelating agents and multifunctional ligands for biomedical and/or environmental applications. The chelators of this invention provide enhanced complexation kinetics and stability in human serum compared to clinically available chelators of DOTA and DTPA analogues. The chelators display cytotoxic activity against cancer cells without removing Zn(II). One of the problems with the currently available drug, DTPA is removal of Zn(II) in vivo. The chelators have great promise for use in broad applications of radiotherapy and decorporation of radinuclides and iron chelation therapy, and imaging, such as, without limitation, magnetic resonance imaging (MRI), fluorescence imaging, positron emission tomography (PET). The multifunctional ligands can rapidly form a stable complex with a biologically important metal and are critical components for successful applications of targeted dual imaging and theranostic technology in medicine and nuclear remediation.

The present invention provides a compound of formula (I):

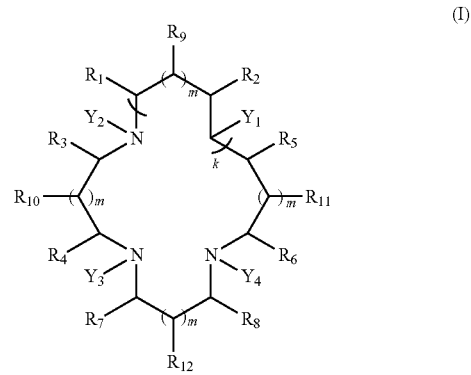

where k is 0 or 1; m is 0 or 1; each of $Y_1$-$Y_4$ independently is one of a structure of formula (a-1), (a-2), or (a-3):

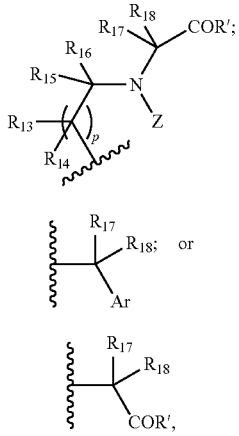

where p is 1 or 2; Z is hydrogen, formula (a-2), formula (a-3), Ar, a pyridylalkyl, a protecting group, an aryl containing group, an alkynyl containing group, an amine containing group, an azide containing group, or an amide containing group; Ar is or includes an aromatic ring or a heteroaromatic ring; and each R' independently is OH, $NH_2$, OR", $NR_2$" wherein each R" is one of alkyl, tert-butyl, allyl, benzyl, or a protecting group; and wherein each of $R_{1-18}$ independently is or includes hydrogen, carboxyalkyl, alkylamido, alkyl, allyl, benzyl, benzyloxyalkyl, cycloalkyl, alkoxy, hydroxyalkyl, aryl, aryloxy, hydroxyaryl, heteroaryl, phenyl, vinyl, alkynyl, alkenyl, furannylalkyl, alkylthioalkyl, arylhydroxyalkyl, indanyl, inolylalkyl, naphthylalkyl, imidazolylalkyl, pyridiylalkyl, benzothiophenylalkyl, thiophenylalkyl, thioalkyl, thioaryl, thiobenzyl, hydroxy, an alkynyl containing group, substituted carbonyl, hydroxyalkyl, triazolylalkyl, aminoalkyl, benzothiophenylalkyl, carboxyl, carboxyalkyloxy, amine, a protected amine, carboxylic acid, holoalkylamido, aldehyde, ester, amido, tosyl, phthalimidyl, maleimidyl, trityl, tert-butyloxycarbonyl, carbobenzyloxy, o-nosyl, acetyl, fluoroacetyl, dimethoxybenzyl, p-methoxybenzyl, an amide containing group, a thioamide containing group, an amino acid-containing group, an ester containing group, a protecting group, an amine protecting group, or:

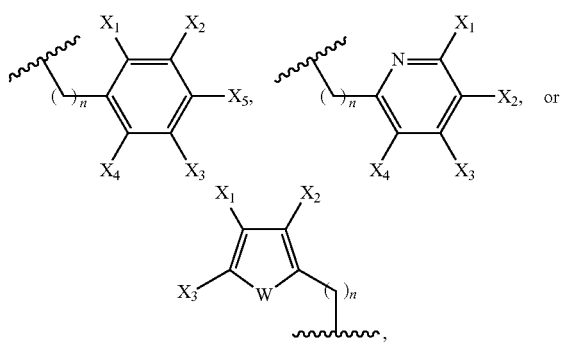

where W is NH, oxygen, or sulfur, n is 1-5, and each of $X_1$-$X_5$ independently is or includes hydrogen, halo, cyano, alkyl, hydroxy, nitro, amino, alkylamino, thiocyano, isothiocyano, alkoxy, aryloxy, carboxyl, carboxyalkyl, carboxyalkyloxy, ester, amido, aldehydo, alkylamido, holoalkylamido, an ester containing group, an carbonyl containing group, an amide containing group, an amine containing group, a thioamide containing group, an alkynyl containing group, or an amino acid-containing group. Embodiments of this invention include compounds where k is 1 and/or m is 0.

In one embodiment of this invention, more than one of $Y_1$-$Y_4$ includes formula (a-1). In some embodiments, at least three of $Y_1$-$Y_4$ or all four of $Y_1$-$Y_4$, includes formula (a-1). Two or more Z groups within formula (a-1) within formula (I) can be the same or different, and can desirably be selected from hydrogen, formula (a-2), formula (a-3), Ar, a pyridylalkyl, a protecting group, an aryl containing group, an alkynyl containing group, an amine containing group, an azide containing group, or an amide containing group; Ar is or includes an aromatic ring or a heteroaromatic ring; and each R' independently is OH, $NH_2$, OR", $NR_2$" wherein each R" is one of alkyl, tert-butyl, allyl, benzyl, or a protecting group.

In embodiment of this invention, Ar is selected from:

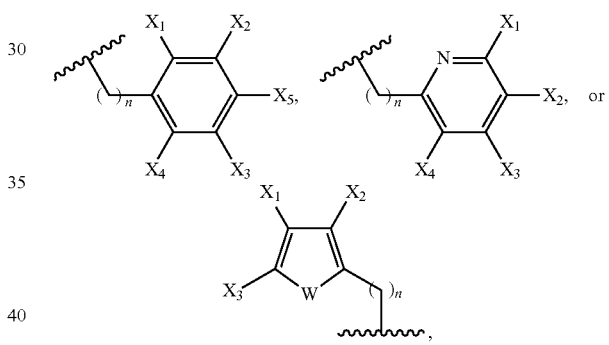

where W is NH, oxygen, or sulfur, n is 1-5, and each of $X_1$-$X_5$ independently is or includes hydrogen, halo, cyano, alkyl, hydroxy, nitro, amino, alkylamino, thiocyano, isothiocyano, alkoxy, aryloxy, carboxyl, carboxyalkyl, carboxyalkyloxy, ester, amido, aldehydo, alkylamido, holoalkylamido, an ester containing group, an carbonyl containing group, an amide containing group, an amine containing group, a thioamide containing group, an alkynyl containing group, or an amino acid-containing group. Additionally, one of $R_{13}$-$R_{18}$ can be:

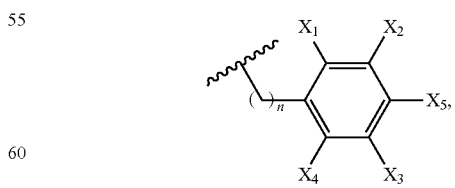

where n is 1-5. In one preferred embodiment, $X_5$ of the above ring structures comprises $NO_2$.

In one embodiment of this invention, at least one of $Y_1$-$Y_4$ is selected from:

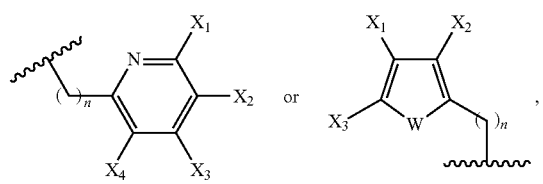

where W is NH, oxygen, or sulfur and n is 1-5. Exemplary herteroaryl substituents for at least one of $Y_1$-$Y_4$ include:

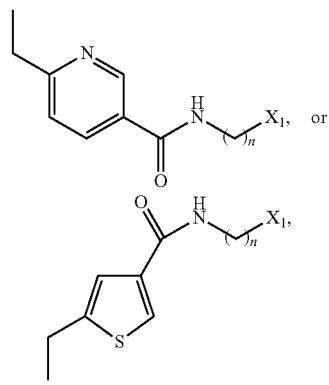

where $X_1$ is as described above or is $NH_2$, NHBoc, NCS or NHPhth. In one embodiment, an other of $Y_1$-$Y_4$ is formula (a-3) with one of $R_{17-18}$ being:

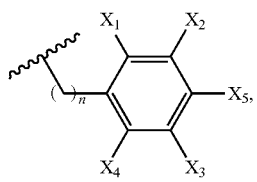

where n is 1-5.

In another embodiment of this invention, at least one of $Y_1$-$Y_4$ is formula (a-1), and Z is selected from:

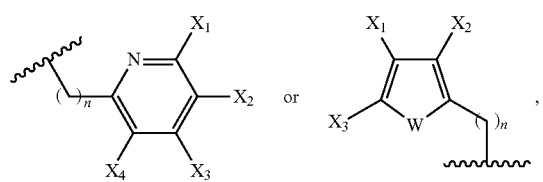

where W is NH, oxygen, or sulfur and n is 1-5. Exemplary herteroaryl substituents for at least one of $Y_1$-$Y_4$ include:

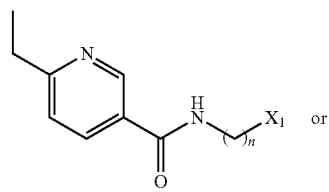

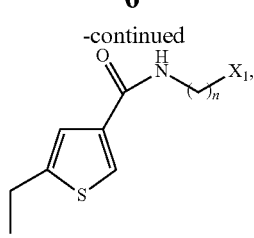

where $X_1$ is as described above or is $NH_2$, NHBoc, NCS or NHPhth. In one embodiment, an other of $Y_1$-$Y_4$ is formula (a-3) with one of $R_{17-18}$ being:

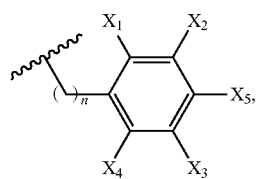

where n is 1-5.

The present invention further provides a compound of formula (III):

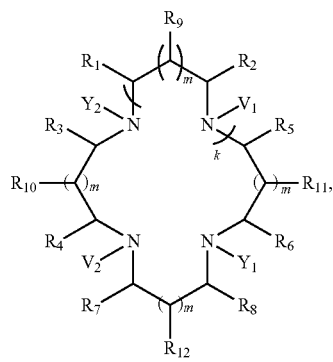

where k is 0 or 1; m is 0 or 1; each of $V_1$-$V_2$ independently is one of the following:

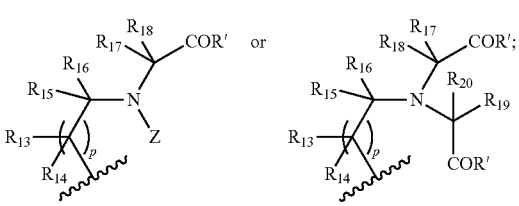

and each of $Y_1$-$Y_2$ independently is one of the following:

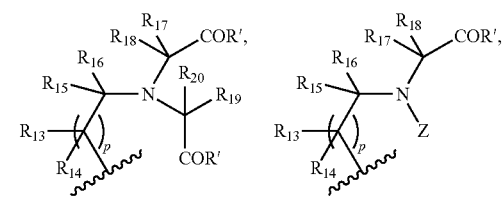

-continued

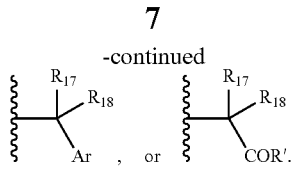

Still further provided is a complex comprising the compound of formula (I), or (II) and a metal ion, such as Ac, Al, Bi, Pb, Y, Mn, Cr, Fe, Co, Zn, Ni, Tc, Gd, In, Ga, Cu, Re, Sm, Pm, Ho, Zr, a lanthanide, and an actinide, or a radioactive isotope of the metal ions, or of carbon, nitrogen, iodine, fluorine, oxygen, or helium.

The invention also provides a conjugate comprising any of the above compounds or complexes and a biomolecule or a targeting moiety, preferably substituted for or at X in the above formulas. Exemplary biomolecules include hormones, bile acids, amino acids, peptides, peptidomimetics, proteins, deoxyribonucleic acids (DNA), ribonucleic acids (RNA), lipids, albumin, receptor molecules, receptor binding molecules, hapten, monoclonal antibodies, polyclonal antibodies, peptides, aptamers, folic acid, estrogens, or transferring.

A pharmaceutical composition comprising a pharmaceutically acceptable carrier and one or more of the above compounds, complexes, or conjugates thereof is also provided.

A method for obtaining a diagnostic image of a host is further provided. The method comprises administering to the host a compound, complex, or conjugate of formula (I) or (II), in an amount effective to provide an image; and exposing the host to an energy source, whereupon a diagnostic image of the host is obtained.

Still further provided is a method for treating a cellular disorder in a mammal. The method comprises administering to the mammal a compound, conjugate, or complex of formula (I) or (II), in an amount effective to treat the cellular disorder, whereupon the cellular disorder in the mammal is treated.

The invention also provides methods of preparing the compounds of formula (I) or (II).

Other objects and advantages will be apparent to those skilled in the art from the following detailed description taken in conjunction with the appended claims and drawings.

DETAILED DESCRIPTION OF PREFERRED EMBODIMENTS

Figure 1:
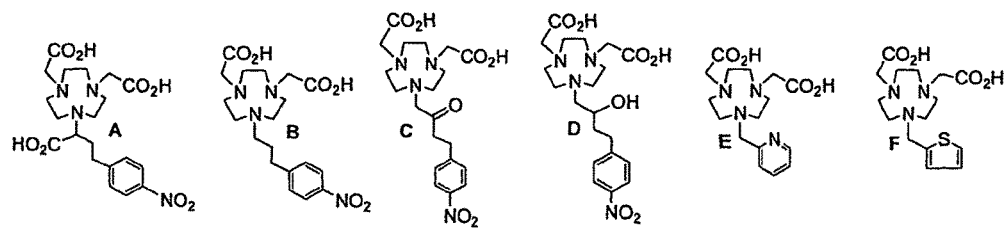
FIG. 1 illustrates backbones of chelators, such as are useful for PET imaging using $^{64}$Cu, according to one embodiment of this invention.

The present invention provides a compound of formula (I):

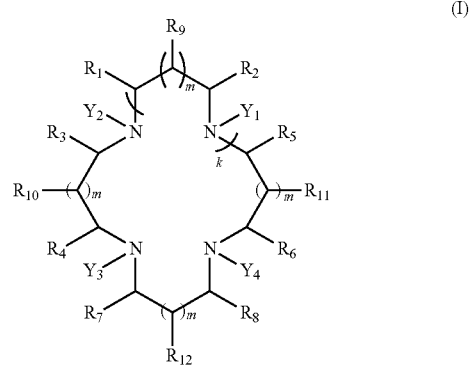

where k is 0 or 1; m is 0 or 1; each of $Y_1$-$Y_4$ independently is one of a structure of formula (a-1), (a-2), or (a-3):

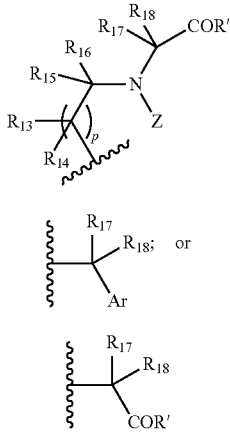

(a-1)

(a-2)

(a-3)

where p is 1 or 2; Z is hydrogen, formula (a-2), formula (a-3), Ar, a pyridylalkyl, a protecting group, an aryl containing group, an alkynyl containing group, an amine containing group, an azide containing group, or an amide containing group; Ar is or includes an aromatic ring or a heteroaromatic ring; and each R' independently is OH, $NH_2$, OR", $NR_2$" wherein each R" is one of alkyl, tert-butyl, allyl, benzyl, or a protecting group; and wherein each of $R_{1-18}$ independently is or includes hydrogen, carboxyalkyl, alkylamido, alkyl, allyl, benzyl, benzyloxyalkyl, cycloalkyl, alkoxy, hydroxyalkyl, aryl, aryloxy, hydroxyaryl, heteroaryl, phenyl, vinyl, alkynyl, alkenyl, furannylalkyl, alkylthioalkyl, arylhydroxyalkyl, indanyl, inolylalkyl, naphthylalkyl, imidazolylalkyl, pyridiylalkyl, benzothiophenylalkyl, thiophenylalkyl, thioalkyl, thioaryl, thiobenzyl, hydroxy, an alkynyl containing group, substituted carbonyl, hydroxyalkyl, triazolylalkyl, aminoalkyl, benzothiophenylalkyl, carboxyl, carboxyalkyloxy, amine, a protected amine, carboxylic acid, holoalkylamido, aldehyde, ester, amido, tosyl, phthalimidyl, maleimidyl, trityl, tert-butyloxycarbonyl, carbobenzyloxy, o-nosyl, acetyl, fluoroacetyl, dimethoxybenzyl, p-methoxybenzyl, an amide containing group, a thioamide containing group, an amino acid-containing group, an ester containing group, a protecting group, an amine protecting group or:

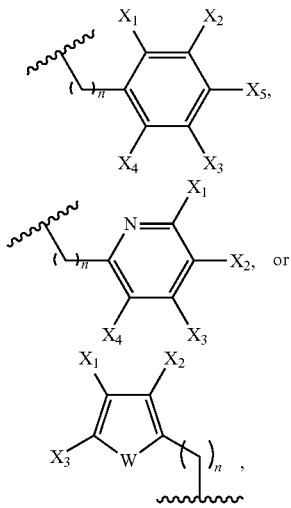

where W is NH, oxygen, or sulfur, n is 1-5, and each of $X_1$-$X_5$ independently is or includes hydrogen, halo, cyano, alkyl, hydroxy, nitro, amino, alkylamino, thiocyano, isothiocyano, alkoxy, aryloxy, carboxyl, carboxyalkyl, carboxyalkyloxy, ester, amido, aldehydo, alkylamido, holoalkylamido, an ester containing group, an carbonyl containing group, an amide containing group, an amine containing group, a thioamide containing group, an alkynyl containing group, or an amino acid-containing group. Embodiments of this invention include compounds where k is 1 and/or m is 0.

In embodiments of this invention, more than one of $Y_1$-$Y_4$ includes of formula (a-1). In some embodiments, at least three of $Y_1$-$Y_4$ or all four of $Y_1$-$Y_4$, includes a same or different variation of formula (a-1). Each Z within formula (a-1) of the one to four of $Y_1$-$Y_4$ can be the same or different, and is selected from hydrogen, formula (a-2), formula (a-3), Ar, a pyridylalkyl, a protecting group, an aryl containing group, an alkynyl containing group, an amine containing group, an azide containing group, or an amide containing group, where Ar is or includes an aromatic ring or a heteroaromatic ring, and each R' independently is OH, $NH_2$, OR", $NR_2$", wherein each R" is one of alkyl, tert-butyl, allyl, benzyl, or a protecting group. Additionally, one of $R_{13}$-$R_{18}$ of one or more of formula (a-1) can be:

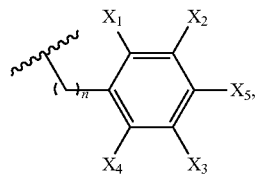

where n is 1-5. In one preferred embodiment, $X_5$ of the above ring structures comprises $NO_2$.

In embodiment of this invention, Ar is selected from:

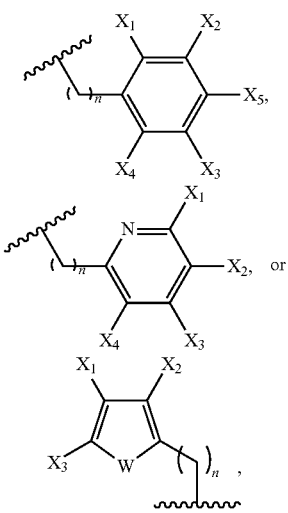

where W is NH, oxygen, or sulfur, n is 1-5, and each of $X_1$-$X_5$ independently is or includes hydrogen, halo, cyano, alkyl, hydroxy, nitro, amino, alkylamino, thiocyano, isothiocyano, alkoxy, aryloxy, carboxyl, carboxyalkyl, carboxyalkyloxy, ester, amido, aldehydo, alkylamido, holoalkylamido, an ester containing group, an carbonyl containing group, an amide containing group, an amine containing group, a thioamide containing group, an alkynyl containing group, or an amino acid-containing group.

The present invention further provides a compound of formula (II):

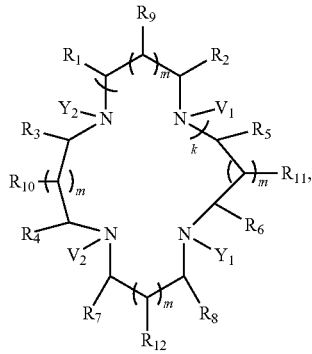

where k is 0 or 1; m is 0 or 1; each of $V_1$-$V_2$ independently is one of the following:

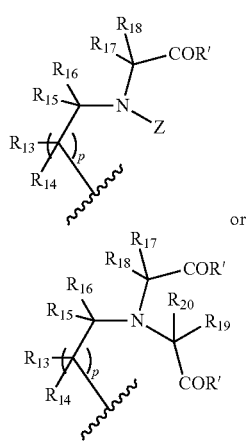

and each of $Y_1$-$Y_2$ independently is one of the following:

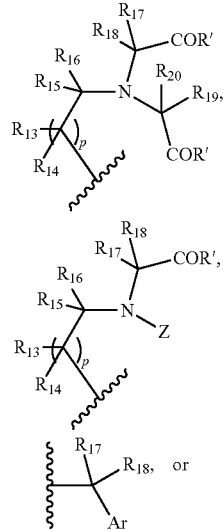

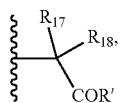

with possible substitutents as described above for formula (I).

In one embodiment of this invention, at least one of $Y_1$-$Y_4$ is Ar. Ar can be selected from:

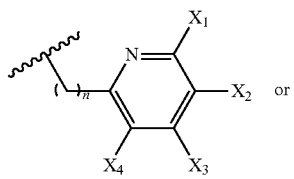

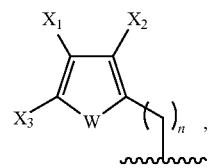

where W is NH, oxygen, or sulfur and n is 1-5. Exemplary herteroaryl substituents for at least one of $Y_1$-$Y_4$ include:

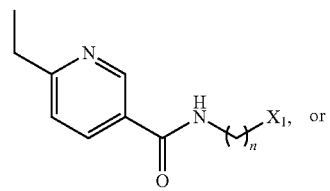

where $X_1$ is described above or comprises $NH_2$, NHBoc, NCS or NHPhth. In one further embodiment, an other of $Y_1$-$Y_4$ is formula (a-3) with one of $R_{17\text{-}18}$ being:

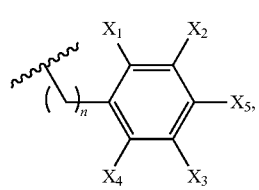

where n is 1-5.

In another embodiment of this invention, at least one of $Y_1$-$Y_4$ is formula (a-1), and Z is selected from:

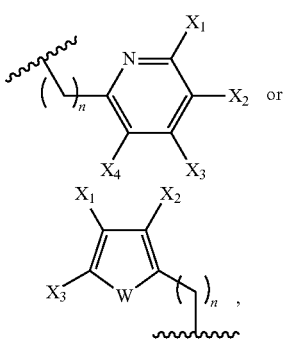

where W is NH, oxygen, or sulfur and n is 1-5. Exemplary herteroaryl substituents for at least one of $Y_1$-$Y_4$ include:

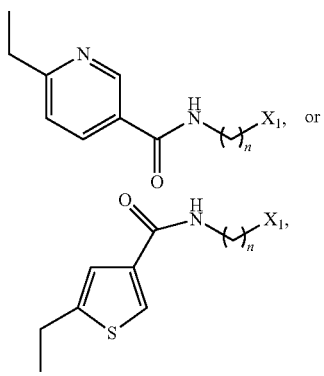

where $X_1$ is described above or comprises $NH_2$, NHBoc, NCS or NHPhth. In one further embodiment, an other of $Y_1$-$Y_4$ is formula (a-3) with one of $R_{17-18}$ being:

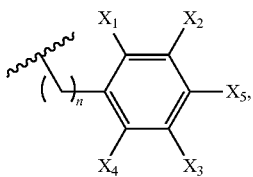

where n is 1-5.

Any of the groups indicated above for $R^{1-20}$ and/or X can optionally be substituted with suitable substituents such as hydroxy, $C_{1-12}$ alkoxy, acyloxy, halo, benzyl, acetyl, carboxyl, carboxy-$C_{1-12}$ alkyl, such as carboxymethyl, carboxyethyl, carboxy-$C_{1-12}$ alkylamido, carboxy-$C_{1-12}$ dialkylamido, carboxyamido, amino, $C_{1-12}$ alkylamino, $C_{1-12}$ dialkylamino, $C_{1-12}$ alkylcarbonyl, $C_{6-30}$ arylamino, $C_{6-30}$ diarylamino, cyano, tolyl, xylyl, mesityl, anisyl, pyrrolidinyl, formyl, thio, $C_{1-12}$ alkylthio, $C_{6-30}$ aryl, $C_{5-30}$ heteroaryl, such as pyranyl, pyrrolyl, furanyl, thiophenyl, thiazolyl, pyrazolyl, pyridinyl, or pyrimidinyl, phenoxy, benzyloxy, phenylcarbonyl, benzylcarbonyl, nitrophenyl $C_{1-12}$ trialkylsilyl, nitro, sulfonyl, nitrobenzyl, $C_{1-12}$ trialkylammonium, $C_{1-12}$ alkyl, $C_{3-8}$ cycloalkyl, tetrahydrofuranyl, tetrahydropyranyl, piperidinyl and morpholinyl.

Referring now to terminology used generically herein, the term "alkyl" means a straight-chain or branched alkyl substituent containing from, for example, about 1 to about 12 carbon atoms, preferably from about 1 to about 8 carbon atoms, more preferably from about 1 to about 6 carbon atoms. Examples of such substituents include methyl, ethyl, propyl, isopropyl, n-butyl, sec-butyl, isobutyl, tert-butyl, pentyl, isoamyl, hexyl, octyl, dodecanyl, and the like.

The term "cycloalkyl," as used herein, means a cyclic alkyl substituent containing from, for example, about 3 to about 30 carbon atoms, preferably from about 5 to about 14 carbon atoms, more preferably from about 5 to about 10 carbon atoms, and most preferably from about 5 to about 7 carbon atoms. Examples of such substituents include cyclopropyl, cyclobutyl, cyclopentyl, cyclohexyl, and the like.

The term "halo" or "halogen," as used herein, means a substituent selected from Group VIIA, such as, for example, fluorine, bromine, chlorine, and iodine. Preferably, the halo is bromine or iodine.

The term "aryl" refers to an unsubstituted or substituted aromatic carbocyclic substituent, as commonly understood in the art, and includes monocyclic and polycyclic aromatics such as, for example, phenyl, biphenyl, toluenyl, anisolyl, naphthyl, anthracenyl and the like. An aryl substituent generally contains from, for example, about 3 to about 30 carbon atoms, preferably from about 6 to about 18 carbon atoms, more preferably from about 6 to about 14 carbon atoms and most preferably from about 6 to about 10 carbon atoms. It is understood that the term aryl applies to cyclic substituents that are planar and comprise 4n+2 π electrons, according to Hückel's Rule.

The term "heteroaryl" means a substituent defined by an aromatic heterocyclic ring, as is commonly understood in the art, including monocyclic and polycyclic heteroaryls containing from, for example, about 3 to about 30 carbon atoms, preferably from about 5 to about 10 carbon atoms, more preferably from about 5 to about 6 carbon atoms. Monocyclic heteroaryls include, for example, imidazolyl, thiazolyl, pyrazolyl, pyrrolyl, furanyl, pyrazolinyl, thiophenyl, oxazolyl, isoxazolyl, pyridinyl, pyridonyl, pyrimidinyl, pyrazinyl, and triazinyl substituents. Polycyclic heteroaryls include, for example, quinolinyl, isoquinolinyl, indolyl, purinyl, benzimidazolyl, benzopyrrolyl, and benzothiazolyl.

The term "alkoxy" embraces linear or branched alkyl groups that are attached to divalent oxygen. The alkyl group is the same as described herein. Examples of such substituents include methoxy, ethoxy, t-butoxy, and the like. The term "aryloxy" refers to substituents that have an aryl group attached to divalent oxygen. The aryl group is the same as described herein. An example of such substituents is phenoxy.

The term "alkylthio" as used herein, denotes a substituent with an alkyl group directly attached to a divalent sulfur atom. The alkyl group is the same as described herein. Examples of such substituents include methylthio, ethylthio, and the like. Similarly, the term "arylthio" as used herein, denotes a substituent with an aryl group directly attached to a divalent sulfur atom. The aryl group is the same as described herein.

The term "carboxyl" refers to the group —C(O)OH. The term "carboxyalkyl" refers to the group —RC(O)OH that is connected to the compound through the alkyl R group. The term "carboxyalkyloxy" refers to the group —ORC(O)OH, in which the R is an alkyl (e.g., $(CH_2)_n$, alkylene group, where n is 1 to 12) group.

The terms "amine" or "amino" as used herein are represented by the formula $NR^1R^2A^3$, where $R^1$, $R^2$, and $R^3$ can be, for example, independently, hydrogen or substituted or unsubstituted alkyl, cycloalkyl, alkenyl, cycloalkenyl, alkynyl, cycloalkynyl, aryl, or heteroaryl group as described herein. The term "amide" as used herein is generally represented by the formula: $R^1(CO)NR^2R^3$, where either or both $R^2$ and $R^3$ may be hydrogen. An amide is an amine where one of the nitrogen substituents is an acyl group. A "thioamide" as used herein is generally represented by the formula: $R^1(CS)NR^2R^3$, where either or both $R^2$ and $R^3$ may be hydrogen.

The term "alkylamino" refers to a secondary amine substituent with one hydrogen and one alkyl group directly attached to a trivalent nitrogen atom. In addition, the term "alkylamino" also refers to a tertiary amine substituent with two of the same or different alkyl groups directly attached to a trivalent nitrogen atom. The alkyl group is the same as described herein.

The term "alkylamido" refers to substituents of the formula, —C(O)NRR' or —NRC(O)R', in which R and R' are the same or different and each is a hydrogen or alkyl group, as described herein. The term "haloalkylamido" is an alkylamido as described above, in which one or more of the alkyl groups is substituted with a halo moiety, such as, for example, chlorine, bromine or iodine.

The term "amino acid-containing group" refers to substituents that include both a carboxyl group (C(O)OH) and an amino group ($NH_2$). Commonly, such substituents have the generic formula, —$RCH(NH_2)CO_2H$, in which the substituent bonds to a compound of any of formulas (I)-(IX) through the R group. While any amino acid is to be considered (e.g., glycinyl, alaninyl, leucinyl, etc.) acceptable as a substituent, asparate (—$CH(NH_2)CO_2H$) and glutamate (—$CH_2CH(NH_2)CO_2H$) are especially preferred. Therefore, when any substituent of (I)-(IX) is asparate or glutamate, the entire nitrogen substituent forms aspartic acid or glutamic acid, respectively.

Also, unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture.

For sake of brevity, preferred compound backbones are discussed and illustrated hereinafter without the detail of all particular substituent groups, e.g., $R^{1-20}$.

The following are exemplary presently preferred compound backbones, without limitation, according to embodiments of this invention. Each backbone is illustrated with exemplary substituents, such as carboxyl groups at all R' and a nitro group as an X substituent on aromatic rings, and can be additionally or alternatively substituted as described above for formula (I).

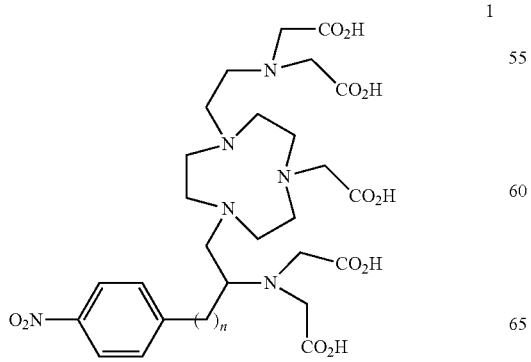

1

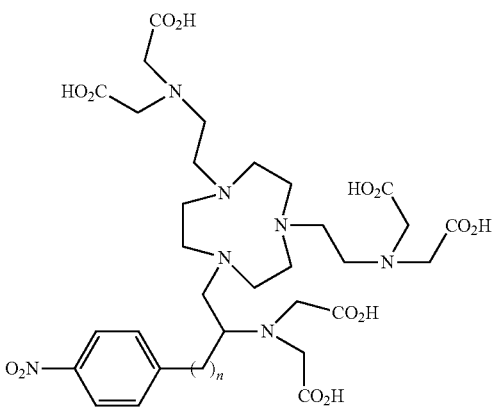

2

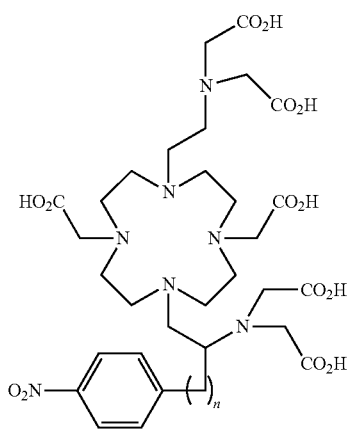

3

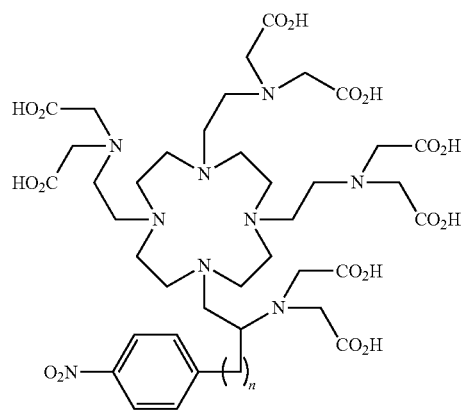

4

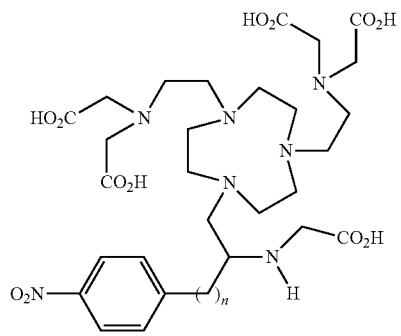

5

6
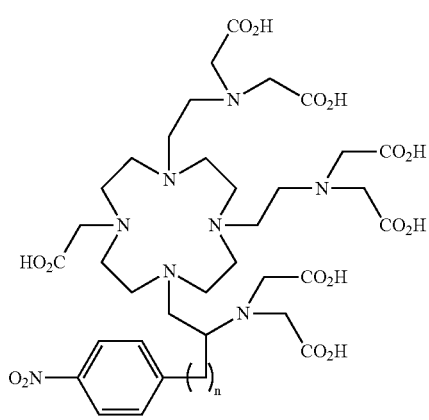
7
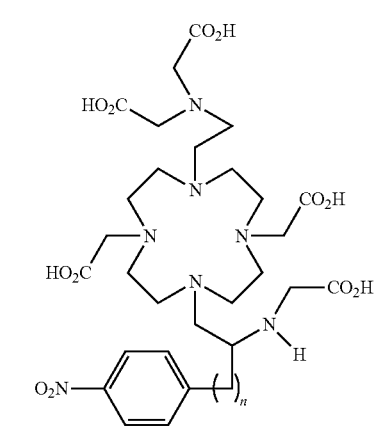
8
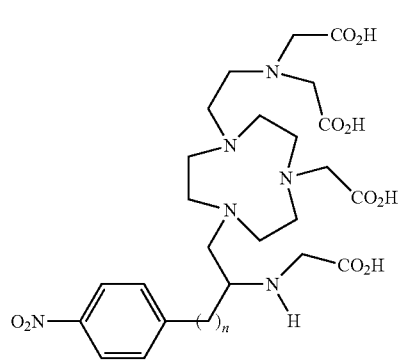
9
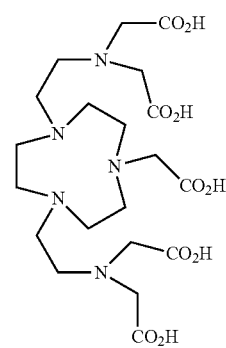
10
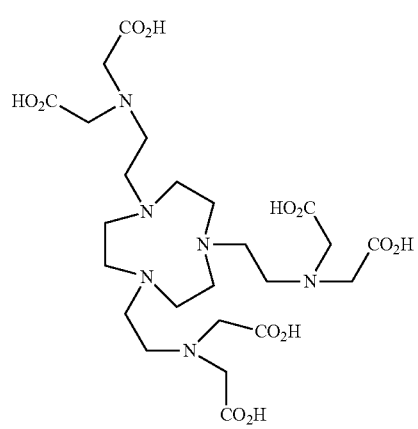
11
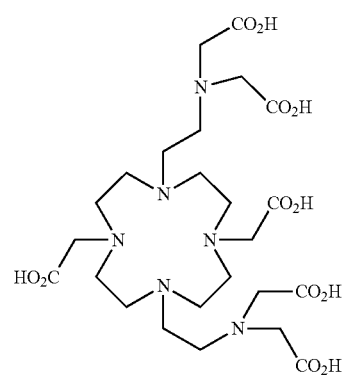
12
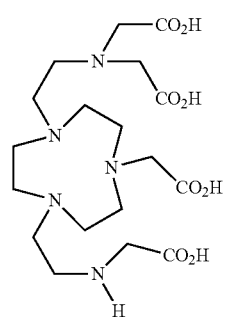
13
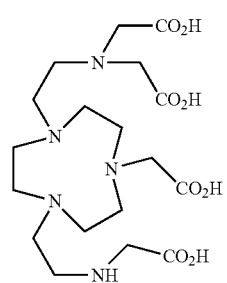

14
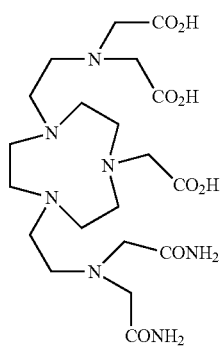
15
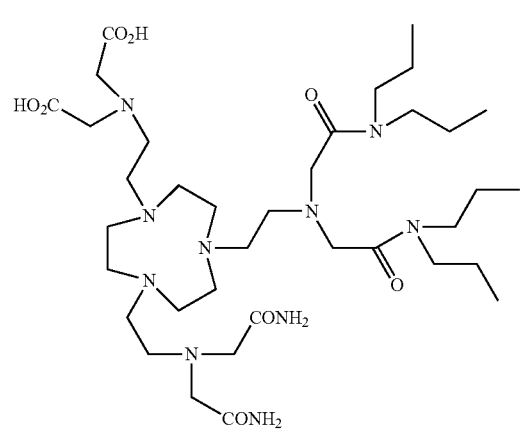
16
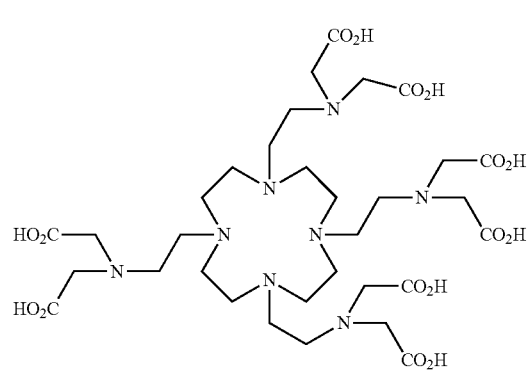
17
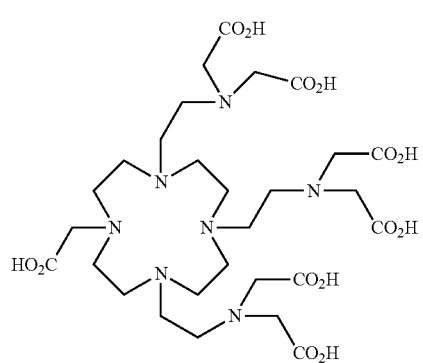
18
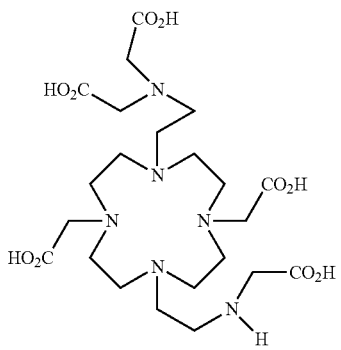
19
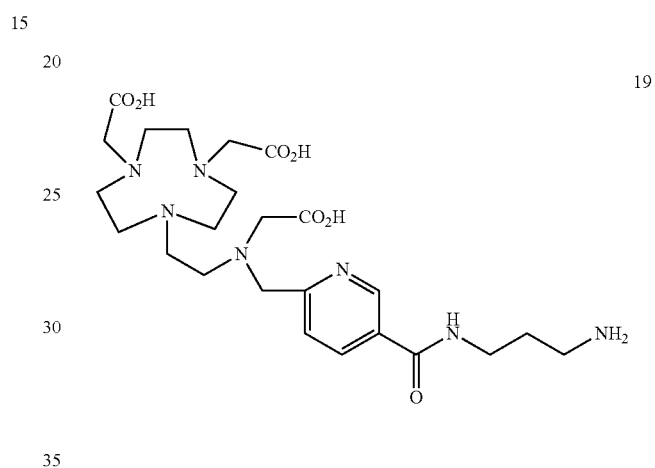
20
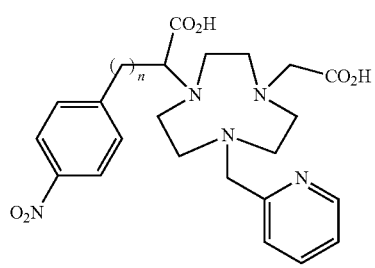
21
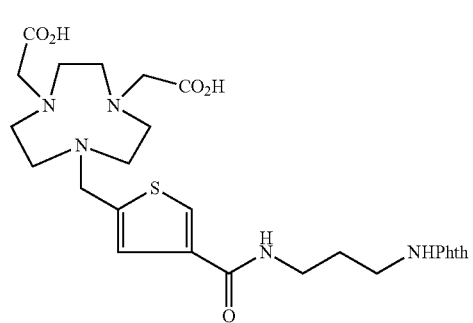

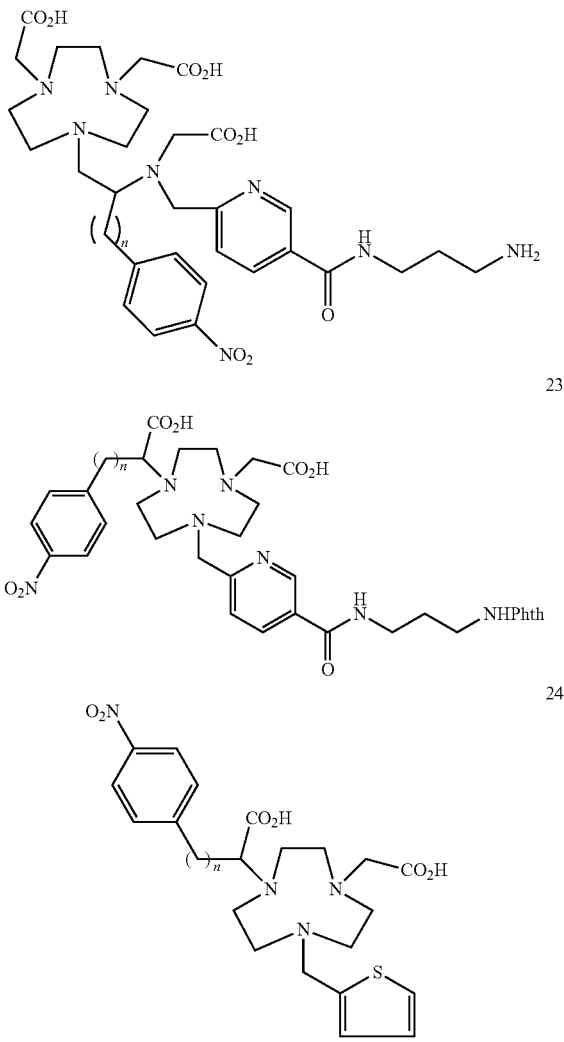

The functionality of the substituents (i.e., $R^{1-20}$ and X) of the compounds of the invention allow derivatization to biomolecules or targeting moieties. The term "biomolecule" refers to all natural and synthetic molecules that play a role in biological systems. Biomolecules include hormones, amino acids, peptides, peptidomimetics, proteins, deoxyribonucleic acid (DNA), ribonucleic acid (RNA), lipids, albumins, polyclonal antibodies, receptor molecules, receptor binding molecules, haptens, monoclonal antibodies, and aptamers. In one preferred embodiment of this invention, at least one X in the above compounds is desirably $NO_2$, $NH_2$, or NCS, and can be substituted for a targeting moiety or biomolecule, such as a hormone, a bile acid, an amino acid, a peptide, a peptidomimetic, a protein, deoxyribonucleic acid (DNA), ribonucleic acid (RNA), a lipid, an albumin, a receptor molecule, a receptor binding molecule, a hapten, a monoclonal antibody, a polyclonal antibody, a peptide, an aptamer, a folic acid, an estrogen, or a transferring. Specific examples of biomolecules include insulins, prostaglandins, growth factors, liposomes, and nucleic acid probes. An advantage of using biomolecules is tissue targeting through specificity of delivery.

In one embodiment of this invention, any suitable hapten can be linked with a compound of any of formulas (I)-(II).

Haptens such as hormones, steroids, enzymes and proteins are desirable in some applications because of their site specificity to tumors and/or various organs of the body. A preferred hapten for use in treating cellular disorders or various disease conditions is a monoclonal antibody. Methods of bonding a macrocyclic compound to a hapten are described in U.S. Pat. No. 5,428,154, which is incorporated herein by reference.

Coupling of a compound of any of formulas (I)-(II) to one or more biomolecules can be accomplished by several known methods (see, for example, Krejcarek et al., Biochem. Biophys. Res. Commun., 1977, 30, 581; Hnatowich et al., Science, 1983, 220, 613). For example, a reactive moiety present in one of the substituents (i.e., $R^{1-18}$ or X) is coupled with a second reactive group located on the biomolecule. Typically, a nucleophilic group is reacted with an electrophilic group to form a covalent bond between the biomolecule and the compound of any of formulas (I)-(II). Examples of nucleophilic groups include amines, anilines, alcohols, phenols, thiols, and hydrazines. Examples of electrophilic groups include halides, disulfides, epoxides, maleimides, acid chlorides, anhydrides, mixed anhydrides, activated esters, imidates, isocyanates, and isothiocyanates.

Preferably, a compound including an aromatic or heteroaromatic ring is bonded to a biomolecule through at least one X substituent. It is especially preferred that an X substituent of aromatic or heteroaromatic ring is a substituent that conjugates the compound to a biomolecule. This substituent is desirably a free-end nitro group, which can be reduced to an amine. The amine then can be activated with a compound, such as thionyl chloride, to form a reactive chemical group, such as an isothiocyanate. An isothiocyanate is preferred because it links directly to an amino residue of a hapten, such as an mAb. The aniline group can be linked to an oxidized carbohydrate on the protein and, subsequently, the linkage fixed by reduction with cyanoborohydride. The amino group also can be reacted with bromoacetyl chloride or iodoacetyl chloride to form —$NHCOCH_2Q$, with Q being bromide or iodide. This group reacts with any available amine or sulfhydryl group on a hapten to form a stable covalent bond. If tyrosine is used in the formulation of the macromolecule, a carboxylic acid or methoxy carboxylate group can be in this position of the compound. The most desirable X substituents for compounds of aromatic or heteroaromatic ring are members selected from the group consisting of hydrogen, halo, alkyl, hydroxy, nitro, amino, alkylamino, thiocyano, isothiocyano, carboxyl, carboxyalkyl, carboxyalkyloxy, amido, alkylamido and haloalkylamido. In some preferred instances, X is a haloalkylamido of the formula —$NHCOCH_2Q$, with Q being bromide or iodide. Another preferred substituent for this position is isothiocyano (—NCS).

The invention also includes complexes comprising the compound of any of formulas (I)-(II) and a metal ion, in which is the metal ion is optionally radioactive. The metal ion is any metal ion that is suitable for the desired end use of the complex. Typical metal ions for forming a complex of the invention include Ac, Al, Bi, Pb, Y, Mn, Cr, Fe, Co, Zn, Ni, Tc, Gd, In, Ga, Cu, Re, Sm, Pm, Ho, Zr, Am, Ce, U, lanthanides (i.e., any element with atomic number 57 to 71 inclusive), and actinides (i.e., any element with atomic number 89 to 103 inclusive). For example, in proton magnetic resonance imaging, paramagnetic metal atoms such as gadolinium(III), manganese(II), manganese(III), chromium (III), iron(II), iron(III), cobalt(II), nickel(II), copper(II), praseodymium(III), neodymium(III), samarium(III), ytterbium (III), terbium(III), dysprosium(III), holmium(III), Europium (III), and erbium(III) (all are paramagnetic metal atoms with favorable electronic properties) are preferred as metals complexed by the ligands of any of formulas (I)-(II). Gadolinium (III) is a preferred complexed metal due to the fact that it has the highest paramagnetism, low toxicity when complexed to a suitable ligand, and high lability of coordinated water. For use as x-ray contrast agents, the metal ion must be able to absorb adequate amounts of x-rays (i.e., radio-opaque), such as, for example, indium, yttrium, lead, bismuth, gadolinium, dysprosium, holmium and praseodymium.

Compounds of each of formulas (I)-(II) also can be complexed with a radioactive metal ion, e.g., Ac, Al, Bi, Pb, Y, Mn, Cr, Fe, Co, Zn, Ni, Tc, In, Ga, Cu, Re, Sm, Am, Ce, U, a lanthanide, or an actinide, for use as therapeutic agents (e.g., radiopharmaceuticals). Other suitable radioisotopes include, without limitation, radioactive isotope of carbon, nitrogen, iodine, fluorine, oxygen, or helium. Specific examples of radionuclides suitable for complexing to a compound of formulas (I)-(II) for various imaging techniques, including single photon emission computed spectroscopy, are, for example, $^{213}$Bi, $^{212}$Bi, $^{212}$Pb, $^{225}$Ac, $^{177}$Lu, $^{111}$In, $^{166}$Ho, $^{90}$Y, $^{153}$Sm, $^{149}$Pm, $^{67}$Cu, $^{64}$Cu, $^{153}$Gd, $^{157}$Gd, $^{66}$Ga, $^{68}$Ga, $^{86}$Y, $^{89}$Zr, $^{18}$F, and $^{67}$Ga.

To prepare metal complexes of the invention, a compound of any of formulas (I)-(II) are complexed with an appropriate metal or metal ion. This can be accomplished by any methodology known in the art. For example, the metal can be added to water in the form of an oxide, halide, nitrate or acetate (e.g., yttrium acetate, bismuth iodide) and treated with an equimolar amount of a compound of any of formulas (I)-(II). The compound can be added as an aqueous solution or suspension. Dilute acid or base can be added (where appropriate) to maintain a suitable pH. Heating at temperatures as high as 100° C. for periods of up to 24 hours or more can be employed to facilitate complexation, depending on the metal, the compound, and their concentrations.

Pharmaceutically acceptable salts of the metal complexes of the compounds of any of formulas (I)-(II) are also useful as imaging agents. These salts can be prepared by using a base (e.g., an alkali metal hydroxide, meglumine, arginine or lysine) to neutralize the above-prepared metal complexes, while they are still in solution. Some of the metal complexes are formally uncharged and do not need cations as counterions. Such neutral complexes may be preferred as intravenously administered x-ray and NMR imaging agents over charged complexes because they may provide solutions of greater physiologic tolerance due to their lower osmolality. However, for use as hepatobiliary agents, negatively charged ligands are preferred.

The above described compounds and complexes can be coupled, e.g., chemically bonded, to a targeting moiety. Exemplary targeting moieties of this invention include bile acids, amino acids, antibodies, peptides, transferrin, or silica amino nanoparticles. Preferably, the X group is or includes a nitro, amino, alkylamino, thiocyano, isothiocyano, alkoxy, aryloxy, carboxyl, carboxyalkyl, carboxyalkyloxy, amido, alkylamido or holoalkylamido attached to the targeting moiety.

In one embodiment of this invention, one or more compounds of formulas (I)-(II), and the complexes thereof, are conjugated with a bile acid targeting moiety. These bile acid conjugates are useful in, for example, preparing MRI contrast agents, such as liver-specific MRI contrast agents. The bile acid serves as a liver or intestine targeting moiety. The property of amphifacial bile acid to undergo enterohepatic circulation and form helical aggregates makes it a useful shuttle system to deliver various drugs to the liver and intestine with favorable intestine absorption and pharmacokinetic profile. Bile acids are efficiently taken up into the cells by two types of carriers: apical sodium-dependent bile salt transporters (ASBT) carriers and Na$^+$-independent carriers. Studies have demonstrated that bile acids enter liver and colon cancer cells which over express bile acid transporter and carriers.

Exemplary bile acid targeting moieties include cholic acid, deoxycholic acid, chenodeoxycholic acid, glycocholic acid, or ursodeoxycholic acid. Exemplary bile acid antitumor conjugates of bile acids and the above described compounds include the following structures. These structures can be further complexed with the metal ions or isotopes discussed above.

In another embodiment of this invention, the targeting moiety includes the biomolecule transferrin. Transferrin is a blood plasma protein for iron ion delivery. Transferrin is a glycoprotein, which binds iron very tightly but reversibly. When not bound to iron, it is known as "apotransferrin." When a transferrin protein loaded with iron encounters a transferrin receptor on the surface of a cell, it binds to it and is consequently transported into the cell in a vesicle. The cell will acidify the vesicle, causing transferrin to release its iron ions. The receptor is then transported through the endocytic cycle back to the cell surface, ready for another round of iron uptake. Each transferrin molecule has the ability to carry two iron ions in the ferric form (Fe$^{3+}$). Conjugates of this invention including transferrin will be particularly useful in targeting transferrin receptors, and will help the hydrophilic ligands of this invention to get into the cell (using apotransferrin). The following exemplary conjugates include transferrin (Tf).

The compounds of this invention, and also complexes and conjugates of these compounds, are useful in diagnostic imaging and radiotherapy. In one embodiment of this invention is provided a method for obtaining a diagnostic image of a host by administering to the host a compound, conjugate, or complex of one or more of formulas (I)-(II), in an amount effective to provide an image, and exposing the host to an energy source, whereupon a diagnostic image of the host is obtained. The diagnostic image can be, for example, a magnetic resonance image (MRI), a fluorescence image (FI), an x-ray contrast image, transmission electron microscopy image, and a positron emission tomography (PET) image, a single photon emission computed spectroscopy (SPECT), or any similar image.

For example, the compounds of any of formulas (I)-(II) can be complexed with a paramagnetic metal atom and used as relaxation enhancement agents for magnetic resonance imaging. These agents, when administered to a host (e.g., a mammal such as a human) distribute in various concentrations to different tissues, and catalyze the relaxation of protons in the tissues that have been excited by the absorption of radiofrequency energy from a magnetic resonance imager. This acceleration of the rate of relaxation of the excited protons provides for an image of different contrast when the host is scanned with a magnetic resonance imager. The magnetic resonance imager is used to record images at various times, generally either before and after administration of the agents, or after administration only, and the differences in the images created by the presence of the agent in tissues are used in diagnosis. Guidelines for performing imaging techniques can be found in Stark et al., Magnetic Resonance Imaging, Mosbey Year Book: St. Louis, 1992, hereby incorporated by reference.

Accordingly, the present invention provides a method for magnetic resonance imaging of a host (e.g., mammal, such as a human). The method comprises administering to the host a complex of any of formulas (I)-(II), in which the metal is paramagnetic, in an amount effective to provide an image; and exposing the host to a magnet, whereupon a magnetic resonance image of the host is obtained. Preferably, a complex used in obtaining a magnetic resonance image comprises Gd. Paramagnetic metal complexes of the present invention are particularly useful as hepatobiliary agents, i.e., for magnetic resonance imaging of the liver and bile ducts. Exemplary MRI contrast agents according to this invention are complexes of the bile acid conjugates discussed above.

The compounds and complexes of this invention can further include a fluorescent molecule, moiety, particle or compound, such as for fluorescence imaging (FI). In one embodiment, the compounds or complexes of this invention are attached to a nanoparticle, such as nanoparticles including carbon nanotubes, silica, quantum dots, or dendrimers. The nanoparticles can be, or be attached to, the fluorescent molecule, moiety, particle or compound. Conjugation to silica amino nanoparticles containing a fluorescent moiety can be used in both MRI and FI. Exemplary fluorescents include fluorophores such as NBD.

Radioimmunotherapy (RIT) is a promising technique for targeted treatment or imaging of numerous cancer types. RIT also requires the use of either radioactive or non-radioactive metals, which can be very toxic when deposited in vivo, causing life-threatening side effects. Therefore, the success of clinical applications of both RIT and MRI heavily depends on the performance of the metal-binding ligands. RIT employs tumor-specific monoclonal antibodies (mAb) for selective delivery of a cytotoxic radionuclide to tumor cells to minimize toxicity due to nonselective exposure of the radionuclide. The RIT system generally requires three components: a radionuclide, a mAb, and a bifunctional ligand. The first RIT drug, Zevalin consists of anti-CD20 antibodies, 1B4M-DTPA, and $^{90}$Y, and was proven significant potency in B-cell non-Hodgkin's lymphoma therapy. $^{177}$Lu, $^{90}$Y, $^{212}$Pb, $^{212}$Bi, $^{213}$Bi, and $^{225}$Ac are recognized as promising metallic radionuclides proposed for effective RIT. An adequate bifunctional ligand that can rapidly form a stable complex with a short-lived radionuclide after being conjugated to a sensitive mAb must be employed to minimize toxicity due to dissociation of metal complex and radiolytic damage to protein conjugates resulting from extended exposure of sensitive antibody to reaction mixture during radiolabeling.

Positron emission tomography, also called PET imaging or a PET scan, is a diagnostic examination that involves the acquisition of physiologic images based on the detection of radiation from the emission of positrons. Positrons are particles emitted from a radioactive substance administered to the patient. The subsequent images of the human body developed with this technique are used to evaluate a variety of diseases. PET scans are used most often to detect cancer and to examine the effects of cancer therapy by characterizing biochemical changes in the cancer. These scans can be performed on the whole body. PET scans of the heart can be used to determine blood flow to the heart muscle and help evaluate signs of coronary artery disease. PET scans of the heart can also be used to determine if areas of the heart that show decreased function are alive rather than scarred as a result of a prior heart attack. Combined with a myocardial perfusion study, PET scans allow differentiation of nonfunctioning heart muscle from heart muscle that would benefit from a procedure, such as angioplasty or coronary artery bypass surgery, which would reestablish adequate blood flow and improve heart function. PET scans of the brain are used to evaluate patients who have memory disorders of an undetermined cause, suspected or proven brain tumors or seizure disorders that are not responsive to medical therapy and are therefore candidates for surgery.

Copper is a preferred metal for PET. Among the available copper radioisotopes, $^{64}$Cu ($t_{1/2}$=12.7 h, $E_{max}^{\beta+}$=656 keV; $E_{max}^{\beta-}$=573 keV) has been shown to be effective for use in positron emission tomography (PET) imaging and targeted radiation therapy applicable to many types of cancer. Bifunctional ligands that possess both binding moieties of Cu(II) and a functional group for conjugation to a targeting moiety are required for the modalities. Research efforts have been directed towards the development of optimal bifunctional ligands that can rapidly form stable complexes with the short-lived $^{64}$Cu while being conjugated to a targeting moiety, either peptide or antibody, to provides an efficient way of generating stable and safe copper radioisotope-labeled drugs for cancer therapy and imaging.

While the above-described uses for the metal-chelating ligands of the present invention are preferred, those working in the diagnostic arts will appreciate that the ligands also can be complexed with the appropriate metals and used as contrast agents in other imaging techniques, such as x-ray imaging, radionuclide imaging and ultrasound imaging, and in other forms of radiotherapy. Accordingly, the present invention further provides a method for x-ray imaging of a host. The method comprises administering to the host a complex of any of formulas (I)-(II), in which the metal ion is radio-opaque, in an amount effective to provide an image; and exposing the host to x-rays, whereupon an x-ray contrast image of the host is obtained. The usefulness of metal ions in in vitro and in vivo diagnostic procedures is disclosed in U.S. Pat. No. 4,454,106, hereby incorporated by reference. X-ray contrast imaging procedures can be found in Moss et al., Computed Tomography of the Body, W. D. Saunders Company: Philadelphia, 1992; and M. Sovak, Editor, Radiocontrast Agents, Springer-Verlag: Berlin, 1984, hereby incorporated by reference.

In one desirable embodiment of this invention, a diagnostic process uses $^{111}$In. The radioactive probe $^{111}$In decays with a half life of 2.8 days (67 hours) to an excited state of the daughter nucleus $^{111}$Cd. From this excited state, a cascade of two gamma-rays is emitted, encompassing an isomeric state with a half life of 85 ns. $^{111}$In is useful for single photon emission computed spectroscopy (SPECT), which is a diagnostic tool. Thus, when $^{111}$In is complexed to a compound of any of formulas (I)-(II) and linked to a biomolecule, such as a hapten, which specifically localizes in a tumor, then that particular localization can be three-dimensionally mapped for diagnostic purposes in vivo by single photon emission tomography. Alternatively, the emission can be used in vitro in radioimmunoassays. The present invention provides a method for SPECT imaging of a host (e.g., mammal, such as a human). The method comprises administering to the host a complex of any of formulas (I)-(II), in which the metal emits a single photon, in an amount effective to provide an image; and exposing the host to an energy source, whereupon a SPECT image of the host is obtained.

The invention also provides a method for treating a cellular disorder or infectious disease in a mammal, such as treating cancer, iron overload disease, a neurodegenerative, including Alzheuner's disease (AD), Parkinson's disease (PD), tuberculosis, HIV, fungal disease, or amalaria disease. The method includes the steps of administering to the mammal at least one of the compounds, or complexes or conjugates of the compounds, of this invention in an amount effective to treat the cancer, the iron overload disease, the neutrodegenerative or infectious diseases, whereupon the cellular disorder is treated. The treatment can be prophylactic or therapeutic. "Prophylactic" refers to any degree in inhibition of the onset of the cellular disorder, including complete inhibition. "Therapeutic" refers to any degree in inhibition or any degree of beneficial effects on the disorder in the mammal (e.g., human), e.g., inhibition of the growth or metastasis of a tumor.

Preferably, the method includes administration of a metal complex bound to a biomolecule, such as hapten, having a selective binding site on a cell affected by the disorder. For example, the X position of the disclosed compounds of this invention can be bound to an antibody, wherein the antibody is directed and created against an epitope found specifically on tumor cells. Thus, when $^{212}$Pb is transported to the antigen site by the complex, and subsequently decays in secular equilibrium to $^{212}$Bi and its daughters, a beta irradiation is produced from the lead disintegration. In addition, a beta radiation is produced by the bismuth daughters. This beta radiation is similar to the beta radiation from $^{90}$Y but, in addition, each disintegration of bismuth also produces an alpha particle. In this manner, a radiotherapy is provided with a radiation dose from an alpha particle and a beta particle. If desired, only $^{212}$Bi can be introduced in those cases where the disorder to be treated, such as with leukemic cells, can be easily reached within the 1 hour half-life of $^{212}$Bi. Suitable procedures using radiopharmaceuticals can be found in the literature (see, for example, Mettler Jr. et al., Essentials of Nuclear Medicine Imaging, Grune and Stratton, Inc.: New York, 1983).

It is possible to use this method to treat cancer, where the cells are widely differentiated. Cancers suitable for treatment with compounds, conjugates, complexes, and compositions of the invention include, for example, lymphomas, leukemias, colo-rectal cancer, ovarian cancer, breast cancer, and prostate cancer. This method might even be preferred where only a long-range beta emitter, such as $^{90}$Y, is desired. In differing environments in vivo, the $^{212}$Bi is retained inside the chelate after the beta emission in varying amounts. Most desirably, at least 95% of $^{212}$Bi remains in the metal complex. In an acidic medium, such as the stomach, at least about 70% of the $^{212}$Bi is retained. Retaining at least about 80% or 90%, $^{212}$Bi is also desirable depending on the medium.

Compounds and complexes of this invention are useful in radiotherapy of diseases such as cancer. The compounds of this invention are chelators of, for example, copper radioisotopes for use in radiation therapy. As discussed above and further below, ligands of this invention can be radiolabeled with $^{64}$Cu and have demonstrated in vitro stability.

Iron is a critical element for the function of the human body, such as for DNA synthesis and regulation of cell cycling. However, free iron, if present in excess, can be dangerous, because it participates in the Haber-Weiss reaction wherein highly reactive oxygen species (ROS) are generated causing life-threatening damage to tissues such as iron overloading diseases and cancers. Many studies indicate that high level of iron accumulated in animals and humans is associated with both the initiation and progression of cancers. It is known that cancer cells require more iron than normal cells and are sensitive to iron depletion. The high demand of iron results from enhanced production of an iron storage protein, ferritin or transferrin receptor (TfR) which governs the uptake of iron into cells from transferrin. The requirement of iron in cancerous cells is also enhanced because iron plays an essential role in the catalytic activity of iron-containing enzyme ribonucleotide reductase (RR). Two dimeric proteins (R1, R2) in RR catalyse the reduction of ribonucleotides to deoxyribonucleotides, the building blocks for DNA synthesis and repair. Cancer cells including Hela and colon cancers and colorectal liver metastates are found to overexpress TfR, RR, or other proteins involved in intracellular iron uptake.

The enhanced requirement of iron in cancer cells as compared to normal cells makes iron depletion using iron chelators targeting TfR, RR, or other proteins involved in iron uptake one of the most efficient strategies to prevent or suppress the rapid proliferation of cancerous cells. Iron chelators are reported to cause cellular iron depletion and exhibit potent cytotoxic activities on diverse cancer cells. Triapine (3-aminopyridine-2-carboxaldehyde thiosemicarbazones), a potent RR inhibitor is a promising iron depleting anti-cancer agent. Cell culture experiments conducted on epithelial ovarian cancer cells indicated that triapine induces apoptosis through an intrinsic pathway. Triapine has been administered intravenously in a number of Phase I and II clinical trials involving patients of various cancers. Hydrophilic iron chelators such as DFO and DTPA have been extensively explored for iron depletion antitumor therapy. DFO has been approved for treatment of iron overload diseases. In addition to its proven iron clearing efficacy, DFO was shown to be effective in inducing apoptotic cell death and exhibited inhibitory and anti-proliferative activity on tumor cells including leukemia, bladder carcinoma, and hepatoceilluar carcinoma, most likely due to RR inhibition as a consequence of iron depletion. Two clinical trials involving leukemia patients resulted in the reduction of peripheral blast cell counts, purportedly suggesting significant potential of DFO as an antileukemic agent. Polyaminocarboxylate chelate DTPA is an extracellular iron depletion agent. Antitumor inhibitory activity of DTPA was demonstrated using human neuroblastoma and ovarian carcinoma cell lines. DTPA displayed iron mobilizing capability comparable to DFO in the clinical study of the iron-overloaded thalassaemic patients.

Conjugates and complexes of the backbone compounds of this invention are useful as potent iron chelators for iron depletion therapy (IDT). The polyaminocarboxylate chelators of this invention are thus useful as anti-tumor agents.

The invention provides a pharmaceutical composition comprising a pharmaceutically acceptable carrier and one or more compounds of any of formulas (I)-(II), a conjugate thereof, or a metal complex thereof. The pharmaceutically acceptable carriers described herein, for example, vehicles, adjuvants, excipients, and diluents, are well-known to those skilled in the art and are readily available to the public. The choice of carrier will be determined, in part, by the particular composition and by the particular method used to administer the composition. Accordingly, there are a wide variety of suitable formulations of the pharmaceutical compositions of the present invention.

One skilled in the art will appreciate that suitable methods of administering a composition of the present invention to an animal, e.g., a mammal such as a human, are also known. Although more than one route can be used to administer a particular composition, a particular route can provide a more immediate and more effective result than another route.

Formulations suitable for oral administration can consist of (a) liquid solutions, such as an effective amount of the compound of any of formulas (I)-(II) dissolved in a diluent, such as water or saline, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The compounds of formulas (I)-(II), alone or in combination with other suitable components, can be made into aerosol formulations to be administered via inhalation. These aerosol formulations can be placed into pressurized acceptable propellants, such as dichlorodifluoromethane, hydrofluorocarbon (such as HFC 134a and/or 227), propane, nitrogen, and the like.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to affect a therapeutic response in the animal over a reasonable time frame or an amount sufficient to allow for diagnostic imaging of the desired tissue or organ. The dose will be determined by the strength of the particular compositions employed and the condition of the animal (e.g., human), as well as the body weight of the animal (e.g., human) to be treated. The size of the dose also will be determined by the existence, nature, and extent of any adverse side effects that might accompany the administration of a particular composition. A suitable dosage for internal administration is 0.01 to 100 mg/kg of body weight per day, such as 0.01 to 35 mg/kg of body weight per day or 0.05 to 5 mg/kg of body weight per day. A suitable concentration of the compound in pharmaceutical compositions for topical administration is 0.05 to 15% (by weight), preferably 0.02 to 5%, and more preferably 0.1 to 3%.

The invention further includes methods of making the compounds of formulas (I)-(II). In one embodiment, a compound of formula (Ib-1):

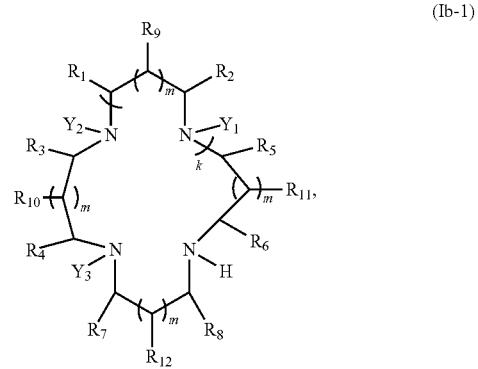

(Ib-1)

wherein: m is 0 or 1; each of $R^{1-12}$ and $Y^{1-3}$ is as defined above, is reacted with a compound of formula (Ib-2) or (Ib-3):

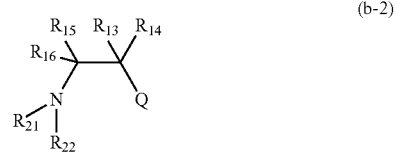

(b-2)

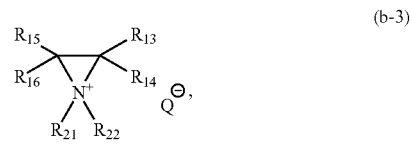

(b-3)

where m is 0 or 1; p is 0 or 1; each of $R^{21-22}$ independently is as defined for $R^{1-20}$; and Q is a counter anion or a leaving group comprising halide, perchlorate, tetrafluoroborate, hexafluoroantimonate, mesylate, triflate, tosylate, carbonate, nitrate, phthalimide, or succinimide. Embodiments of the method include converting (b-2) to (b-3) in the presence of a halosequestering agent including $AgClO_4$, AgOTf, $Ag_2CO_3$, AgOTs, $AgNO_3$, $AgSbF_6$, or $AgBF_4$, and reacting (b-3) in situ with (Ib-1) to obtain (f-1).

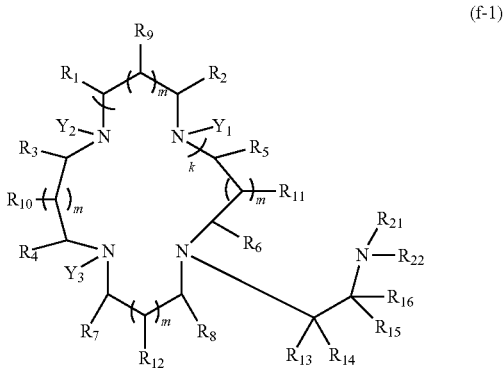

(f-1)

The present invention is described in further detail in connection with the following examples which illustrate or simulate various aspects involved in the practice of the invention. It is to be understood that all changes that come

EXAMPLES

Hexadentate and Pentadenate Chelators for $^{64}$Cu-Based Targeted PET Imaging $^{64}$Cu ($t_{1/2}$=12.7 h, $E_{max}^{\beta+}$=656 keV; $E_{max}^{\beta-}$=573 keV; $E_{max}^{\gamma}$=511 keV) is one of the most useful radioisotopes for positron emission tomography (PET) imaging. A bifunctional chelator that can rapidly complex Cu(II) with high kinetic inertness and thermodynamic stability can be a critical component of clinically viable $^{64}$Cu-based radiopharmaceuticals. Many antibodies and proteins are not tolerant of heating and radiolysis. Efficient radiolabeling of a bifunctional chelator with a short-lived $^{64}$Cu under mild condition is required to minimize radiolysis and for effective targeted PET imaging.

A series of hexadentate and pentadentate NOTA analogues according to this invention, with backbones shown in FIG. 1, were synthesized and evaluated as chelators of $^{64}$Cu. The pentadentate or hexadentate chelators contained different types of donor groups and formed neutral complexes with Cu(II). The chelators were evaluated for complex kinetics and stability with $^{64}$Cu. The chelators instantly bound to $^{64}$Cu with high labeling efficiency and maximum specific activity. All $^{64}$Cu-radiolabeled complexes in human serum remained intact for 2 days. The $^{64}$Cu-radiolabeled complexes were further challenged by EDTA (ethylenediaminetetraacetic acid) in a 100-fold molar excess. The in vitro data indicated strong potential of the chelators for use in targeted PET imaging.

Design of Chelators.

The chelators (FIG. 1) were designed based on various factors including donor number (denticity), donor type, charge of the complex, compatibility between metal ion and donor group that can influence coordination chemistry of a metal. Cu(II) has a relatively small ionic radius of 73 ppm for coordination number 6 and is known to display a high affinity for nitrogen, oxygen, and sulfur donors. A bifunctional version of the parent NOTA chelator (A) was prepared and evaluated for comparison to the new NOTA analogues. A new bifunctional chelator B contains five donor groups and the p-NO$_2$-Bn group that is linked to the macrocyclic backbone by a relatively long propyl chain. Hexadentate chelators C and D contain a carbonyl donor group and a hydroxyl group in addition to the donor groups attached to the macrocyclic backbone, respectively. It would be interesting to evaluate if β-carbonyl or less flexible secondary hydroxyl group can efficiently cooperate with the other donor for rapid and tight complexation with Cu(II). The new hexadentate chelators E and F differ from NOTA wherein one of the aminocaroxylate donors is replaced with a pyridyl (E) or a thiophenyl (F) group. The hexadentate NOTA chelator A can form an anionic complex with Cu(II), while all new pentadentate and hexadentate chelators B—F are expected to form a neutral complex that would have an advantage of less protein interaction and a potentially more favorable in vivo tissue distribution over charged complexes.

Synthesis of New Chelators and their Cu(III) Complexes.

Figure 2:
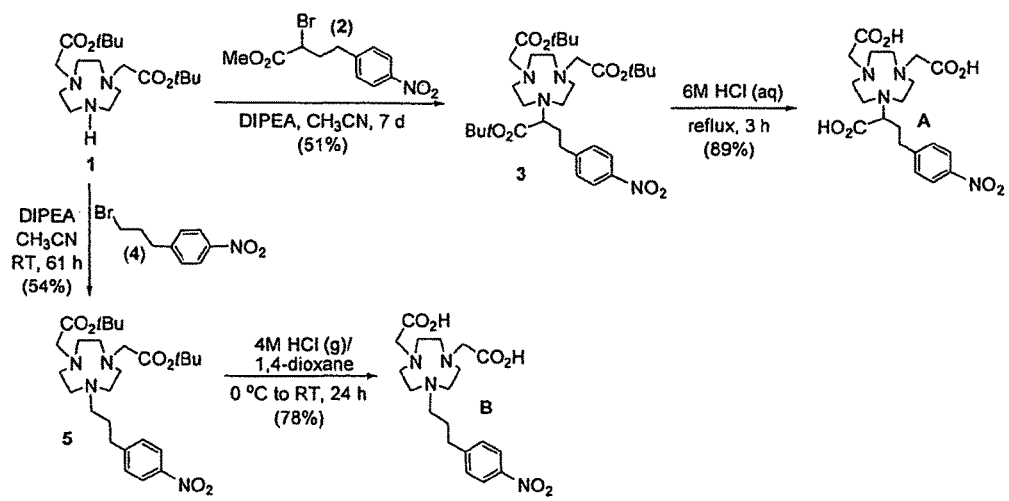
FIG. 2 is a reaction scheme of chelators, according to one embodiment of this invention.
Figure 3:
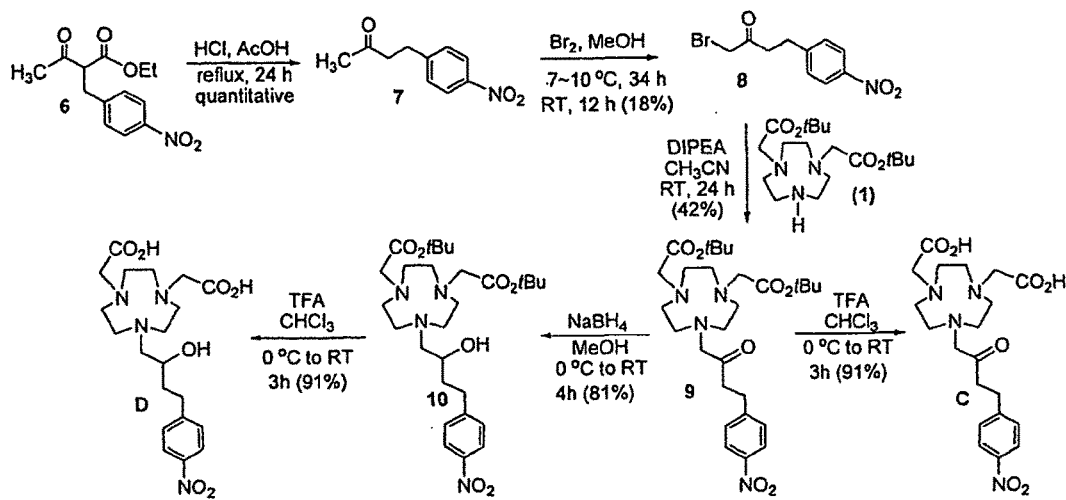
FIG. 3 is a reaction scheme of chelators, according to one embodiment of this invention.
Figure 4:
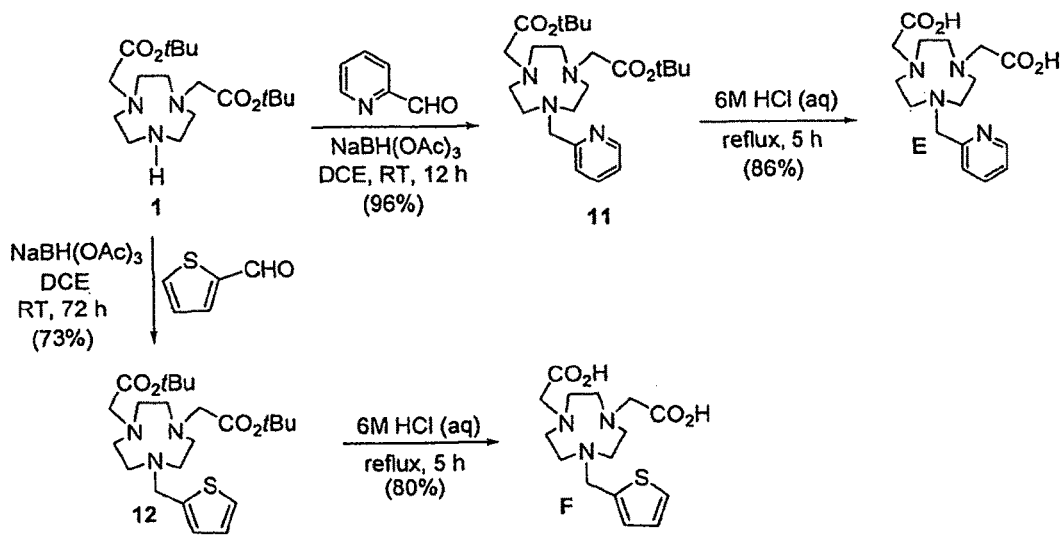
FIG. 4 is a reaction scheme of chelators containing a heteroaromatic ring, according to one embodiment of this invention.

Synthesis of chelators A and B are shown in FIG. 2. Bi-substituted 1,4,7-triazacyclononane (TACN) analogue 1 was reacted with an alkylating agent 2 and 4 to provide the key precursor molecules 3 and 5, respectively. Removal of tert-butyl groups in 3 and 5 was accomplished by treatment of 3 and 5 with HCl (aq) to afford the respective bifunctional chelators A and B. Synthesis of chelators C and D is outlined in FIG. 3. Hydrolysis followed by decarboxylation of 6 under acidic condition provided compound 7 which was subjected to ca-bromination using Br$_2$ to produce 8. Base-promoted reaction of 8 with 1 at room temperature for 24 h provided substitution product 9 which was further treated with TFA to provide chelator C. Compound 9 containing the carbonyl group was reduced to alcohol 10 using NaBH$_4$. tert-butyl groups in 10 was removed by treatment of 10 with TFA in CHCl$_3$ to furnish chelator D. The chelators E and F containing the heteroaromatic rings were synthesized as outlined in FIG. 4. Reductive amination of 2-pyridyl aldehyde and 2-thiophenyl aldehyde with bi-substituted TACN analogue 1 provided compounds 11 and 12, respectively. Compounds 11 and 12 were treated with 6M HCl (aq) and heated to reflux for 5 h to afford the desired chelators E and F.

Cold Cu(II) complexes of the chelators A-F were prepared and characterized by HPLC. A solution of each chelator was reacted with CuCl$_2$ in an equal molar concentration at room temperature for 24 h to provide the corresponding Cu(II) complexes. The Cu(II) complexes were purified using semi-prep HPLC and characterized by analytical HPLC (Supporting Information). The Cu(II) complexes of relatively polar chelator E and F containing pyridyl and thiophenyl ring were eluted earlier with +/−2 min window ($t_R$=4 min and $t_R$=6 min, respectively) as compared to Cu(II) complexes of chelators A-D ($t_R$=7~8 min).

Maximum Specific Activity.

The chelators were evaluated for radiolabeling with $^{64}$Cu to determine the maximum specific activity. The specific activity was determined by titrating chelators with $^{64}$Cu. The chelators in different concentrations (0.0001 μg to 0.1 μg) were labeled with $^{64}$Cu (0.1 M NH$_4$OAc, pH 5.5, 37° C.). All chelators studied bound to $^{64}$Cu with high labeling efficiency (>98%, 1 h). The respective maximum specific activity (Ci/μmol) of 4.87, 51.73, 27.45, 1.18, 14.69, and 1.82 was determined for chelators A-F. It is noteworthy that the pentadentate chelator B bound to $^{64}$Cu with the highest maximum specific activity (51.73 Ci/μmol). A TACN analogue substituted with two N-carboxymethyl groups were known to effectively complex with Cu(II). Introduction of a functional linker to the TACN backbone appears to have little impact on complexation of the donor groups with Cu(II). The relatively lower maximum specific activity was observed with the hexadentate chelators D (1.18 Ci/μmol) and F (1.18 Ci/μmol) containing a hydroxyl group and a thiophenyl group. As compared to the known NOTA bifunctional chelator A, significantly higher specific activity was observed with chelators B, C, and E.

Radiolabeling Reaction Kinetics.

The chelators were evaluated for radiolabeling reaction kinetics with $^{64}$Cu at room temperature (Table 1). Each chelator (0.25M NH$_4$OAc, pH 5.5) was radiolabeled with $^{64}$Cu at room temperature. During the reaction time (30 min), the components were withdrawn at the designated time points (1 min, 10 min, and 30 min), and the radiolabeling efficiency (%) was determined using ITLC (20 mM EDTA in 0.15M NH$_4$OAc). The bifunctional NOTA chelator (A) was employed for comparison and displayed rapid complexation with $^{64}$Cu as expected. All new chelators instantly bound to $^{64}$Cu with excellent radiolabeling efficiency (>99%) at room temperature. Radiolabeling of the chelators with $^{64}$Cu was nearly complete within 1 min as determined by ITLC. $^{64}$Cu-EDTA migrated with the solvent front on TLC ($R_f$=0.93), while $^{64}$Cu-radiolabeled chelator complexes travel slower on the TLC ($R_f$=0.58). The $^{64}$Cu-radiolabeled complexes of the chelators and $^{64}$Cu-EDTA were well separated on the ITLC. All $^{64}$Cu-radiolabeled complexes were shown to be stable against EDTA in present in TLC eluent.

TABLE 1

Radiolabeling kinetics of chelators with $^{64}$Cu (0.25M NH$_4$OAC, pH 5.5, RT)[#]

| Time | Bound complex (%) | | | | | |
|---|---|---|---|---|---|---|
| (h) | A | B | C | D | E | F |
| 1 | 99.8 ± 0.1 | 99.7 ± 0.1 | 99.3 ± 0.3 | 99.0 ± 0.0 | 99.9 ± 0.1 | 99.8 ± 0.2 |
| 10 | 99.8 ± 0.2 | 99.6 ± 0.4 | 99.2 ± 0.9 | 99.6 ± 0.2 | 99.9 ± 0.1 | 99.9 ± 0.2 |
| 30 | 99.6 ± 0.3 | 100 ± 0.0 | 99.5 ± 0.5 | 99.5 ± 0.4 | 99.9 ± 0.1 | 99.8 ± 0.2 |

[#]Radiolabeling efficiency (mean ± standard deviation %) was measured in triplicate using ITLC (eluent: 20 mM EDTA in 0.15M NH$_4$OAc).

In Vitro Serum Stability.

In vitro serum stability of the radiolabeled complexes was performed to determine if the chelators radiolabeled with $^{64}$Cu remained stable without loss of the radioactivity in human serum. This was assessed by measuring the transfer of $^{64}$Cu from the complex to human serum proteins using ITLC (20 mM EDTA in 0.15M NH$_4$OAc, Table 2). $^{64}$Cu-radiolabeled chelators were readily prepared from the reactions of the chelators with $^{64}$Cu at room temperature. Essentially no unbound $^{64}$Cu was detected in the reaction mixture at 2 h time point after the reaction at room temperature as determined by ITLC. The $^{64}$Cu-radiolabeled chelators were directly used for serum stability studies (pH 7, 37° C.) without further purification. All $^{64}$Cu-radiolabeled complexes remained intact in human serum for 2 days as evidenced by ITLC analysis (Supporting Information). All $^{64}$Cu-radiolabeled complex of chelator A-F remained quite stable in serum for 2 days. $^{64}$Cu-chelator C was found to be least stable in serum, and ~3% of $^{64}$Cu was dissociated from the complex containing the carbonyl group over 2 days. No measurable radioactivity was released from $^{64}$Cu-chelator E over 2 days. A tiny amount of $^{64}$Cu (<0.3%) was detected from other $^{64}$Cu-complexes of chelators B, D-F.

Stability of $^{64}$Cu-Radiolabeled Complexes in EDTA Solution.

Figure 5:
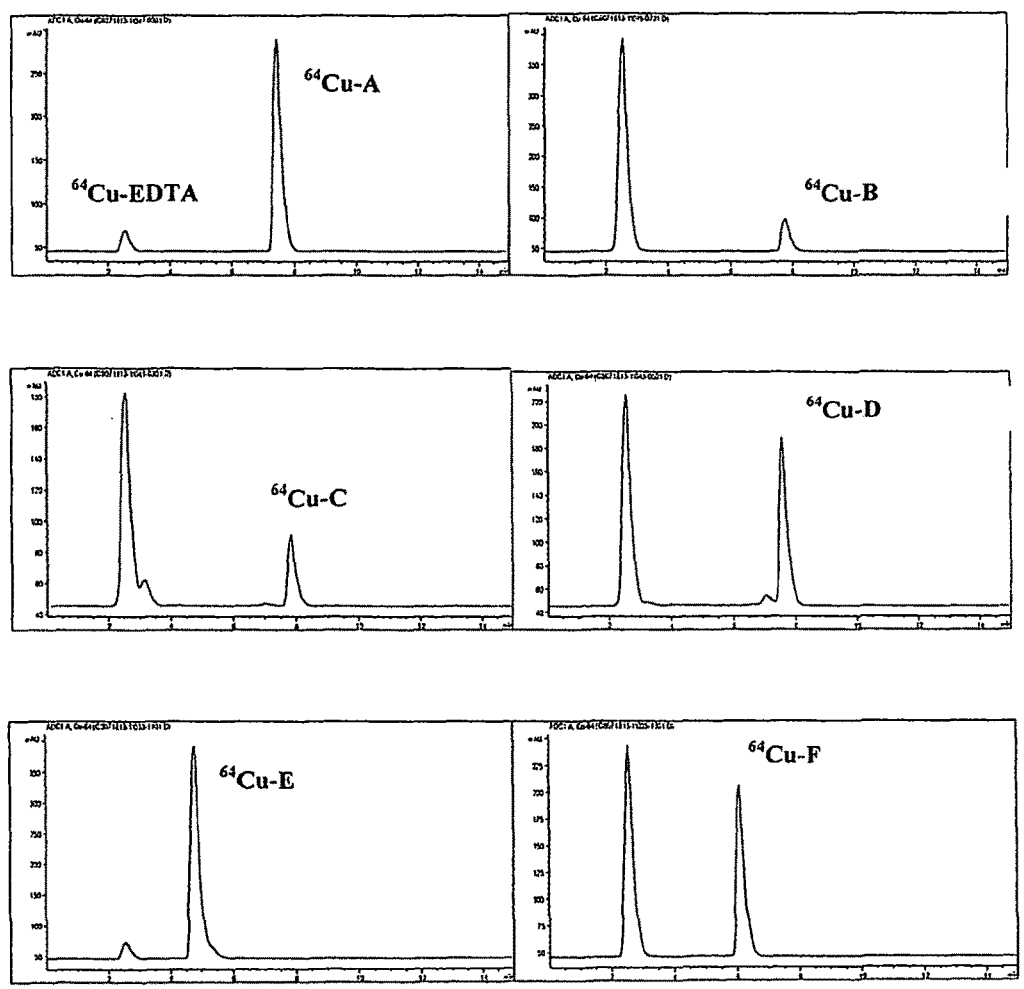
FIG. 5 shows HPLC chromatograms of $^{64}$Cu-radiolabeled complexes against EDTA.

$^{64}$Cu-radiolabeled complexes were further evaluated for complex stability based on EDTA challenge. $^{64}$Cu-radiolabeled complexes were freshly prepared and treated with a solution of EDTA at a 100-fold molar excess, and the resulting solution (pH 5.5) was incubated at 37° C. for 24 h. A sample was withdrawn at different time points (0 h, 1 h, 4 h, and 24 h) and analyzed using both ITLC and HPLC (Table 3 and Supporting Information). $^{64}$Cu-radiolabeled complexes of chelators A and E remained intact against EDTA challenge, and a small portion of the activity (~5%) was transferred from the complexes to EDTA at 24 h time point (ITLC). Among the complexes tested, $^{64}$Cu-radiolabeled pentadentate chelator B was least tolerant of EDTA treated, and most of $^{64}$Cu was dissociated from the complex (~80%) at 24 h time point. $^{64}$Cu-radiolabeled chelator C containing the carbonyl donor group was found dissociated rapidly in the presence of the excess EDTA, and 50% of the activity was transchelated by EDTA at 1 h time point. $^{64}$Cu-radiolabeled chelators D and F with the respective hydroxyl and thiophenyl donor group were slower in dissociation than $^{64}$Cu-radiolabeled chelators B and C and released >45% of $^{64}$Cu at 24 h time point. Dissociation of the activity from the $^{64}$Cu-radiolabeled chelators was also measured using radio-HPLC at 25 h time point (FIG. 5). The peak related to $^{64}$Cu-EDTA ($t_R$=2.5 min) was clearly separated from bound $^{64}$Cu complex of the chelators. $^{64}$Cu-radiolabeled complex of polar chelators E and F have the respective retention time at 4.8 min and 6.2 min, while other $^{64}$Cu-radiolabeled complexes have similar retention time ($t_R$=7~8 min). The $^{64}$Cu-radiolabeled chelators C and D gave a small peak ($t_R$=~3 min and $t_R$=~7 min, respectively). It is speculated that the less stable complexes interact with mobile phase during HPLC to give the minor unbound peaks.

TABLE 2

Complex stability of $^{64}$Cu-radiolabeled complexes in human serum (pH 7, 37° C.)[#]

| Time | Bound complex (%) | | | | | |
|---|---|---|---|---|---|---|
| (day) | A | B | C | D | E | F |
| 0 | 99.9 ± 0.0 | 99.9 ± 0.1 | 99.9 ± 0.1 | 100 ± 0.1 | 99.9 ± 0.0 | 99.9 ± 0.1 |
| 1 | 100.0 ± 0.0 | 100 ± 0.1 | 98.7 ± 0.5 | 100 ± 0.0 | 100.0 ± 0.0 | 99.9 ± 0.1 |
| 2 | 99.9 ± 0.1 | 99.7 ± 0.4 | 97.8 ± 1.1 | 99.9 ± 0.1 | 100.0 ± 0.0 | 99.9 ± 0.0 |

[#]Bound complex (mean ± standard deviation %) was measured in triplicate using ITLC.

TABLE 3

Stability of $^{64}$Cu-radiolabeld complexes in EDTA solution (37° C., pH 5.5)#

| Time (h) | Bound complex (%) | | | | | |
|---|---|---|---|---|---|---|
| | A | B | C | D | E | F |
| 0 | 99.9 ± 0.1 | 99.9 ± 0.1 | 97.7 ± 0.2 | 99.5 ± 0.3 | 99.7 ± 0.1 | 100 ± 0.1 |
| 1 | 98.6 ± 0.6 | 90.4 ± 0.1 | 50.4 ± 0.4 | 86.8 ± 0.7 | 98.2 ± 0.3 | 95.7 ± 0.5 |
| 4 | 96.8 ± 0.0 | 69.2 ± 0.3 | 45.8 ± 1.5 | 79.1 ± 0.4 | 92.6 ± 0.3 | 87.5 ± 0.4 |
| 19 | 95.3 ± 0.5 | 22.9 ± 2.1 | 41.0 ± 0.4 | 59.3 ± 0.0 | 93.6 ± 0.1 | 59.5 ± 0.6 |
| 24 | 94.9 ± 0.0 | 19.4 ± 1.1 | 39.0 ± 0.2 | 55.0 ± 0.6 | 94.3 ± 0.6 | 53.4 ± 1.7 |
| 25* | 90.3 ± 0.3 | 11.9 ± 0.6 | 21.7 ± 1.3 | 41.0 ± 2.6 | 93.1 ± 0.1 | 42.3 ± 0.3 |

Bound complex (mean ± standard deviation %) was measured in duplicate using ITLC.
*Bound complex (mean ± standard deviation %) was measured in duplicate using radio-HPLC.

In summary, the in vitro complexation kinetic and stability data indicate that substitution of the N-carboxymethyl group in the NOTA chelating backbone with a different donor group including heteroaromatic ring, carbonyl group, or hydroxyl group gave no measurable effect on radiolabeling efficiency of the chelators and stability of the corresponding complexes in serum. It appears that the chelators with the adequate macrocyclic cavity and denticity for effective complexation of Cu(III) as a small metal cation are less affected by the donor type. All new chelators were found to be highly effective in binding $^{64}$Cu. It is noteworthy that pentadentate chelator B rapidly bound to $^{64}$Cu and the complex remained intact in serum. However, when rigorously challenged by EDTA at a 100-fold molar excess, $^{64}$Cu-radiolabeled complexes produced different complex stability profiles. The bifunctional NOTA chelator (A) and pyridine-containing chelator (E) was well tolerant of EDTA challenge, and only a small amount of the activity was transferred to EDTA. Other chelators B-D and F radiolabeled with $^{64}$CU were slowly or rapidly dissociated to produce $^{64}$Cu transchelated to EDTA, although the complexes remained stable in human serum over 2 days.

The novel pentadentate or hexadentate NOTA analogues with different donor groups were prepared and evaluated as chelators of $^{64}$Cu. The radiolabeling efficiency data indicate that all new chelators instantly and almost completely bound to $^{64}$Cu at room temperature. All chelators were efficiently radiolabeled with $^{64}$Cu in a broad range of maximum specific activity. The corresponding $^{64}$Cu-radiolabeled complexes remained intact in human serum for 2 days. No obvious effect of donor atom and denticity on complexation kinetics and stability with $^{64}$Cu was observed with the chelators studied. The $^{64}$Cu-radiolabeled complexes of two hexadentate chelators (chelators A and E) were quite inert against rigorous EDTA challenge and released a minimal amount of the activity for 24 h. $^{64}$Cu-chelator A and $^{64}$Cu-chelator E were stable in mice and displayed low radioactivity level in the blood and the normal organs.

Experimental Section

Instruments and Reagents.

$^1$H, $^{13}$C, and DEPT NMR spectra were obtained using a Bruker 300 NMR instrument, and chemical shifts are reported in ppm on the δ scale relative to TMS. Electro spray ionization (ESI) high resolution mass spectra (HRMS) were obtained on JEOL double sector JMS-AX505HA mass spectrometer (University of Notre Dame, IN). $^{64}$Cu was prepared on CS-15 cyclotron at Washington University Medical School, St. Louis, Mo. according to the previous reported method. Radioactivity was counted with a Beckman Gamma 8000 counter containing a NaI crystal (Beckman Instruments, Inc., Irvine, Calif.). Analytical and semi-prep HPLC were performed on Agilent 1200 (Agilent, Santa Clara, Calif.) equipped with a diode array detector (λ=254 and 280 nm), themostat set at 35° C. and a Zorbax Eclipse XDB-C18 column (4.6×150 mm, 80 Å, Agilent, Santa Clara, Calif.). The mobile phase of a binary gradient (0-100% B/40 min; solvent A=0.1% TFA in water; solvent B=0.1% TFA in acetonitrile) at a flow rate of 1 mL/min was used for analytical HPLC (method 1). The mobile phase of a binary gradient (0-100% B/40 min; solvent A: 0.1% TFA in H$_2$O, solvent B: 0.1% TFA in CH$_3$CN, 0-60% B/40 min, flow rate: 3 mL/min) for semi-prep HPLC (method 2).

Tert-Butyl 2-{4,7-bis[2-(tert-butoxy)-2-oxoethyl]-1,4,7-triazonan-1-yl}-4-(4-nitrophenyl)-butanoate (3)

To a solution of 1 (272 mg, 0.761 mmol) in CH$_3$CN (1 mL) was added portion-wise compound 2 (230 mg, 0.761 mmol) and DIPEA (295 mg, 2.284 mmol) in CH$_3$CN (1 mL). The resulting mixture was stirred for 7 days at room temperature while monitoring the progress of the reaction using TLC. The reaction mixture was concentrated to dryness. 0.1M HCl aqueous solution (20 mL) was added to the residue, and the resulting mixture was extracted with CH$_2$Cl$_2$ (2×20 mL). The combined organic layers were dried over MgSO$_4$, filtered, and concentrated to the dryness in vacuo. The residue was purified via column chromatography on silica gel (220-440 mesh) eluting with 15% CH$_3$OH in CH$_2$Cl$_2$ to afford pure product 3 (240 mg, 51%). $^1$H NMR (CDCl$_3$, 300 MHz) δ 1.42 (s, 18H), 1.99 (m, 2H), 2.60-3.04 (m, 15H), 3.18-3.36 (m, 5H), 3.65 (s, 3H), 7.36 (d, J=8.5 Hz, 2H), 8.12 (d, J=8.5 Hz, 2H); $^{13}$C NMR (CDCl$_3$, 300 MHz) δ 28.2 (q), 31.8 (t), 32.7 (t), 51.2 (q), 53.5 (t), 55.5 (t), 56.0 (t), 59.4 (t), 66.4 (d), 80.8 (s), 123.7 (d), 129.4 (d), 146.4 (s), 149.7 (s), 171.4 (s), 173.7 (s). HRMS (positive ion ESI) Calcd for C$_{29}$H$_{47}$N$_4$O$_8$ [M+H]$^+$ m/z 521.3388. Found: [M+H]$^+$ m/z 521.3391.

2-[4,7-bis(carboxymethyl)-1,4,7-triazonan-1-yl]-4-(4-nitrophenyl)butanoic acid (A)

Compound 3 (20 mg, 0.032 mmol) was treated with 6M HCl solution (2 mL), and the resulting solution was refluxed for 3 h. The reaction mixture was cooled to room temperature, and the resulting solution was filtered, and the filtrate was concentrated in vacuo to provide chelator A (16 mg, 89%) as a yellow solid. $^1$H NMR (D$_2$O, 300 MHz) δ 1.82-1.99 (m, 1H), 1.99-2.19 (m, 1H), 2.59-2.84 (m, 2H), 2.85-3.26 (m, 12H), 3.46-3.55 (m, 1H), 3.79 (s, 4H), 7.30 (d, J=8.4 Hz, 2H), 7.99 (d, J=8.4 Hz, 2H); $^{13}$C NMR (D$_2$O, 300

MHz) δ 29.7 (t), 32.1 (t), 45.7 (t), 49.2 (t), 50.6 (t), 55.3 (t), 63.7 (d), 123.7 (d), 129.4 (d), 146.4 (s), 149.7 (s), 172.2 (s), 175.6 (s). The data of $^1$H and $^{13}$C NMR data were essentially identical to those previously reported. Analytical HPLC ($t_R$=7.6, method 1).

Tert-Butyl 2-{4-[2-(tert-butoxy)-2-oxoethyl]-7-[3-(4-nitrophenyl)propyl]-1,4,7-triazonan-1-yl}acetate (5)

To a solution of 1 (72 mg, 0.29 mmol) in CH$_3$CN (2 mL) at 0° C. was added dropwise 4 (105 mg, 0.29 mmol) in CH$_3$CN (1 mL) and DIPEA (112 mg, 0.87 mmol). The resulting mixture was stirred for 60.5 h at room temperature, while monitoring the progress of the reaction using TLC. The resulting mixture was concentrated to dryness in vacuo. Water (10 mL) and 0.1 M HCl aqueous solution (1 mL) were added to the residue, and the resulting mixture was extracted with CHCl$_3$ (3×10 mL). The combined organic layers were dried over MgSO$_4$, filtered, and concentrated to the dryness in vacuo. The residue was purified via column chromatography on silica gel (60-220 mesh) eluting with 20% MeOH in CH$_2$Cl$_2$ to afford 5 (81 mg, 53.6%) as an oil. $^1$H NMR (CDCl$_3$, 300 MHz) δ 1.41 (s, 18H), 2.21 (s, 2H), 2.65-2.90 (m, 8H), 3.01-3.18 (s, 5H), 3.37 (s, 7H), 7.41 (d, J=6.0 Hz, 2H), 8.12 (d, J=6.0 Hz, 2H); $^{13}$C NMR (CDCl$_3$, 300 MHz) δ 25.9 (t), 28.1 (q), 32.8 (t), 49.8 (t), 52.3 (t), 53.5 (t), 55.3 (t), 58.2 (t), 81.7 (s), 123.9 (d), 129.4 (d), 146.7 (s), 147.9 (s), 170.7 (s). HRMS (positive ion ESI) Calcd for C$_{27}$H$_{45}$N$_4$O$_6$ [M+H]$^+$ m/z 521.3334. Found: [M+H]$^+$ m/z 521.3309.

2-[4-(carboxymethyl)-7-[3-(4-nitrophenyl)propyl]-1,4,7-triazonan-1-yl]acetic acid (B)

Compound 5 (20 mg, 0.038 mmol) at 0~5° C. was treated dropwise with 4M HCl (g) in 1,4-dioxane (2 mL) over 10 min. The resulting mixture was gradually warmed to room temperature and stirred for 24 h. Diethyl ether (20 mL) was added to the reaction mixture which was stirred for 10 min. The resulting mixture was capped and placed in the freezer for 1 h. The solid formed was filtered, washed with ether, and quickly dissolved in deionized water. The resulting aqueous solution was concentrated in vacuo to provide chelator B (14 mg, 78%). $^1$H NMR (D$_2$O, 300 MHz) δ 2.02-2.17 (m, 2H), 2.71-2.79 (m, 2H), 3.18-3.24 (s, 4H), 3.25-3.38 (m, 6H), 3.47-3.58 (s, 4H), 3.75-3.82 (s, 4H), 7.37 (d, J=8.4 Hz, 2H), 8.07 (d, J=8.7 Hz, 2H); $^{13}$C NMR (D$_2$O, 300 MHz) δ 24.9 (t), 31.7 (t), 49.6 (t), 50.7 (t), 51.0 (t), 56.9 (t), 57.3 (t), 123.9 (d), 129.5 (d), 146.4 (s), 148.7 (s), 172.9 (s). HRMS (positive ion ESI) Calcd for C$_{19}$H$_{29}$N$_4$O$_6$ [M+H]$^+$ m/z 409.2082. Found: [M+H]$^+$ m/z 409.2087. Analytical HPLC ($t_R$=7.3, method 1).

Ethyl 2-[(4-nitrophenyl)methyl]-3-oxobutanoate (6)

Ethyl acetoacetate (10 g, 76.84 mmol) was added dropwise to NaH (1.84 g, 76.84 mmol) in the THF (220 ml). p-nitro benzyl bromide (16.6 g, 76.84 mmol) was added portion-wise over 1 h. The reaction mixture was stirred for 1.5 h. After evaporation of the solvent, the residue was treated with H$_2$O (100 mL) and extracted with ethyl acetate (2×100 mL). The combined organic layers were dried over MgSO$_4$, filtered, and concentrated to the dryness in vacuo. The residue was recrystallized with EtOH to provide pure product 6 (10 g, 49.1%). $^1$H NMR (CDCl$_3$, 300 MHz) δ 1.20 (t, 3H, J=7.5 Hz), δ 2.23 (s, 3H), δ 3.17-3.31 (m, 2H), δ 3.79 (t, 3H, J=7.5 Hz), δ 4.09-4.20 (m, 2H), δ 7.35 (d, 2H, J=9 Hz), δ 8.11 (d, 2H, J=9 Hz). $^{13}$C NMR (CDCl$_3$, 300 MHz) δ 14.00 (q), 29.48 (q), 33.38 (t), 60.61 (d), 61.84 (d), 123.74 (d), 129.80 (d), 146.10 (s), 148.97 (s), 168.47 (s), 201.18 (s).

4-(4-nitrophenyl)butan-2-one (7)

Compound 6 (10 g, 37.7 mmol) was dissolved in the mixture of acetic acid (85 mL) and conc. HCl (30 mL), and the resulting solution was refluxed for 24 h after which the reaction mixture was allowed to room temperature and concentrated to dryness in vacuo. The residue was treated with H$_2$O (100 ml) and extracted with ethyl acetate (2×100 mL). The combined organic layers were dried over MgSO$_4$, filtered, and concentrated in vacuo to provide pure 7 (7.3 g, 100%). $^1$H NMR (CDCl$_3$, 300 MHz) δ 2.95 (s, 3H), 2.77 (t, 2H, J=7.5 Hz), 2.92 (t, 2H, J=7.5 Hz), 7.28 (d, 2H, J=8.8 Hz), 8.01 (d, 2H, J=8.8 Hz); $^{13}$C NMR (CDCl$_3$, 300 MHz) 329.27 (t), 29.95 (q), 123.58 (d), 129.27 (d), 146.32 (s), 149.15 (s), 206.7 (s). The data of $^1$H and $^{13}$C NMR data were essentially identical to those of 7 as previously reported.

1-bromo-4-(4-nitrophenyl)butan-2-one (8)

To a solution of 7 (5.0 g, 25.88 mmol) in anhydrous methanol (10 mL) was added dropwise bromine (4.14 mg, 25.88 mmol) in anhydrous methanol (10 mL) at 7~9° C. over 1 h. The mixture was stirred for 34 h in same temperature. DI water (30 mL) was added to the mixture which was warmed to room temperature and continuously stirred for 12 h. The reaction mixture was extracted with CH$_2$Cl$_2$ (2×30 mL). The combined organic layers were dried over MgSO$_4$, filtered, and the filtrate was concentrated in vacuo. The residue was purified via column chromatography on silica gel (60-220 mesh) and eluted with 10% ethyl acetate in hexanes to afford 8 (1.26 g, 18.0%) as a solid. $^1$H NMR (CDCl$_3$, 300 MHz) δ 3.04 (s, 4H), 3.87 (s, 2H), 7.35 (d, 2H, J=8.8 Hz), 8.12 (d, 2H, J=8.8 Hz); $^{13}$C NMR (CDCl$_3$, 300 MHz) 329.30 (t), 33.88 (t), 40.32 (t), 123.8 (d), 129.32 (d), 146.61 (s), 148.23 (s), 200.43 (s). HRMS (positive ion ESI) Calcd for C$_{10}$H$_{11}$BrNO$_3$ [M+H]$^+$ m/z 271.9917. Found: [M+H]$^+$ m/z 271.9924.

Tert-Butyl 2-{4-[2-(tert-butoxy)-2-oxoethyl]-7-[4-(4-nitrophenyl)-2-oxobutyl]-1,4,7-triazonan-1-yl}acetate (9)

Compound 8 (114 mg, 0.420 mmol) was added portion-wise to a solution of 1 (150 mg, 0.420 mmol) in CH$_3$CN (5 mL) at 0° C. DIPEA (163 mg, 1.259 mmol) in CH$_3$CN (2 mL) was added portion-wise, and the resulting mixture was allowed to room temperature and stirred for 24 h while monitoring the reaction progress using TLC. The reaction mixture was concentrated to dryness in vacuo. The residue was treated with DI water (10 mL) and extracted with CHCl$_3$ (2×10 mL). The combined organic layer was concentrated in vacuo. Then the resulting mixture was dissolved with 0.1M HCl solution (10 mL) and washed with CHCl$_3$ (2×10 mL). The aqueous layer was neutralized using 0.1M NaOH (10 mL) and extracted with CHCl$_3$ (3×20 mL). The combined organic layers were dried over MgSO$_4$, filtered, and concentrated to the dryness in vacuo. The residue was purified via column chromatography on silica gel (60-220 mesh) eluting with 30% MeOH in dichloromethane containing Et$_3$N to provide pure 9 (96.8 mg, 42.2%). $^1$H NMR (CDCl$_3$, 300 MHz) δ 1.44 (s, 18H), 2.71-3.05 (m, 16H), 3.29 (s, 4H), 3.38 (s, 2H), 7.34 (d, 2H, J=8.8 Hz), 8.12 (d, 2H, J=8.8 Hz);

$^{13}$C NMR (CDCl$_3$, 300 MHz) δ 28.09 (q), 29.14 (t), 40.65 (t), 55.13 (t), 55.39 (t), 55.70 (t), 59.59 (t), 67.48 (t), 80.79 (s), 123.71 (d), 129.29 (d), 146.46 (s), 149.18 (s), 171.38 (s). HRMS (positive ion ESI) Calcd for C28H44N4O7 [M+H]$^+$ m/z 549.6716. Found: [M+H]$^+$ m/z 549.3403.

Tert-Butyl 2-{4-[2-(tert-butoxy)-2-oxoethyl]-7-[2-hydroxy-4-(4-nitrophenyl)butyl]-1,4,7-triazonan-1-yl}acetate (10)

A solution of 9 (33 mg, 0.060 mmol) in anhydrous methanol (1 mL) at 0° C. was added portion-wise NaBH$_4$ (10 mg, 0.264 mmol) over 1 h. The mixture was then warmed to room temperature and stirred for 3 h. The reaction mixture was concentrated to dryness and treated with H$_2$O (10 mL) and extracted with ethyl acetate (2×15 mL). The combined organic layers were dried over MgSO$_4$, filtered, and the filtrated was concentrated in vacuo to provide pure 10 (26.5 mg, 81.0%). $^1$H NMR (CDCl$_3$, 300 MHz) δ 1.45 (s, 18H), 1.59-1.70 (m, 2H), 2.36 (t, 1H, J=11.1 Hz), 2.61-3.05 (m, 15H), 3.30 (s, 4H), 3.51-3.69 (m, 1H), 7.36 (d, 2H, J=8.7 Hz), 8.13 (d, 2H, J=8.7 Hz). $^{13}$C NMR (D$_2$O, 300 MHz) 28.22 (q), 32.22 (t), 35.73 (t), 55.77 (t), 55.99 (t), 56.43 (t), 58.92 (t), 63.79 (t), 67.95 (d), 80.82 (s), 123.59 (d), 129.28 (d), 146.26 (s), 150.63 (s), 171.51 (s). HRMS (positive ion ESI) Calcd for C$_{28}$H$_{47}$N$_4$O$_7$ [M+H]$^+$ m/z 551.3439. Found: [M+H]$^+$ m/z 551.3463.

2-[4-(carboxymethyl)-7-[4-(4-nitrophenyl)-2-oxobutyl]-1,4,7-triazonan-1-yl]acetic acid (C)

TFA (800 µl) was added dropwise to compound 9 (22.6 mg 0.041 mmol) at 0° C., and the resulting solution was stirred for 2 h at 0° C. The resulting mixture was allowed to room temperature and stirred for additional 1 h. The reaction mixture was concentrated to dryness in vacuo and treated with ether (2 mL), and the ether layer was decanted. The residue was dissolved in H$_2$O (2 mL) and washed by CHCl$_3$ (2×5 mL). The aqueous layer was concentrated to dryness in vacuo to provide pure product C (16.4 mg, 91.0%). $^1$H NMR (D$_2$O, 300 MHz) δ 2.86 (dd, 4H, J=5.9, 15.6 Hz), 3.16 (s, 12H), 3.69 (s, 4H), 4.11 (s, 2H), 7.30 (d, 2H, J=9.0 Hz), 8.00 (d, 2H, J=9.0 Hz); $^{13}$C NMR (D$_2$O, 300 MHz) δ 28.45 (t), 39.83 (t), 49.63 (t), 50.06 (t), 50.81 (t), 56.22 (t), 63.76 (t), 123.68 (d), 129.30 (d), 146.06 (s), 148.79 (s), 172.42 (s). HRMS (positive ion ESI) Calcd for C$_{20}$H$_{29}$N$_4$O$_7$ [M+H]$^+$ 1/z 437.2031. Found: [M+H]$^+$ m/z 437.2041. Analytical HPLC (t$_R$=7.8, method 1).

2-[4-(carboxymethyl)-7-[2-hydroxy-4-(4-nitrophenyl)butyl]-1,4,7-triazonan-1-yl]acetic acid (D)

TFA (800 µl) was added dropwise to compound 10 (18.5 mg 0.034 mmol) at 0° C., the resulting mixture was stirred for 2 h at 0° C. The resulting mixture was allowed to room temperature and stirred for additional 1 h. The reaction mixture was concentrated to dryness and treated with ether (2 mL), and the ether layer was decanted. The residue was dissolved in H$_2$O (2 mL) and washed by CHCl$_3$ (2×5 mL). The aqueous layer was concentrated to dryness in vacuo to provide pure product D (7.0 mg, 47.5%). $^1$H NMR (D$_2$O, 300 MHz) δ 1.62-1.81 (m, 2H), 2.58-2.85 (m, 2H), 3.05-3.58 (m, 14H), 3.65-3.85 (m, 4H), 3-88-3.99 (m, 1H), 7.30 (d, 2H, J=8.4 Hz), 7.99 (d, 2H, J=8.4 Hz). $^{13}$C NMR (D$_2$O, 300 MHz) δ 30.62 (t), 35.04 (t), 49.49 (t), 50.33 (t), 50.93 (t), 56.57 (t), 62.53 (t), 64.79 (d), 123.68 (d), 129.30 (d), 145.91 (s), 149.75 (s), 162.51 (s). HRMS (positive ion ESI) Calcd for C$_{10}$H$_{31}$N$_4$O$_7$ [M+H]$^+$ m/z 439.2187. Found: [M+H]$^+$ m/z 439.2203. Analytical HPLC (t$_R$=7.4, method 1).

Tert-Butyl 2-{4-[2-(tert-butoxy)-2-oxoethyl]-7-(pyridin-2-ylmethyl)-1,4,7-triazonan-1-yl}acetate (11)

To a solution of 1 (50 mg, 0.140 mmol) in 1,2-dichloroethane (1 mL) was added 2-pyridinecarboxaldehyde (15 mg, 0.140 mmol). The resulted solution was stirred for 10 min and then added with sodium triacetoxyborohydride (44.5 mg, 0.210 mmol) portion-wise over 10 min. The mixture was stirred at room temperature for overnight. The reaction mixture was quenched by adding saturated NaHCO$_3$ (15 mL), and the resulting solution was extracted with ethyl acetate (3×15 mL). The combined organic layers were concentrated to dryness in vacuo. The residue was dissolved in 0.1M HCl solution (10 mL) and washed with CHCl$_3$ (2×10 mL). The aqueous layer was treated with saturated NaHCO$_3$ (10 mL) and extracted with ethyl acetate (3×20 mL). The combined organic layers were dried over MgSO$_4$, filtered, and concentrated in vacuo to provide pure 11 (60 mg, 96%) as a yellowish oil. $^1$H NMR (CDCl$_3$, 300 MHz) δ 1.44 (s, 18H), 2.72-3.04 (m, 12H), 3.31 (s, 4H), 3.87 (s, 2H), 7.13 (t, J=5.7 Hz, 1H), 7.54 (d, J=7.8 Hz, 1H), 7.63 (m, 1H), 8.50 (d, J=3.9 Hz, 1H); $^{13}$C NMR (CDCl$_3$, 300 MHz) δ 28.2 (q), 55.3 (t), 55.6 (t), 59.8 (t), 64.1 (t), 80.6 (s), 121.7 (d), 123.1 (d), 136.2 (d), 148.8 (d), 160.6 (s), 171.5 (s). HRMS (positive ion ESI) Calcd for C$_{24}$H$_{41}$N$_4$O$_4$ [M+H]$^+$ m/z 449.3122. Found: [M+H]$^+$ m/z 449.3118.

2-[4-(carboxymethyl)-7-(pyridin-2-ylmethyl)-1,4,7-triazonan-1-yl]acetic acid (E)

Compound 11 (16 mg, 0.036 mmol) was treated with 6M HCl solution (3 mL), and the resulting solution was refluxed for 5 h. The reaction mixture was gradually cooled to room temperature, filtered, and concentrated to dryness in vacuo to provide chelator E (15 mg, 86%) as a yellow solid. $^1$H NMR (D$_2$O, 300 MHz) δ 2.59-2.80 (m, 4H), 3.01 (t, J=5.7 Hz, 4H), 3.08 (s, 4H), 3.72 (s, 4H), 4.19 (s, 2H), 7.84 (t, J=7.2 Hz, 2H), 7.98 (d, J=7.8 Hz, 1H), 8.39 (dt, J=1.8 Hz, J=7.5 Hz, 1H), 8.51 (d, J=5.4 Hz, 1H). $^{13}$C NMR (D$_2$O, 300 MHz) δ 47.5 (t), 48.9 (t), 50.5 (t), 55.4 (t), 56.4 (t), 126.4 (d), 127.9 (d), 141.4 (d), 147.3 (d), 153.0 (s), 173.1 (s). HRMS (positive ion ESI) Calcd for C$_{16}$H$_{25}$N$_4$O$_4$ [M+H]$^+$ m/z 337.1870. Found: [M+H]$^+$ m/z 337.1863. Analytical HPLC (t$_R$=4.2, method 1).

Tert-Butyl 2-{4-[2-(tert-butoxy)-2-oxoethyl]-7-(thiophen-2-ylmethyl)-1,4,7-triazonan-1-yl}acetate (12)

To a solution of 1 (50.0 mg, 0.140 mmol) in 1,2-dichloroethane (1 mL) was added 2-thiophenecarboxaldehyde (15.7 mg, 0.140 mmol). The resulted solution was stirred for 10 min and treated with sodium triacetoxyborohydride (44.5 mg, 0.210 mmol) portion-wise over 10 min. The reaction mixture was stirred at room temperature for 3 d. The reaction mixture was quenched by adding saturated NaHCO$_3$ (15 mL), and the resulting solution was extracted with ethyl acetate (3×15 mL). The combined organic layer was concentrated in vacuo. The residue was treated with 0.1M HCl solution (10 mL) and extracted with CHCl$_3$ (3×10 mL). The combined organic layers were dried over MgSO$_4$, filtered, and the filtrate was concentrated to the dryness in vacuo. The residue was purified via column chromatography on silica gel (60-220 mesh) eluting with 15% $CH_3OH$ in $CH_2Cl_2$ to afford pure 12 (46 mg, 73%). $^1H$ NMR ($CDCl_3$, 300 MHz) δ 1.45 (s, 18H), 2.72-2.96 (m, 12H), 3.31 (s, 4H), 3.87 (s, 2H), 6.80-6.94 (m, 2H), 7.63 (dd, J=1.2 Hz, J=4.8 Hz, 1H); $^{13}C$ NMR ($CDCl_3$, 300 MHz) δ 28.2 (q), 55.0 (t), 55.2 (t), 55.3 (t), 56.8 (t), 59.9 (t), 80.7 (s), 124.6 (d), 125.3 (d), 126.3 (d), 160.6 (s), 171.5 (s). HRMS (positive ion ESI) Calcd for $C_{23}H_{40}N_3O_4S$ $[M+H]^+$ m/z 454.2734. Found: $[M+H]^+$ m/z 454.2723.

2-[4-(carboxymethyl)-7-(thiophen-2-ylmethyl)-1,4,7-triazonan-1-yl]acetic acid (F)

Compound 12 (17 mg, 0.037 mmol) at 0-5° C. was treated dropwise with 4M HCl (g) in 1,4-dioxane (2.5 mL) over 10 min. The resulting mixture was warmed to room temperature and stirred for 24 h. Diethyl ether (40 mL) was added to the mixture which was continued to stir for 10 min. The solid formed was filtered, washed with ether, and quickly dissolved in DI water. The aqueous solution was concentrated in vacuo to provide chelator F (13.5 mg, 80%) as a yellow solid. $^1H$ NMR ($D_2O$, 300 MHz) δ 2.90-3.61 (m, 13H), 3.70 (s, 4H), 3.73-3.89 (m, 1H), 6.91-7.08 (m, 1H), 7.27 (d, J=2.4 Hz, 1H), 7.49 (d, J=4.8 Hz, 1H). $^{13}C$ NMR ($D_2O$, 300 MHz) b 49.0 (t), 50.2 (t), 50.3 (t), 54.9 (t), 56.9 (t), 128.0 (d), 129.8 (s), 130.1 (d), 132.7 (d). HRMS (positive ion ESI) Calcd for $C_{15}H_{24}N_3O_4S$ $[M+H]^+$ m/z 342.1482. Found: $[M+H]^+$ m/z 342.1469. Analytical HPLC ($t_R$=5.8, method 1).

Preparation and Characterization of Cu(II) Complexes.

Cu(II)-complexes of the chelators A-F were prepared by reaction of each chelator (5 μl, 10 mM) with $CuCl_2$ (5 μl, 10 mM) in 0.25M $NH_4OAc$ buffer (pH 5.5) for 24 h at room temperature and 300 rpm. Each of Cu(II)-complex was purified by semi-prep HPLC (solvent A: 0.1% TFA in $H_2O$, solvent B: 0.1% TFA in $CH_3CN$, 0-60% B/40 min, flow rate: 3 mL/min). The purified Cu(II)-complex was characterized by analytical HPLC (method 1)

Determination of Maximum Specific Activity (MSA).

Whatman C18 silica gel TLC plates (KC18F, 60 Å) were purchased from Fisher Scientific (Pittsburgh, Pa.). Radio-TLCs were developed with 10% $NH_4OAc$:MeOH (3:7) and analyzed using a Bioscan 200 imaging scanner (Bioscan, Inc., Washington, D.C.). $^{64}CuCl_2$ was diluted with a 10-fold excess of 0.1M $NH_4OAc$ (pH 5.5) for radiolabeling. The maximum specific activities were determined experimentally via titrating $^{64}CuCl_2$ in 0.1M $NH_4OAc$ (pH 5.5) with the chelators. Briefly, for each chelator, six reaction vials were prepared in 0.1M $NH_4OAc$ (pH 5.5) via dilution to give final chelator masses in the range 0.001 to 0.1 μg. 3.7 MBq (100 μCi) of $^{64}Cu$ in 0.1 M $NH_4OAc$ (pH ~5.5) was added to each vial and adjusted the final volume to 100 μL (final pH 5.5) and vortexed for 10-15 seconds. The reactions were incubated on a rotator at 37° C. for 1 h. After incubation, 1 μL aliquots were withdrawn from reaction vials and analyzed by TLC (C-18) with a mixture of 10% $NH_4OAc$/MeOH (3:7) as a mobile phase for labeling percentage. All reactions were done in triplicate. The data were plotted as % labeling vs. amount of chelator reacted and the amount of mass required to achieve 50% labeling was then determined. This mass was then multiplied by 2 to obtain the minimal mass for 100% labeling and the maximum specific activity.

Complexation Formation Kinetics of Chelators with $^{64}Cu$.

All HCl solutions were prepared from ultra-pure HCl (Fisher Scientific, #A466-500). For metal-free radiolabeling, plasticware including pipette tips, tubes, and caps was soaked in 0.1M HCl (aq) overnight and washed thoroughly with Milli-Q (18 MΩ) water, and air-dried overnight. 0.25M $NH_4OAc$ buffer solution (pH 5.5) was prepared using ultrapure ammonium acetate (Aldrich, #372331) and pH of the solution was adjusted using 0.1M and 1M HCl solution. The resulting buffer solution was treated with Chelex-100 resin (Biorad, #142-2842, 1 g/100 ml buffer solution), shaken overnight at room temperature, and filtered through 0.22 μM filter (Corning, #430320) prior to use. TLC plates (6.6×1 cm or 6.6×2 cm, Silica gel 60 $F_{254}$, EMD Chemicals Inc., #5554-7) with the origin line drawn at 0.6 cm from the bottom were prepared. To a buffer solution (9~10 μL, 0.25M $NH_4OAc$, pH 5.5) in a capped microcentrifuge tube (1.5 mL, Fisher Scientific, #05-408-129) was sequentially added a solution of the chelator in the buffer (6.7 μL) and $^{64}Cu$ in 0.05M HCl (20 μCi, 3~4 μL). The total volume of the resulting solution was 20 μL. The reaction mixture was agitated on the thermomixer (Eppendorf, #022670549) set at 1,000 rpm at room temperature for 30 min. The labeling efficiency was determined by ITLC eluted with 20 mM EDTA in 0.15M $NH_4OAc$ as the mobile phase. A solution of radiolabeled complexes (2.0 μL) was withdrawn at the designated time points (1 min, 10 min, and 30 min), spotted on a TLC plate, and then eluted with the mobile phase. After completion of elution, the TLC plate was warmed and dried on the surface of a hot plate maintained at 3° C. and scanned using TLC scanner (Bioscan, #FC-1000). Unbound and bound radioisotope appeared 30~35 mm ($R_f$=0.5) and 50~55 mm ($R_f$=0.9) from the bottom of the TLC plate, respectively.

In Vitro Serum Stability of $^{64}Cu$-Radiolabeled Complexes.

Human serum was purchased from Gemini Bioproducts (#100110). $^{64}Cu$-radiolabeled complexes were prepared by reaction of the bifunctional chelators (30 μg) with $^{64}Cu$ (100 μCi) in 0.25M $NH_4OAc$ buffer (pH 5.5) for 1 h at room temperature, and labeling efficiency of the radiolabeled complexes were found to be ~100% as determined by ITLC (20 mM EDTA in 0.15M $NH_4OAc$). The freshly prepared radiolabeled complexes were directly used for serum stability studies without further purification. $^{64}Cu$-radiolabeled complex (85 μCi, 10 μL) was added to human serum (90 μL) in a microcentrifuge tube. The stability of $^{64}Cu$-radiolabeled complexes in human serum was evaluated at 37° C. for 2 days. A solution of the radiolabeled complex in serum was withdrawn at the designated time points and evaluated by ITLC as described above.

EDTA Challenge.

$^{64}Cu$-radiolabeled complexes were prepared by reaction of each chelator (20 μg) with $^{64}Cu$ (60 μCi) in 0.25M $NH_4OAc$ buffer (pH 5.5) for 2 h at room temperature. The radiolabeled complexes were prepared as described above and directly used for the experiments. $^{64}Cu$-radiolabeled complex was mixed with EDTA at a 100-fold molar excess. The resulting mixture was incubated for 24 h at 37° C. The stability of $^{64}Cu$-radiolabeled complexes in the solution was evaluated using ITLC (20 mM EDTA in 0.15M $NH_4OAc$). A solution of the radiolabeled complex in serum (3~20 μL) was withdrawn at the designated time points and evaluated by ITLC as described above. Stability of the complexes was also evaluated at 25 h time point by HPLC (solvent A: 0.1% TFA in $H_2O$, solvent B: 0.1% TFA in $CH_3CN$, 0-100% B/15 min, flow rate: 1 mL/min). $^{64}Cu$-EDTA complex was eluted early ($t_R$=~2.5 min), while $^{64}Cu$-radiolabeled complexes of chelators A-D, E, and F have the respective retention time ($t_R$=7~8 min, $t_R$=4.6 min, and $t_R$=6.2 min).

Chelation Chemistry of β-Emitting Radionuclides $^{90}$Y and $^{177}$Lu $^{90}$Y ($t_{1/2}$=2.7 days, $E_{max}$=2.3 MeV) and $^{177}$Lu ($t_{1/2}$=6.7 days, $E_{max}$=0.5 MeV) are β-emitting cytotoxic radionuclides for use in targeted radiation therapy of cancer. $^{90}$Y is a pure β-emitter with a high energy and long range of tissue penetration (~12 mm) that may be suitable for treatment of large solid tumors. A $^{90}$Y-radiolabeled antibody conjugate (Zevalin®) is clinically available for radioimmunotherapy (RIT) of B-cell non-Hodgkin's lymphoma. $^{177}$Lu possesses a shorter penetration range (~2 mm) and lower maximal energy relative to $^{90}$Y and has been proposed to selective target to small tumors while minimizing tissue damage. An imagable γ-ray of a low abundance emitted from $^{177}$Lu can be applied for a gamma scintigrapy during radiation therapy. An effective RIT using the radiolanthanides requires the use of an optimal bifunctional chelator that can form a metal complex with high thermodynamic stability and rapid radiolabeling kinetics under mild conditions. The radiolabeled complexes for RIT also must possess a high kinetic inertness to transchelation by metal cations and natural chelators present in vivo. Better understanding of chelation chemistry of Y(III) and Lu(III) can lead to a rational design and development of bifunctional chelators for potent and safe RIT applications using the radiolanthanides.

Figure 6:
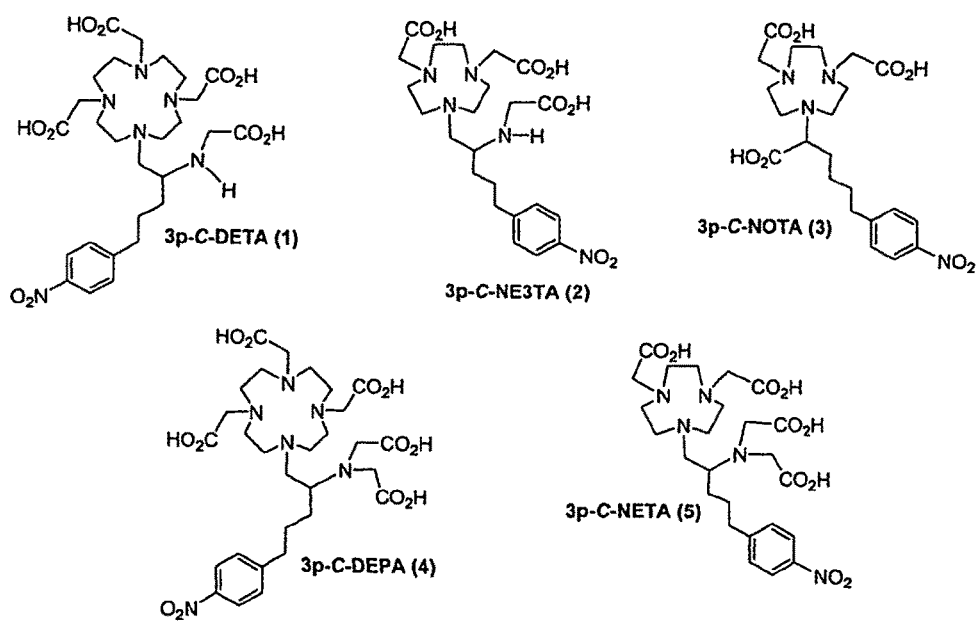
FIG. 6 illustrates backbones of chelators, such as are useful for targeted radioimmunotherapy, for example using $^{90}$Y and $^{117}$Lu, according to one embodiment of this invention.

The bifunctional chelators of FIG. 6, 3p-C-DETA (1) and 3p-C-NE3TA (2), and 3p-C-NOTA (3), were synthesized and evaluated as chelators for complexation with radiolanthanides $^{90}$Y and $^{177}$Lu. Nanodentate 3p-C-DETA (1) contains a 12-membered larger macrocyclic backbone, while heptadentate 3p-C-NE3TA (2) is structured on a smaller triazacyclononane (TACN) ring. Both 3p-C-DETA and 3p-C-NE3TA possess a less hindered bidentate acyclic pendant arm relative to 3p-C-DEPA (4) and 3p-C-NETA (5), respectively. Hexadentate 3p-C-NOTA (3) does not have the flexible pendant arm required for bimodal binding by cooperation of acyclic and macrocyclic binding moieties and was designed to compare the effect of bimodality on complexation with the radiolanthanides. The known bimodal chelators, decadentate 3p-C-DEPA (4) and octadentate 3p-C-NETA (5) were also evaluated for complexation with $^{90}$Y and $^{177}$Lu for comparison. The comparative evaluation of the bimodal chelators with the structural variations is expected to advance our understanding on effect of the coordination factors including bimodality, denticity, and macrocyclic cavity on complexation of the bimodal chelators with the β-emitting radiolanthanides.

Results and Discussion

Synthesis.

Figure 7:
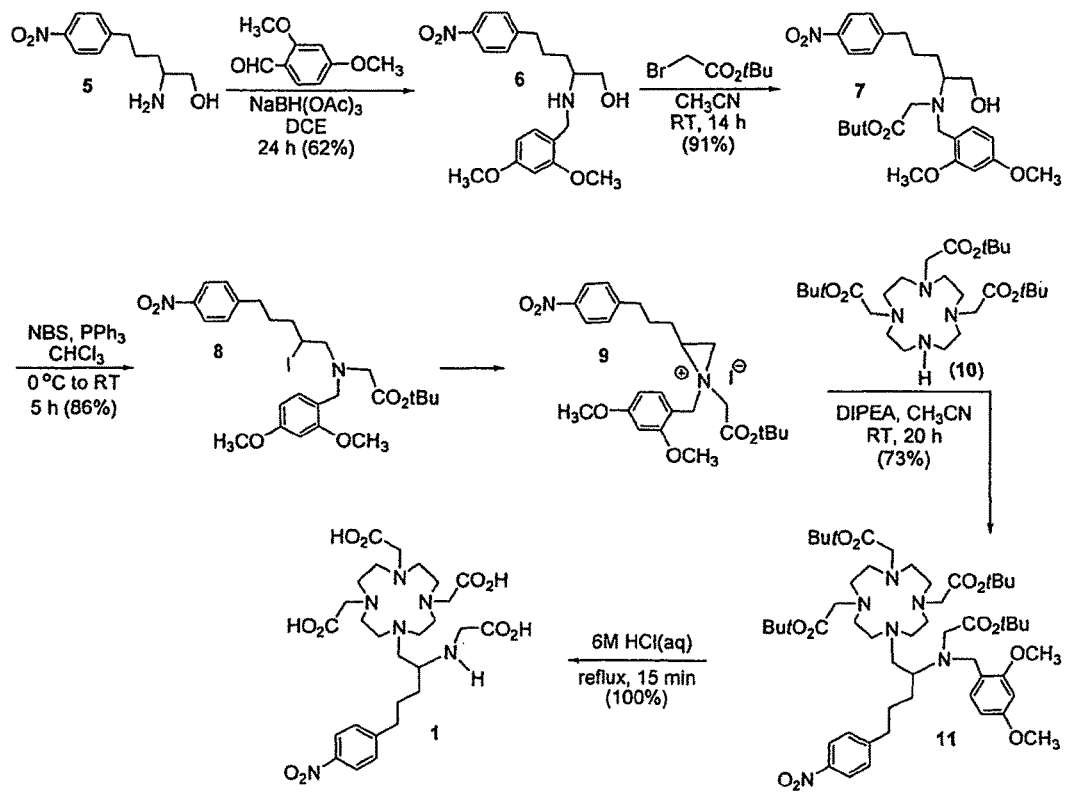
FIG. 7 is a reaction scheme of chelator 3p-C-DETA (1), according to one embodiment of this invention.
Figure 8:
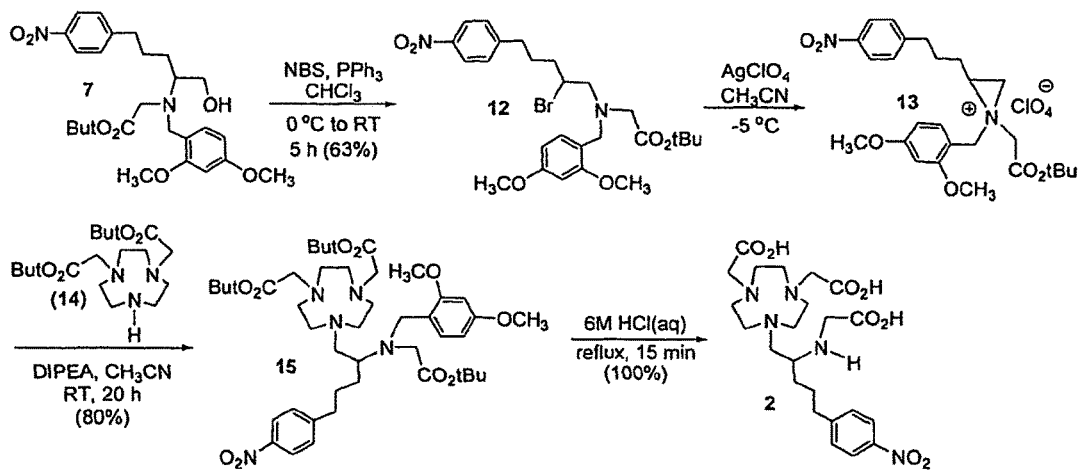
FIG. 8 is a reaction scheme of chelator 3p-C-NE3TA (2), according to one embodiment of this invention.
Figure 9:
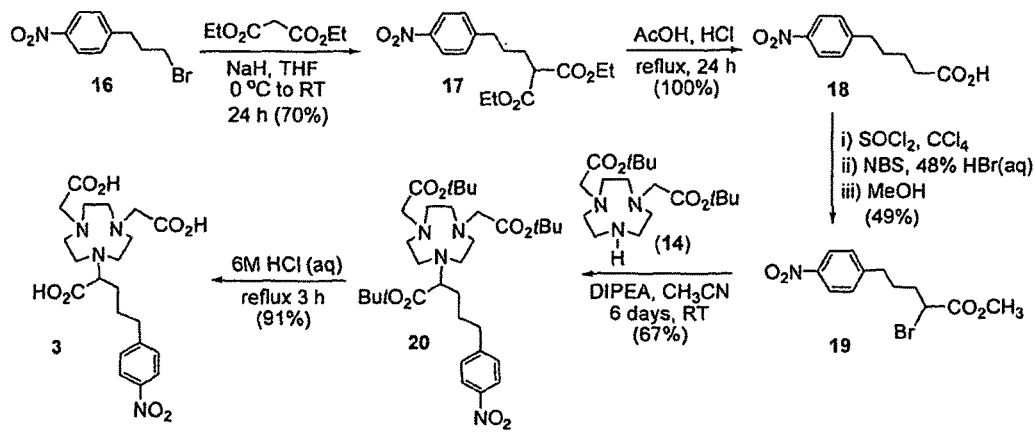
FIG. 9 is a reaction scheme of chelator 3p-C-NOTA (3), according to one embodiment of this invention.

The chelators 3p-C-DETA (1) and 3p-C-NE3TA (2) as shown in FIGS. 7 and 8 were prepared based on the regiospecific ring opening of labile aziridinium ions (9 and 13) with the pre-alkylated CYCLEN (1,4,7,10-tetraazacyclododecane, 10) and TACN (1,4,7-triazacyclononane, 14). Synthesis of 3p-C-DETA is outlined in FIG. 7. Reductive amination of amino alcohol 5 with dimethoxybenzaldehyde provided N-dimethoxybenzyl (DMB) protected compound 6 which was further alkylated to afford bi-substituted amino alcohol 7. Halogenation of 7 using $I_2$ and $PPh_3$ afforded secondary p-amino iodide 8. Conversion of 8 to aziridinium ion 9 followed by nucleophilic reaction of 9 with trialkylated macrocyclic cyclen 10 at the less hindered carbon provided the desired ring opening product 11 as the regiospecific isomer. Subsequent removal of the tert-butyl and DMB groups in 11 by treatment of 11 with 6M HCl(aq) under reflux provided 3p-C-DETA (1) in quantitative yield. Synthesis of 3p-C-NE3TA (2) is outlined in FIG. 8. Reaction of 7 with brominating agent (NBS and $PPh_3$) afforded secondary (3-amino bromide 12. Intramolecular rearrangement of β-bromoamine 12 to aziridinium ion 13 was promoted by halogen sequestering agent ($AgClO_4$). Reaction of bisubstituted TACN 14 with the alkylating agent 13 provided the nucleophilic ring opening product 15 as the regiospecific isomer. Compound 15 was subjected to acidic hydrolysis using HCl(aq) for removal of the protective tert-butyl groups in 15. Synthesis of 3p-C-NOTA is shown in FIG. 9. A base-promoted reaction of p-nitrophenylpropyl bromide (16) with diethyl malonate provided compound 17 which was subsequently subjected to deprotective hydrolysis to afford a functionalized carboxylic acid 18. Chlorination of 18 followed by α-bromination and esterification afforded α-bromomethyl ester 19. Subsequent reaction of 19 with bisubstituted TACN 14 provided compound 20 which was treated with 6M HCl(aq) to produce 3p-C-NOTA (3).

Radiolabeling Kinetics and In Vitro Serum Stability.

The bifunctional chelators 3p-C-DETA (1), 3p-C-NE3TA (2), 3p-C-NOTA (3), and 3p-C-DEPA (4) were evaluated for radiolabeling efficiency with $^{90}$Y and $^{177}$Lu (Tables 4 and 5). A chelator (30 μg) in 0.25M $NH_4OAc$ buffer solution was radiolabeled with $^{90}$Y or $^{177}$Lu (60 μCi) at room temperature (RT). During the reaction time (1 h), the radiolabeling kinetics was determined using ITLC. Radiolabeling of nanodentate 3p-C-DETA (1) with $^{90}$Y or $^{177}$Lu was nearly complete at 10 min time point (>99% radiolabeling efficiency, pH 7). It should be noted that 3p-C-DETA (2) was very slow in binding both $^{90}$Y and $^{177}$Lu at pH 5.5 (1 min, 7% and 21% radiolabeling efficiency for $^{90}$Y and $^{177}$Lu, respectively). It was speculated that the protonated secondary amine in the chelator may not participate in complexation under acidic condition and lead to slow radiolabeling of the chelator. A dramatic increase in radiolabeling kinetics was observed when 3p-C-DETA (1) was subjected to radiolabeling at pH 7 (1 min, >85% radiolabeling efficiency for $^{90}$Y and $^{177}$Lu). Both 3p-C-NE3TA (2) and 3p-C-NOTA (3) were more sluggish in binding $^{90}$Y than $^{177}$Lu. 3p-C-NE3TA and 3p-C-NOTA bound to $^{90}$Y with the respective radiolabeling efficiencies of 84% and 69% at the 1 h time point, while radiolabeling of 3p-C-NE3TA and 3p-C-NOTA with the smaller metal cation $^{177}$Lu was nearly complete at 1 h time point. When compared to 3p-C-NETA (5) with the same macrocyclic cavity, 3p-C-NE3TA (2) and 3p-C-NOTA (3) were significantly slower in binding $^{90}$Y and $^{177}$Lu. This result clearly demonstrates that the tridentate acyclic moiety is critical in enhancing complexation kinetics via bimodal binding. It was interesting to note that the hexadentate 3p-C-NOTA was more efficient in binding both $^{90}$Y and $^{177}$Lu than 3p-C-NE3TA, although hexadentate 3p-C-NOTA has an insufficient number of donor groups for complex with the large metal cations. The data seems to support that 3p-C-NOTA can rapidly complex $^{90}$Y or $^{177}$Lu in a 2:1 (ligand:metal) ratio. Decadendate 3p-C-DEPA (4) rapidly sequestered $^{90}$Y and $^{177}$Lu with the respective radiolabeling efficiency of 89% and 94% at 1 min time point. 3p-C-DETA (1) and 3p-C-DEPA (4) with the same macrocyclic cavity displayed similar complexation kinetics with the metals.

TABLE 4

Radiolabeling efficiency (%) of chelators with $^{90}$Y (pH 5.5, RT)#

| Time (min) | 3p-C-DETA* (1) | 3p-C-NE3TA‡ (2) | 3p-C-NOTA‡ (3) | 3p-C-DEPA (4) | 3p-C-NETA+ (5) |
|---|---|---|---|---|---|
| 1  | 88.4 ± 1.9  | 3.1 ± 0.28  | 10.3 ± 0.6 | 89.3 ± 2.8 | 97.4 ± 0.7 |
| 10 | 99.2 ± 0.58 | 22.5 ± 0.28 | 50.8 ± 1.8 | 96.8 ± 0.5 | 98.7 ± 1.6 |
| 20 | 99.3 ± 0.61 | 37.6 ± 0.64 | 73.9 ± 0.6 | 98.0 ± 0.9 | 98.7 ± 2.2 |
| 30 | 99.2 ± 0.72 | 49.1 ± 1.6  | 82.7 ± 0.4 | 97.9 ± 0.2 | 99.4 ± 0.9 |
| 60 | 99.5 ± 0.49 | 68.7 ± 3.4  | 89.3 ± 0.1 | 98.5 ± 0.2 | 99.5 ± 1.0 |

Radiolabeling efficiency (mean ± standard deviation %) was measured in triplicate using ITLC.
*Radiolabeling efficiency was determined at pH 7 using ITLC.
‡Duplicate run
+The data were cited for comparison.

TABLE 5

Radiolabeling efficiency (%) of chelators with $^{177}$Lu (pH 5.5, RT)#

| Time (min) | 3p-C-DETA* (1) | 3p-C-NE3TA (2) | 3p-C-NOTA (3) | 3p-C-DEPA (4) | 3p-C-NETA+ (5) |
|---|---|---|---|---|---|
| 1  | 85.2 ± 0.7  | 6.7 ± 0.1  | 17.5 ± 0.5 | 93.9 ± 1.3 | 100.0 ± 0.0 |
| 10 | 99.8 ± 0.3  | 36.6 ± 0.4 | 81.3 ± 0.2 | 98.7 ± 0.2 | 100.0 ± 0.0 |
| 20 | 99.8 ± 0.1  | 63.2 ± 0.8 | 95.0 ± 0.2 | 99.2 ± 0.3 | 100.0 ± 0.0 |
| 30 | 99.9 ± 0.1  | 78.1 ± 1.1 | 99.1 ± 0.4 | 99.4 ± 0.1 | 100.0 ± 0.0 |
| 60 | 100.0 ± 0.1 | 95.0 ± 0.1 | 100 ± 0.1  | 99.3 ± 0.2 | 100.0 ± 0.0 |

Radiolabeling efficiency (mean ± standard deviation %) was measured in triplicate using ITLC.
*Radiolabeling efficiency was determined at pH 7 using ITLC.
+The data cited for comparison.

Figure 10:
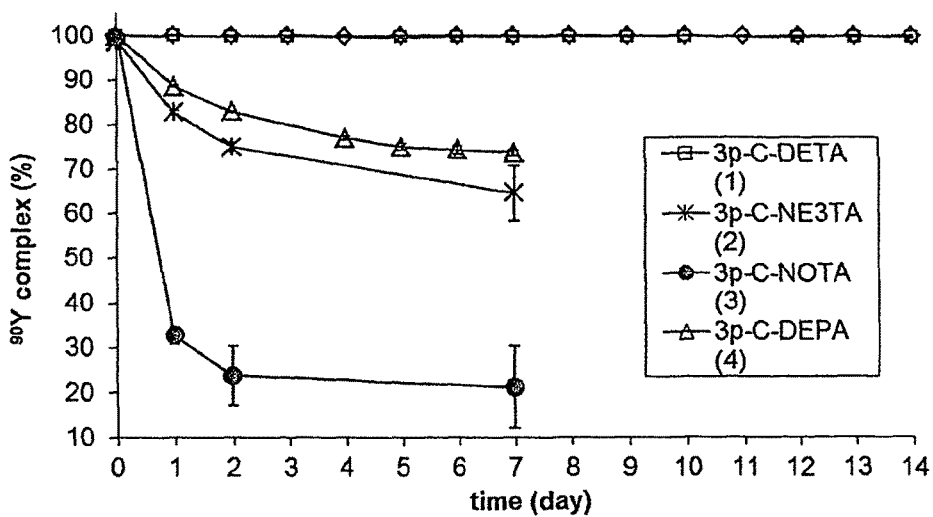
FIG. 10 is a plot summarizing in vitro serum stability of $^{90}$Y-radiolabeled complexes.
Figure 11:
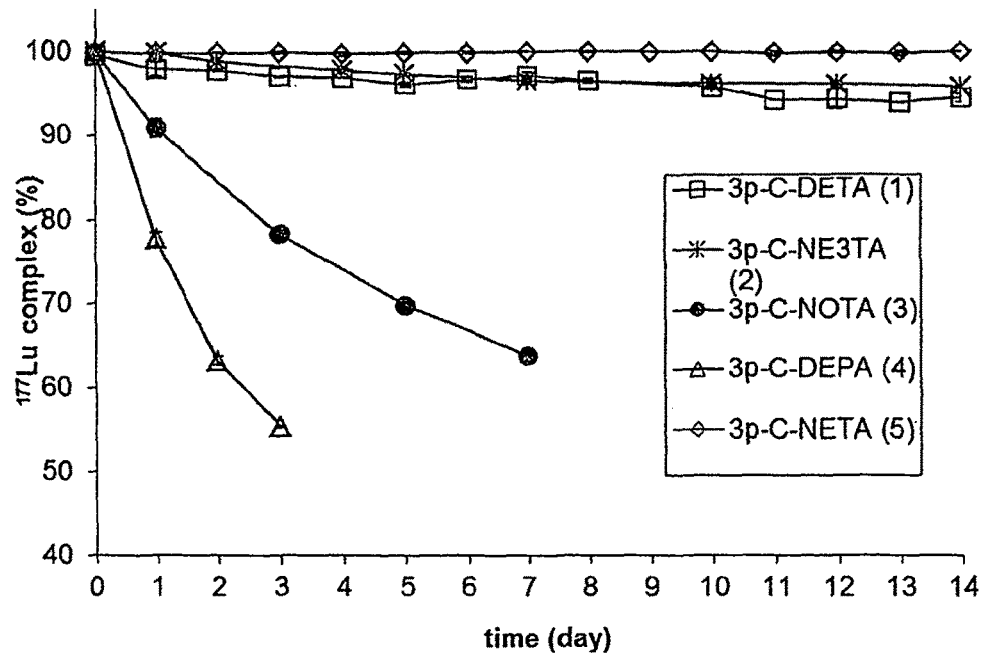
FIG. 11 is a plot summarizing in vitro serum stability of $^{177}$Lu-radiolabeled complexes.

$^{90}$Y- or $^{177}$Lu-radiolabeled chelators were further evaluated for in vitro serum stability (n=2, FIGS. 10 and 11). $^{90}$Y-3p-C-DETA (1) was found to be stable in serum for at least for 2 weeks, while a small amount of $^{177}$Lu (~5%) was lost from $^{177}$Lu-3p-C-DETA (1) over 2 weeks. A significant amount of the radioactivity from both $^{90}$Y-3p-C-DEPA (4) and $^{177}$Lu-3p-C-DEPA (4) was transchelated to serum (25% and 40% in 72 h, respectively). As expected, both $^{90}$Y and $^{177}$Lu complexes of 3p-C-NOTA (4) were not stable in serum, and ~80% of $^{90}$Y and ~36% of $^{177}$Lu released from the complexes on day 7. It appears that this result supports the complexation of the hexadentate chelator with $^{90}$Y and $^{177}$Lu in a 2:1 ratio, and the NOTA chelator rapidly can form a kinetically labile complex that is instantly dissociated in serum. $^{177}$Lu-3p-C-NE3TA (3) remained quite stable in serum, and only ~4% of the radioactivity was transferred from the complex to serum. However, $^{90}$Y-3p-C-NE3TA underwent rapid dissociation, losing ~25% of $^{90}$Y to serum in 3 days. It appears that 3p-C-NE3TA failed to tightly hold the larger metal, $^{90}$Y due to an insufficient number of donors, while the heptadentate chelator can form a complex with the smaller metal $^{177}$Lu with enhanced complex stability.

The radiolabeling and serum stability data indicate that the decadentate chelator 3p-C-DEPA (3) instantly bound to $^{90}$Y and $^{177}$Lu, but failed to hold $^{90}$Y or $^{177}$Lu in serum. It seems that the DEPA built on the larger macrocyclic cavity has too many donor groups to form a stable complex with the relatively smaller metal cations Y(III) and Lu(III), and this excessive ligand denticity may promote formation and dissociation of the Lu(III)- or Y(III)-DEPA complex in equilibrium. It should be noted that nanodentate DETA and decadentate DEPA are structured on the same cyclen-based ring and display completely different complex stability with Y(III) and Lu(III). The comparative data of 3p-C-DETA (1) and 3p-C-DEPA (4) suggest that the denticity in the chelators with the large macrocyclic cavity plays a critical role in complexation. No substantial difference in complexation of $^{90}$Y between 3p-C-DETA (1) and 3p-C-NETA (5), the standard gold chelator, was observed. It appears that the nine donor groups on the large cyclen ring of the DETA were well tolerated to complex with $^{90}$Y with high complexation kinetics and stability. The slightly enhanced complex stability observed with $^{90}$Y-3p-C-DETA relative to $^{177}$Lu-3p-C-DETA may be explained by a better size-match between the cavity and the larger metal Y(III) that is well balanced with the nine donor groups. The 12 membered ring may be too large to hold smaller Lu(III) with high complex stability. The effect of the size-match was also demonstrated from evaluation of 3p-C-NE3TA (3) and 3p-C-NOTA (4). The NE3TA chelator with the small cavity, was completely ineffective in complexing the larger metal cation Y(III) with high stability, while Lu(III) was quite tightly chelated with the NE3TA chelator. It is demonstrated that 3p-C-NOTA (5) was incapable of chelating the lanthanides effectively due to the poor size match. It is noteworthy that replacement of the bidentate amiocaroxylate group in the NOTA with a more flexible tridentate group led to enhanced complex stability with $^{177}$Lu as shown in complexation of the NE3TA. This result clearly demonstrate that the pendant acyclic donors are essential in effective complexation with the metals, and the improved complexation kinetics and stability of other bimodal chelators as compared to the NOTA, predominantly resulted from cooperative and bimodal binding of acyclic and macrocyclic donors.

In summary, the chelators 3p-C-DETA (1), 3p-C-NE3TA (2), 3p-C-NOTA (3) were prepared and complexed with $^{90}$Y and $^{177}$Lu for compared to the known chelators 3p-C-DEPA (4) and 3p-C-NETA (5). It was shown that radiolabeling of the chelators $^{90}$Y and $^{177}$Lu can be optimized to rapidly produce the radiolabeled complexes at room temperature but the radiolabeled complexes possess different complex stability in serum. The serum stability data indicate that $^{90}$Y and $^{177}$Lu-radiolabeled complexes of nanodentate 3p-C-DETA (1) displayed excellent to good complex stability in serum. Hexadentate 3p-C-NOTA (3) and decadentate 3p-C-DEPA (4) were incapable of producing a stable complex with $^{90}$Y and $^{177}$Lu, and a significant amount of the radionuclide was instantly transchelated to serum. $^{177}$Lu-3p-C-NE3TA (2) remained quite inert in serum, while $^{90}$Y-3p-C-NE3TA (2) was rapidly dissociated in serum. The results of the comparative complexation kinetic and stability studies indicate that bimodality, cavity size, and ligand denticity have an impact on complexation of the bifunctional chelators with the radiolanthanides, and a well-coordinated interplay of the factors is critical for the dynamic and tight binding of the bifunctional chelators with $^{90}$Y and $^{177}$Lu. The bimodal chelators 3p-C-DETA and 3p-C-NE3TA therefore possess potential for use in targeted radiotherapeutic applications using $^{90}$Y or $^{177}$Lu.

Experimental Section $^{1}$H, $^{13}$C, and DEPT NMR spectra were obtained using a Bruker 300 instrument and chemical shifts are reported in parts per million (ppm) on the δ scale relative to TMS. Electrospray (ESI) high-resolution mass spectra (HRMS) were obtained on JEOL double sector JMS-AX505HA mass spectrometer (University of Notre Dame, South Bend, Ind.). The analytical HPLC was performed on an Agilent 1200 equipped with a dioarray detector (λ=254 and 280 nm), themostat set at 35° C., and a Zorbax Eclipse XDB-C18 column (4.6×150 mm, 80 Å). The mobile phase of a binary gradient (0-100% B/40 min; solvent A, 0.05 M AcOH/Et$_3$N, pH 6.0; solvent B, CH$_3$OH for method 1) at a flow rate of 1 mL/min was used. Semi-preparative HPLC was performed on an Agilent 1200 equipped with a dioarray detector (λ=254 and 280 nm), thermostat set at 35° C., and a Zorbax Eclipse XDB-C18 column (9.4×250 mm, 80 Å). The mobile phase of a binary gradient (0-100% B/160 min; solvent A, 0.05 M AcOH/Et$_3$N, pH 6.0; solvent B, CH$_3$OH for method 2; 0-100% B/80 min; solvent A, 0.05 M AcOH/Et$_3$N, pH 6.0; solvent B, CH$_3$OH for method 3) at a flow rate of 3 mL/min was used. $^{90}$Y (0.05M HCl) and $^{177}$Lu (0.05M HCl) were purchased from Perkin Elmer.

2-{[(2,4-dimethoxyphenyl)methyl]amino}-5-(4-nitrophenyl)pentan-1-ol (6)

To a stirred solution of 5 (1.60 g, 7.13 mmol) in 1,2-dichloroethane (40 mL) was added 2,4-dimethoxy-benzaldehyde (1.19 g, 7.13 mmol) The resulted solution was stirred for 10 min and then added with sodium triacetoxyborohydride (2.12 g, 9.99 mmol) portionwise over 10 min. The mixture was stirred at room temperature for 1 d. The reaction mixture was quenched by saturated NaHCO$_3$ (100 mL) and the resulting solution was extracted with EA (3×60 mL). The combined organic layer was concentrated in vacuo. The residue was purified by silica gel (60-230 mesh) column chromatography eluted with 10% CH$_3$OH in CH$_2$C$_2$ to afford 6 (1.65 g, 62%). $^{1}$H NMR (CDCl$_3$, 300 MHz) δ 1.41-1.53 (m, 2H), 1.55-1.73 (m, 2H), 2.45 (broad, 2H), 2.59-2.76 (m, 3H), 3.32 (dd, J=10.8, 5.4 Hz, 1H), 3.59-3.85 (m, 9H), 6.34-6.49 (m, 2H), 7.07 (d, J=7.8 Hz, 1H), 7.27 (d, J=8.7 Hz, 2H), 8.10 (d, J=8.7 Hz, 2H); $^{13}$C NMR (CDCl$_3$, 300 MHz) δ 27.3 (t), 31.3 (t), 35.6 (t), 46.1 (t), 55.3 (q), 55.4 (q), 57.4 (d), 62.7 (t), 98.7 (d), 103.9 (d), 120.5 (s), 123.6 (d), 129.1 (d), 130.5 (d), 146.4 (s), 150.1 (s), 158.6 (s), 160.4 (s). HRMS (Positive ion ESI) Calcd for C$_{20}$H$_{27}$N$_2$O$_5$ [M+H]$^+$ m/z 375.1914. Found: [M+H]$^+$ m/z 375.1886.

Tert-Butyl 2-{[(2,4-dimethoxyphenyl)methyl][1-hydroxy-5-(4-nitrophenyl)pentan-2-yl]amino}acetate (7)

To a stirred solution of 6 (1.60 g, 4.27 mmol) in CH$_3$CN (30 mL) at 0° C. was added K$_2$CO$_3$ (0.62 g, 4.49 mmol). A solution of t-butyl bromoacetate (0.88 g, 4.49 mmol) in CH$_3$CN (10 mL) was added dropwise to the resulting mixture over 10 min. The reaction mixture was stirred for at room temperature for 2 days while the reaction progress was continuously monitored using TLC. The reaction mixture was filtered and evaporated in vacuo to provide 7 (1.21 g, 91%) as a light yellow oil. The product was directly used for the next step without further purification. $^{1}$H NMR (CDCl$_3$, 300 MHz) δ 1.36 (s, 9H), 1.55-1.73 (m, 4H), 2.71 (d, J=7.5 Hz, 2H), 2.80-2.94 (m, 1H), 3.19 (dd, J=30.3, 17.1 Hz, 2H), 3.33 (d, J=10.8 Hz, 1H), 3.50 (dd, J=10.8, 4.2 Hz, 1H), 3.63-3.85 (m, 8H), 4.05-4.16 (m, 1H), 6.35-6.46 (m, 2H), 7.15 (d, J=8.7 Hz, 1H), 7.31 (d, J=8.7 Hz, 2H), 8.15 (d, J=8.7 Hz, 2H); $^{13}$C NMR (CDCl$_3$, 300 MHz) b 27.0 (t), 28.0 (q), 28.4 (t), 36.0 (t), 49.5 (t), 52.2 (t), 55.2 (q), 55.3 (q), 62.1 (t), 63.4 (d), 81.0 (s), 98.5 (d), 104.0 (d), 119.2 (s), 123.7 (d), 129.1 (d), 131.5 (d), 146.5 (s), 149.9 (s), 158.9 (s), 160.4 (s), 172.3 (s). HRMS (Positive ion ESI) Calcd for C$_{26}$H$_{37}$N$_2$O$_7$ [M+H]$^+$ m/z 489.2595. Found: [M+H]$^+$ m/z 489.2577.

tert-butyl-2-{[(2,4-dimethoxyphenyl)methyl][2-iodo-5-(4-nitrophenyl)pentyl]amino}acetate (8)

To a solution of 7 (100 mg, 0.205 mmol) and PPh$_3$ (64.42 mg, 0.246 mmol) in CHCl$_3$ (5 mL) at 0° C. was added portionwise 12 (62.34 mg, 0.246 mmol) over 5 min and imidazole (16.75 mg, 0.246 mmol). The resulting mixture was stirred for 5 h at room temperature. The solvent was evaporated and the residue was purified by silica gel column chromatography eluted with 5% EtOAc in hexanes to afford pure 8 (97.4 mg, 86%) as a light yellow oil. Compound 8 was directly used for the next step. $^{1}$H NMR (CDCl$_3$, 300 MHz) δ 1.46 (s, 9H), 1.71 (s, 2H), 1.91-1.96 (m, 2H), 2.69-2.71 (m, 2H), 2.96 (m, 1H), 3.23 (s, 3H), 3.77 (dd, J=6.3 Hz, 8H), 6.43 (s, 2H), 7.16 (d, J=8.1 Hz, 1H), 7.31 (d, J=7.5 Hz, 2H), 8.11 (d, J=7.8 Hz, 2H); $^{13}$C NMR (CDCl$_3$, 300 MHz) δ 28.3 (q), 30.6 (t), 34.9 (t), 36.2 (t), 37.0 (q), 51.7 (d), 55.4 (q), 55.8 (t), 63.5 (t), 80.9 (s), 98.4 (d), 103.9 (d), 119.1 (s), 123.6 (d), 129.2 (d), 131.2 (d), 146.3 (s), 150.0 (s), 158.8 (s), 160.2 (s), 170.9 (s).

Tert-Butyl 2-{[(2,4-dimethoxyphenyl)methyl][5-(4-nitrophenyl)-1-{4,7,10-tris[2-(tert-butoxy)-2-oxo-ethyl]-1,4,7,10-tetraazacyclododecan-1-yl}pentan-2-yl]amino}acetate (11)

To a solution of 8 (50 mg, 0.0907 mmol) in CH$_3$CN (5 mL) at 0° C. was added compound 10 (46.66 mg, 0.0907 mmol) and DIPEA (23.43 mg, 0.181 mmol). The resulting mixture was stirred for 4 d at room temperature, while monitoring the reaction progress using TLC. The reaction mixture was concentrated to dryness. The residue was washed by using 0.1 M HCl (10 mL) and 0.1 M NaOH (10 mL) sequentially. The resulting residue was concentrated to dryness to provide pure 11 (65.4 mg, 73%). $^1$H NMR (CDCl$_3$, 300 MHz) δ 1.29-1.48 (m, 36H), 1.50-2.09 (m, 4H), 2.61-3.93 (m, 37H), 6.34-6.52 (m, 2H), 7.17-7.26 (m, 1H), 7.40 (d, J=8.7 Hz, 2H), 8.06-8.17 (m, 2H). $^{13}$C NMR (CDCl$_3$, 300 MHz) δ 28.1 (q), 28.2 (t), 30.6 (t), 35.8 (t), 47.2 (t), 51.9 (d), 52.0 (t), 53.0 (s), 55.2 (q), 56.4 (t), 56.9 (t), 57.8 (d), 80.6 (s), 98.0 (d), 104.0 (d), 120.4 (s), 123.4 (d), 129.3 (d), 130.6 (d), 146.1 (s), 151.3 (s), 158.5 (s), 159.6 (s), 171.1 (s), 171.9 (s). HRMS (Positive ion ESI) Calcd for C$_{52}$H$_{85}$N$_6$O$_{12}$ [M+H]$^+$ m/z 985.6220. Found: [M+H]$^+$ m/z 985.6224.

2-{[5-(4-nitrophenyl)-1-[4,7,10-tris(carboxymethyl)-1,4,7,10-tetraazacyclododecan-1-yl]pentan-2-yl]amino}acetic acid (1)

To compound 11 (27 mg, 0.0274 mmol) was added 6M HCl solution (3 mL), and the resulting solution was maintained at reflux for 15 min. The reaction was allowed to room temperature, and the resulting solution was filtered and dried in vacuo to provide compound 1 (22 mg, 100%) as a yellow solid. $^1$H NMR (D$_2$O, 300 MHz) δ 1.32-1.81 (m, 4H), 2.38-4.11 (m, 29H), 7.32 (t, J=8.1 Hz, 2H), 8.05 (d, J=8.1 Hz, 1H). $^{13}$C NMR (D$_2$O, 75 MHz) 25.5 (t), 27.8 (t), 34.3 (t), 45.2 (t), 49.1 (t), 49.8 (t), 50.9 (t), 52.4 (t), 52.7 (t), 54.2 (t), 54.8 (d), 55.7 (t), 123.6 (d), 129.4 (d), 145.8 (s), 150.0 (s), 168.9 (s). HRMS (Negative ion ESI) Calcd for C$_{27}$H$_{41}$N$_6$O$_{10}$ [M−H]$^−$ m/z 609.2890. Found: [M−H]$^−$ m/z 609.2926.

tert-butyl-2-{[2-bromo-5-(4-nitrophenyl)pentyl][(2,4-dimethoxyphenyl)methyl]-amino}acetate (12)

To a solution of 7 (300 mg, 0.614 mmol) and PPh$_3$ (193 mg, 0.737 mmol) in CHCl$_3$ (5 mL) at 0° C. was added portion-wise NBS (131 mg, 0.737 mmol) over 5 min. The resulting mixture was stirred for 4 h while being maintained at 0° C. The ice bath was removed, and the reaction mixture was warmed to room temperature and stirred for 1 h. The solvent was evaporated, and the residue was purified by silica gel column chromatography eluted with 10% ethyl acetate in hexanes to afford 12 (210 mg, 63%) as a yellow oil. $^1$H NMR (CDCl$_3$, 300 MHz) δ 1.46 (s, 9H), 1.62-2.17 (m, 4H), 2.60-2.81 (m, 2H), 2.96 (dd, J=13.8, 8.7 Hz, 1H), 3.17 (dd, J=13.8, 5.4 Hz, 1H), 3.24 (s, 2H), 3.66-3.95 (m, 9H), 3.94-4.12 (m, 1H), 6.44-6.49 (m, 2H), 7.20 (d, J=8.7 Hz, 1H), 7.33 (d, J=8.7 Hz, 2H), 8.13 (d, J=8.7 Hz, 2H); $^{13}$C NMR (CDCl$_3$, 75 MHz) δ 28.2 (q), 28.5 (t), 35.1 (t), 35.2 (t), 51.9 (t), 55.1 (d), 55.3 (q), 56.1 (t), 61.8 (t), 80.9 (s), 98.4 (d), 103.9 (d), 119.1 (s), 123.6 (d), 129.2 (d), 131.2 (d), 146.3 (s), 150.0 (s), 158.8 (s), 160.2 (s), 170.9 (s). HRMS (Positive ion ESI) Calcd for C$_{26}$H$_{35}$N$_2$O$_6$ [M−Br]$^+$ m/z 471.2490. Found: [M−Br]$^+$ m/z 471.2474.

Tert-Butyl 2-[(1-{4,7-bis[2-(tert-butoxy)-2-oxo-ethyl]-1,4,7-triazonan-1-yl}-5-(4-nitrophenyl)pentan-2-yl)[(2,4-dimethoxyphenyl)methyl]amino]acetate (15)

To a solution of 12 (50 mg, 0.0907 mmol) in CH$_3$CN (1 mL) at −5° C. was added AgClO$_4$ (18.8 mg, 0.0907 mmol). The resulting mixture was stirred for 10 min at the same temperature. Compound 14 (32.4 mg, 0.0907 mmol) and DIPEA (35.2 mg, 0.272 mmol) was sequentially added to the reaction mixture at −5° C. The resulting mixture was gradually warmed to room temperature and stirred for 20 h. The reaction mixture was filtered and concentrated to the dryness. 0.1M HCl solution (10 mL) was added to the residue, and the resulting mixture was extracted with CH$_2$Cl$_2$ (3×10 mL). The combined organic layers were dried over MgSO$_4$, filtered, and concentrated in vacuo. The residue was purified via column chromatography on silica gel (60-220 mesh). The column was first eluted with 50% ethyl acetate in hexanes, then dried and eluted with 3% CH$_3$OH in CH$_2$Cl$_2$ to provide pure product 15 (70 mg, 80%) as a yellowish oil. $^1$H NMR (CDCl$_3$, 300 MHz) δ 1.29-1.48 (m, 27H), 1.50-2.09 (m, 4H), 2.61-3.93 (m, 31H), 6.34-6.52 (m, 2H), 7.07 (d, J=8.1 Hz, 1H), 7.37 (d, J=8.7 Hz, 2H), 8.10 (d, J=8.7 Hz, 2H). $^{13}$C NMR (CDCl$_3$, 75 MHz) δ 27.1 (t), 28.0 (q), 28.1 (q), 28.3 (t), 35.8 (t), 50.5 (t), 51.1 (t), 51.5 (t), 53.5 (t), 54.0 (t), 55.4 (q), 56.8 (d), 57.1 (t), 58.5 (t), 58.7 (t), 81.5 (s), 81.6 (s), 82.2 (s), 98.6 (d), 104.5 (d), 117.7 (s), 123.6 (d), 129.4 (d), 131.9 (d), 146.3 (s), 149.9 (s), 158.8 (s), 160.8 (s), 170.5 (s), 170.7 (s), 173.1 (s). HRMS (Positive ion ESI) Calcd for C$_{44}$H$_{70}$N$_5$O$_{10}$ [M+H]$^+$ m/z 828.5117. Found: [M+H]$^+$ m/z 828.5161.

2-({1-[4,7-bis(carboxymethyl)-1,4,7-triazonan-1-yl]-5-(4-nitrophenyl)pentan-2-yl}amino)acetic acid (2)

To compound 15 (30 mg, 0.0362 mmol) was added 6M HCl solution (3 mL), and the resulting solution was maintained at reflux for 15 min. The reaction was allowed to room temperature, and the resulting solution was filtered and dried in vacuo to provide the desired chelator 2 (25 mg, 100%) as a yellow solid. $^1$H NMR (D$_2$O, 300 MHz) δ 1.22-1.73 (m, 4H), 2.34-3.36 (m, 17H), 3.67-3.91 (m, 6H), 7.18 (t, J=6.3 Hz, 2H), 7.87 (d, J=6.3 Hz, 1H). $^{13}$C NMR (D$_2$O, 75 MHz) δ 25.4 (t), 27.2 (t), 34.3 (t), 44.3 (t), 49.4 (t), 49.9 (t), 51.7 (t), 55.2 (t), 56.3 (t), 58.4 (t), 123.6 (d), 129.3 (d), 145.8 (s), 150.0 (s), 168.7 (s), 170.7 (s). HRMS (Positive ion FAB) Calcd for C$_{23}$H$_{36}$N$_5$O$_8$: [M+H]$^+$ m/z 510.2558. Found: [M+H]$^+$ m/z 510.2557.

1,3-diethyl 2-[3-(4-nitrophenyl)propyl]propanedioate (17)

To a round bottom flask containing 60% NaH in mineral oil (272 mg, 6.80 mmol) in ice bath was added 10 mL THF. Then a solution of diethyl malonate (1.04 g, 6.47 mmol) in THF (10 mL) was added dropwise over 10 min at 0° C. and the reaction mixture was stirred for 30 min. To the reaction mixture a solution of 16 (1.58 g, 6.47 mmol) in THF (10 mL) was added dropwise over 10 min. The reaction was allowed to room temperature and stirred for 1 d. The reaction mixture was quenched by H$_2$O (10 mL) and evaporated to dryness. The resulting residue was added H$_2$O (30 mL) and extracted with ethyl acetate (30 mL×3). The combined organic layers were dried over MgSO$_4$ and concentrated in vacuo to the dryness. The residue was purified via column chromatography on silica gel (60-220 mesh) eluting with 8% ethyl acetate/hexanes to afford pure 17 (1.46 g, 70%) as a light yellow oil. $^1$H NMR (CDCl$_3$, 300 MHz) δ 1.23 (t, J=7.2 Hz, 6H), 1.61-1.79 (m, 2H), 1.83-1.98 (m, 2H), 2.74 (t, J=7.5 Hz, 2H), 3.32 (t, J=7.2 Hz, 1H), 4.07-4.25 (m, 4H), 7.30 (d, J=8.6 Hz, 2H), 8.11 (d, J=8.6 Hz, 2H); $^{13}$C NMR (CDCl$_3$, 300 MHz) δ 14.0 (q), 28.2 (t), 28.5 (t), 35.4 (t), 51.7 (d), 61.5 (t), 123.7 (d), 129.2 (d), 146.4 (s), 149.5 (s), 169.2 (s).

5-(4-nitrophenyl)pentanoic acid (18)

Compound 17 (1.40 g, 4.33 mmol) was dissolved in the mixture of acetic acid (10 mL) and conc. HCl (10 mL), and the resulting solution was maintained at reflux for 24 h. The reaction was allowed to room temperature and evaporated to provide 18 (0.97 g, 100%) as a yellow solid that was used for the next step without further purification. $^1$H NMR ($D_2O$+NaOD, 300 MHz) δ 1.37 (s, 4H), 2.02 (s, 2H), 7.06 (d, J=8.4 Hz, 2H), 7.71 (d, J=8.4 Hz, 2H); $^{13}$C NMR ($D_2O$, 300 MHz) δ 25.5 (t), 30.1 (t), 34.8 (t), 37.3 (t), 123.2 (d), 129.1 (d), 145.3 (s), 151.6 (s), 183.4 (s).

methyl 2-bromo-5-(4-nitrophenyl)pentanoate (19)

Compound 18 (501.2 mg, 2.25 mmol) was added to a solution of $CCl_4$ (0.5 ml) and thionyl chloride (1.07 g, 8.98 mmol). The solution was brought to reflux for 1 h with initial liberation of HCl and $SO_2$. At this point, NBS (479.56 mg, 2.69 mmol) was added as solution in $CCl_4$ (1.4 ml), and 1 drop of 48% aqueous HBr catalyst was added to the warm solution. The dark solution was refluxed for an additional 35 min and became colorless. The solution was cooled and MeOH (7 ml) was added with stirring. The excess solvent was removed and dark oil was filtered through a flash silica gel pad (1×1-in.) using $CH_2Cl_2$. Evaporation of solvent gave mixture of yellow color oil (60:40). The residue was purified via column chromatography on silica gel (60-220 mesh) eluting 50% $CH_2Cl_2$ in hexane afford pure 19 (346.9 mg, 48.6%) as a yellow oil. $^1$H NMR ($CDCl_3$, 300 MHz) δ 1.61-1.89 (m, 2H), 1.96-2.06 (m, 2H), 2.72 (t, J=7.5 Hz, 2H), 3.72 (s, 3H), 4.22 (t, J=7.2 Hz, 1H), 7.29 (d, J=8.7 Hz, 2H), 8.09 (d, J=8.7 Hz, 2H); $^{13}$C NMR ($CDCl_3$, 300 MHz) δ 28.2 (t), 34.1 (t), 34.8 (t), 44.5 (d), 53.0 (t), 123.7 (d), 129.2 (d), 146.4 (s), 149.3 (s), 170.0 (s).

methyl 2-{4,7-bis[2-(tert-butoxy)-2-oxoethyl]-1,4,7-triazonan-1-yl}-5-(4-nitrophenyl)penta-noate (20)

Compound 19 (98.5 mg, 0.312 mmol) was added drop-wise to a solution of 14 (111.4 mg, 0.312 mmol) in $CH_3CN$ (2 mL) at 0° C. DIPEA (120.8 mg, 0.935 mmol) in $CH_3CN$ (2 mL) was added dropwise and the resulting mixture was allowed to room temperature and stirred for 72 h while monitoring the reaction progress using TLC. The progress of reaction was still slow in 72 h, solvent was evaporated, and DIPEA (40.3 mg, 0.312 mmol) in $CH_3CN$ (1.5 mL) was added. After 6 days, the reaction mixture was evaporated to dryness. The residue was dissolved with 0.1M HCl solution (10 mL) and washed with $CHCl_3$ (2×10 mL). The combined organic layers were dried over $MgSO_4$, filtered, and concentrated in vacuo to the dryness. The residue was purified via column chromatography on silica gel (60-220 mesh) and eluted with 10% MeOH in $CH_2Cl_2$ to provide pure 20 (123.3 mg, 66.8%) as a yellow solid. $^1$H NMR ($CDCl_3$, 300 MHz) δ 1.37 (s, 9H), 1.39 (s, 9H), 1.56-1.84 (m, 4H), 2.55-3.30 (m, 101H), 3.30-3.72 (m, 10H), 3.91-4.32 (m, 2H), 7.25 (d, J=8.7 Hz, 2H), 8.05 (d, J=8.4 Hz, 2H); $^{13}$C NMR ($CDCl_3$, 300 MHz) b 28.0 (q), 28.2 (t), 29.9 (t), 35.6 (t), 51.3 (q), 63.4 (d), 123.6 (d), 129.1 (d), 146.3 (s), 149.7 (s), 172.9 (s). HRMS (positive ion ESI) Calcd for $C_{30}H_{49}N_4O_8$ [M+H]$^+$ m/z 593.3545. Found: [M+H]$^+$ m/z 593.3529.

2-[4,7-bis(carboxymethyl)-1,4,7-triazonan-1-yl]-5-(4-nitrophenyl)pentanoic acid (3)

To compound 20 (37.7 mg, 0.0636 mmol) was added 6M HCl solution (3.5 mL), and the resulting solution was maintained at reflux for 3 h. The reaction was allowed to room temperature, and the resulting solution was filtered through celite using 18Ω $H_2O$ and dried in vacuo to provide compound 3 (33.4 mg, 91.2%) as a yellow solid. $^1$H NMR ($D_2O$+NaOD, 300 MHz) δ 1.34-1.79 (m, 4H), 2.06-3.35 (m, 19H), 7.25 (d, J=8.7 Hz, 2H), 8.05 (d, J=8.4 Hz, 2H); $^{13}$C NMR ($D_2O$+NaOD, 300 MHz) δ 27.2 (t), 28.3 (t), 34.9 (t), 45.7 (t), 51.6 (t), 52.3 (t), 53.5 (t), 54.9 (t), 71.4 (d), 123.6 (d), 129.1 (d), 145.8 (s), 151.2 (s), 180.0 (s), 180.3 (s), 181.7 (s). HRMS (positive ion ESI) Calcd for $C_{21}H_{29}N_4O_8$ [M−H]$^+$ m/z 465.1991. Found: [M−H]$^+$ m/z 465.1999.

Radiolabeling of the Bifunctional Chelators with $^{90}$Y and $^{177}$Lu.

All HCl solutions were prepared from ultra pure HCl (JT baker, #6900-05). For metal-free radiolabeling, plasticware including pipette tips, tubes, and caps was soaked in 0.1M HCl (aq) overnight and washed thoroughly with Milli-Q (18.2MΩ) water, and air-dried overnight. Ultra pure ammonium acetate (Aldrich, #372331) was purchased from Aldrich and used to prepare buffer solutions (0.25 M) at pH 5.5. After adjusting pH using 0.1 M HCl or NaOH solution, 0.25 M $NH_4OAc$ buffer solutions were treated with Chelex-100 resin (Biorad, #142-2842, 1 g/100 ml buffer solution), shaken overnight at room temperature, and filtered through 0.22 μM filter (Corning, #430320) prior to use. $^{90}$Y were purchased from Perkin Elmer. TLC plates (6.6×1 cm, Silica gel 60 $F_{254}$, EMD Chemicals Inc., #5554-7) with the origin line drawn at 0.6 cm from the bottom were prepared.

To a buffer solution (0.25M $NH_4OAc$, pH 5.5 or pH 7.0) in a capped microcentrifuge tube (1.5 mL, #05-408-129) was sequentially added a solution of a chelator in water (20 μg) and $^{90}$Y or $^{177}$Lu (60 μCi). The total volume of the resulting solution was 40 μL. The reaction mixture was agitated on the thermomixer (Eppendorf, #022670549) set at 1,000 rpm at room temperature for 1 h. The labeling efficiency was determined by ITLC eluted with $CH_3CN$/$H_2O$ (3:2 v/v) or 20 mM EDTA in 0.15 M $NH_4OAc$ as the mobile phase. A solution of radiolabeled complexes (2 μL) was withdrawn at the designated time points (1 min, 10 min, 20 min, 30 min, and 60 min), spotted on a TLC plate, and then eluted with the mobile phase. After completion of elution, the TLC plate was warmed and dried on the surface of a heater maintained at 35° C. and scanned using TLC scanner (Bioscan, #FC-1000). Unbound ($R_f$=0.6) and bound ($R_f$=0.9) radioisotope appeared around 30 mm and 50 mm from the bottom of the TLC plate eluted with $CH_3CN$/$H_2O$ (3:2 v/v), respectively. For the ITLC eluted with 20 mM EDTA in 0.15 M $NH_4OAc$ system, unbound ($R_f$=0.9) and bound ($R_f$=0.6) radioisotope appeared around 50 mm and 30 mm, respectively.

In Vitro Serum Stability of $^{90}$Y- and $^{177}$Lu-Radiolabeled Complexes.

Human serum was purchased from Gemini Bioproducts (#100110). $^{90}$Y- or $^{177}$Lu-radiolabeled complexes (0.25M $NH_{40}OAc$, pH 5.5) were prepared from the reaction of chelators with $^{90}$Y or $^{177}$Lu at room temperature or 37° C. Completion of radiolabeling was monitored by ITLC eluted, and the freshly prepared radiolabeled complexes were used for serum stability without further purification. $^{90}$Y-3p-C-DETA, $^{90}$Y-3p-C-NE3TA and $^{90}$Y-3-C-NOTA were prepared by a reaction of 3p-C-DETA (1), 3p-C-NE3TA (2) and 3p-C-NOTA (3) (50 μg) with $^{90}$Y (150 μCi) in 0.25 M $NH_4OAc$ buffer (pH 7.0). Radiolabeling of 3p-C-DETA, 3p-C-NE3TA and 3-C-NOTA with $^{90}$Y were complete in 2 h at 37° C. (600 rpm). $^{90}$Y-3p-C-DEPA (4) was prepared by a reaction of 3p-C-DEPA (100 μg, 100 μL) with $^{90}$Y (300 μCi) in 0.25 M $NH_4OAc$ buffer (pH 5.5). Radiolabeling of 3p-C-DEPA with $^{90}$Y was complete in 4 h at RT (1000 rpm) and 2 h at 37° C. (300 rpm). The complexes $^{90}$Y-3p-C-DETA, $^{90}$Y-3p-C-NE3TA, $^{90}$Y-3-C-NOTA, and $^{90}$Y-3p-C-

DEPA prepared from the reactions were directly used for serum stability studies without further purification. $^{90}$Y-3p-C-DETA (144 µCi, 99 µL), $^{90}$Y-3p-C-NE3TA (144 µCi, 99 µL), or $^{90}$Y-3-C-NOTA (144 µCi, 99 µL) was added to human serum (500 µL) in a microcentrifuge tube. $^{90}$Y-3p-C-DEPA (90 µCi, 63 µL) was added to human serum (330 µL) in a microcentrifuge tube. $^{177}$Lu-3p-C-DETA, $^{177}$Lu-3p-C-NE3TA, $^{177}$Lu-3-C-NOTA, and $^{177}$Lu-3p-C-DEPA were prepared by a reaction of 3p-C-DETA, 3p-C-NE3TA, 3p-C-NOTA, 3p-C-DEPA (50 µg) with $^{177}$Lu (150 µCi) in 0.25M NH$_4$OAc buffer (pH 5.5), respectively. Radiolabeling of 3p-C-DETA and 3p-C-DEPA with $^{177}$Lu was complete in 3 h at room temperature and 1000 rpm. Radiolabeling of 3p-C-NE3TA and 3p-C-NOTA with $^{177}$Lu was complete in 2 h at room temperature and 1000 rpm. The complexes $^{177}$Lu-3p-C-DECA, $^{177}$Lu-3p-C-DETA, $^{177}$Lu-3p-C-DEPA, $^{177}$Lu-3p-C-NE3TA, and $^{177}$Lu-3-C-NOTA prepared from the reactions were directly used for serum stability studies without further purification. $^{177}$Lu-3p-C-DETA (146 µCi, 100 µL), $^{177}$Lu-3p-C-DEPA (146 µCi, 100 µL), $^{177}$Lu-3p-C-NE3TA (149 µCi, 100 µL), or $^{177}$Lu-3-C-NOTA (149 µCi, 100 µL) was added to human serum (500 µL) in a microcentrifuge tube. The stability of the radiolabeled complexes in human serum was evaluated at 37° C. over 14 days. The serum stability of the radiolabeled complexes was assessed by measuring the transfer of the radionuclide from each complex to serum proteins using ITLC eluted with CH$_3$CN/H$_2$O (3:2 v/v) or 20 mM EDTA in 0.15 M NH$_4$OAc. A solution of the radiolabeled complex in serum was withdrawn at the designated time point, and the percentage of $^{90}$Y released from each of the radiolabeled complexes into serum was assessed by ITLC as described above.

Synthesis and Evaluation of Bimodal Chelators

Figure 12:
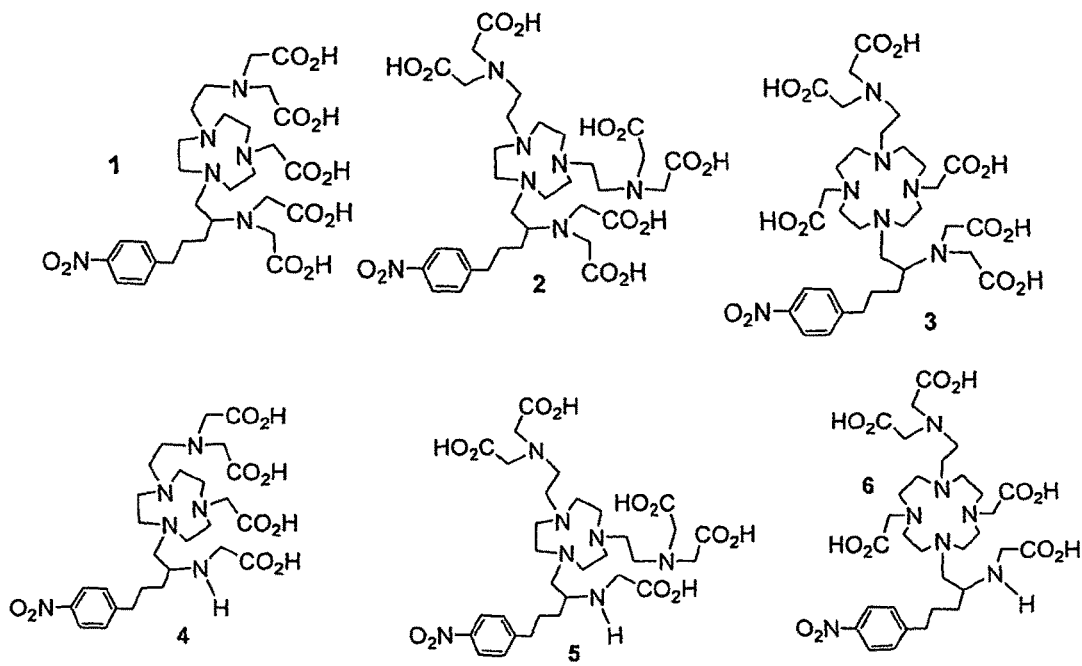
FIG. 12 illustrates backbones of chelators, according to one embodiment of this invention.
Figure 13:
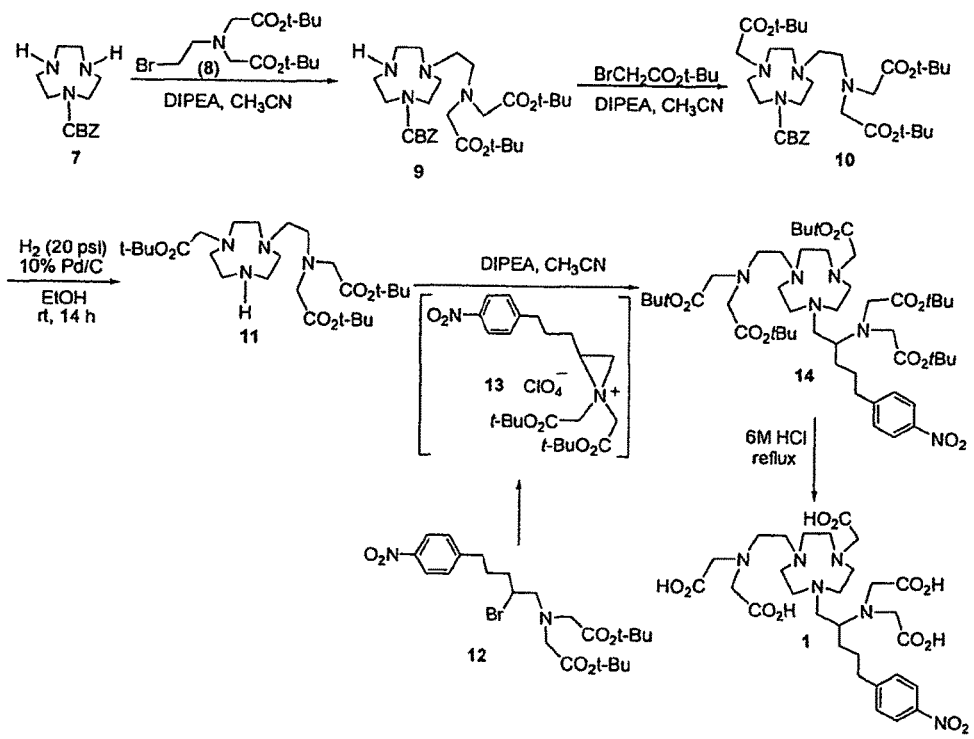
FIG. 13 is a reaction scheme of chelator 3p-C-DECA (1), according to one embodiment of this invention.
Figure 14:
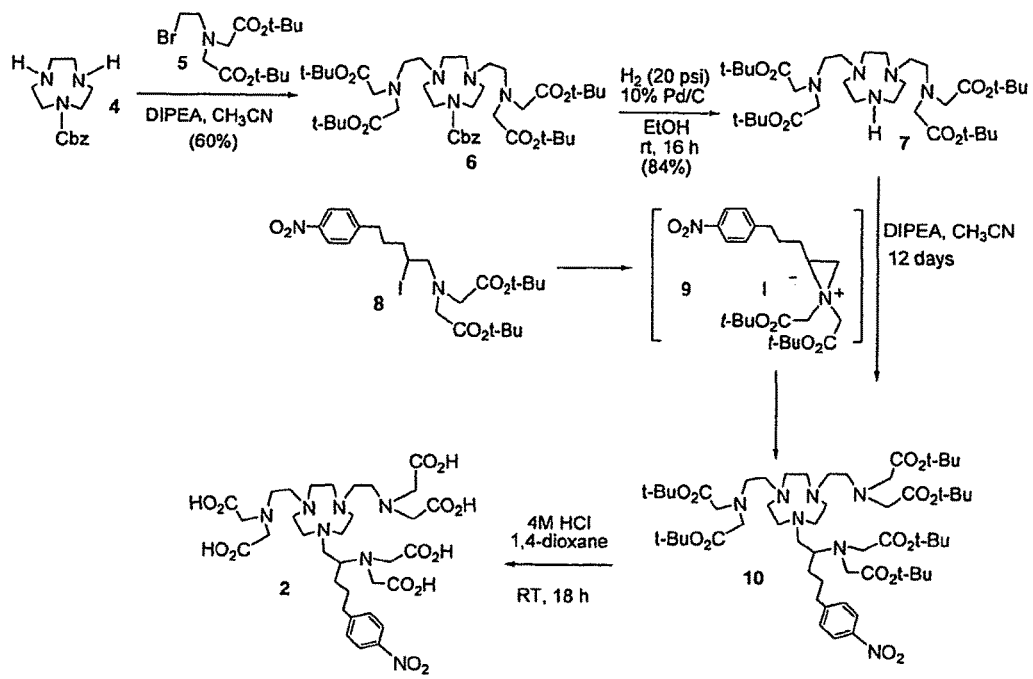
FIGS. 14 and 15 are each reaction schemes of chelators, according to embodiments of this invention.
Figure 15:
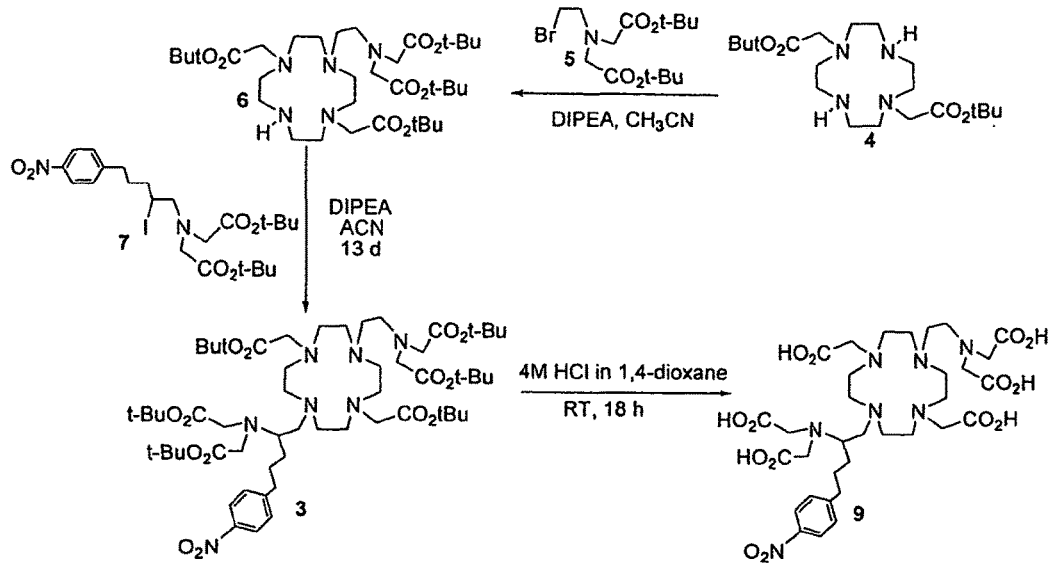

Syntheses of chelators shown in FIG. 12 are shown in FIGS. 13-15. The new chelators were evaluated for radiolabeling efficiency with $^{90}$Y and $^{177}$Lu (Tables 6-8). The chelator (30 µg) in 0.25M NH$_4$OAc buffer solution was radiolabeled with $^{90}$Y or $^{177}$Lu (60 µCi) at room temperature (RT). During the reaction time (1 h), the radiolabeling kinetics was determined using ITLC (20 mM EDTA in 0.15M NH$_4$OAc). The in vitro complex stability data indicate that $^{90}$Y or $^{177}$Lu-radiolabeled complexes of the chelators displayed excellent to good complex stability in serum.

Experimental Section $^1$H, $^{13}$C, and DEPT NMR spectra were obtained using a Bruker 300 instrument and chemical shifts are reported in parts per million (ppm) on the δ scale relative to TMS. Electrospray (ESI) high-resolution mass spectra (HRMS) were obtained on JEOL double sector JMS-AX505HA mass spectrometer (University of Notre Dame, South Bend, Ind.). The analytical HPLC was performed on an Agilent 1200 equipped with a dioarray detector (λ=254 and 280 nm), themostat set at 35° C., and a Zorbax Eclipse XDB-C18 column (4.6×150 mm, 80 Å). The mobile phase of a binary gradient (0-100% B/40 min; solvent A, 0.05 M AcOH/Et$_3$N, pH 6.0; solvent B, CH$_3$OH for method 1) at a flow rate of 1 mL/min was used. Semi-preparative HPLC was performed on an Agilent 1200 equipped with a dioarray detector (λ=254 and 280 nm), thermostat set at 35° C., and a Zorbax Eclipse XDB-C18 column (9.4×250 mm, 80 Å). The mobile phase of a binary gradient (0-100% B/160 min; solvent A, 0.05 M AcOH/Et$_3$N, pH 6.0; solvent B, CH$_3$OH for method 2; 0-100% B/80 min; solvent A, 0.05 M AcOH/Et$_3$N, pH 6.0; solvent B, CH$_3$OH for method 3) at a flow rate of 3 mL/min was used. All reagents were purchased from Sigma-Aldrich or Acros Organics and used as received unless otherwise noted.

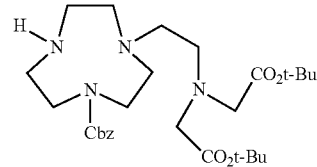

Benzyl 4-(2-{bis[2-(tert-butoxy)-2-oxoethyl]amino}ethyl)-1,4,7-triazonane-1-carboxylate (9)

To a solution of 8 (200 mg, 0.760 mmol) in CH$_3$CN (45 mL) was added bromide 7 (267.5 mg, 0.760 mmol) and DIPEA (98.2 mg, 0.760 mmol) in CH$_3$CN (5 mL). The resulting mixture was stirred for 20 h at room temperature, while monitoring the reaction progress using analytical HPLC (method 1, $t_R$=34.5 min). The reaction mixture was concentrated to dryness. The residue was purified by semi-prep HPLC (method 2, 84-110 min) to afford 9 (180 mg, 44%). $^1$H NMR (CDCl$_3$, 300 MHz) δ 1.38 (s, 18H), 2.40-2.52 (m, 2H), 2.54-2.86 (m, 7H), 2.87-3.06 (m, 2H), 3.13-3.52 (m, 8H), 5.08 (s, 2H), 7.15-7.35 (m, 5H); $^{13}$C NMR (CDCl$_3$, 300 MHz) δ 28.1 (q), 47.3 (t), 48.2 (t), 48.39 (t), 52.2 (t), 52.4 (t), 52.6 (t), 53.4 (t), 53.5 (t), 53.9 (t), 54.7 (t), 54.9 (t), 55.5 (t), 55.6 (t), 55.7 (t), 56.1 (t), 56.6 (t), 57.0 (t), 67.0 (t), 67.1 (t), 81.0 (s), 127.9 (d), 127.9 (d), 128.0 (d), 128.0 (d), 128.4 (d), 128.5 (d), 136.7 (s), 136.8 (s), 156.0 (s), 156.0 (s), 170.5 (s). HRMS (Positive ion ESI) Calcd for C$_{28}$H$_{47}$N$_4$O$_6$ [M+H]$^+$ m/z 535.3490. Found: [M+H]$^+$ m/z 535.3517.

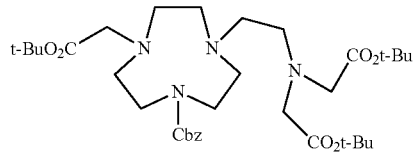

Benzyl 4-(2-{bis[2-(tert-butoxy)-2-oxoethyl]amino}ethyl)-7-[2-(tert-butoxy)-2-oxoethyl]-1,4,7-triazonane-1-carboxylate (10)

To a solution of 9 (150 mg, 0.281 mmol) in CH$_3$CN (2 mL) at 0° C. was added K$_2$CO$_3$ (40.7 mg, 0.295 mmol) and then tert-butyl bromoacetate (54.8 mg, 0.281 mmol) in CH$_3$CN (1 mL). The resulting mixture was stirred for 16 h at room temperature, while monitoring the reaction progress using TLC. The resulting mixture was evaporated to dryness. Then 0.1M HCl solution (30 mL) was added to the residue and extracted with ethyl acetate (30 mL×3). The combined organic layers were dried over MgSO$_4$, filtered, and concentrated in vacuo to provide 10 (175 mg, 96%). $^1$H NMR (CDCl$_3$, 300 MHz) δ 1.40 (s, 27H), 2.32-3.07 (m, 12H), 3.21 (d, J=19.5 Hz, 2H), 3.27-3.50 (m, 8H), 5.08 (s, 2H), 7.15-7.35 (m, 5H); $^{13}$C NMR (CDCl$_3$, 300 MHz) δ 28.1 (q), 28.2 (q), 49.6 (t), 49.8 (t), 50.0 (t), 50.5 (t), 52.1 (t), 54.0 (t), 54.5 (t), 54.8 (t), 55.2 (t), 55.8 (t), 56.0 (t), 56.1 (t), 56.3 (t), 56.6 (t), 58.8 (t), 66.7 (t), 80.6 (s), 80.7 (s), 80.8 (s), 127.8 (d), 127.9 (d), 128.4 (d), 137.1 (s), 156.1 (s), 170.6 (s), 170.7 (s), 171.4 (s). HRMS (Positive ion ESI) Calcd for $C_{34}H_{57}N_4O_8$ [M+H]$^+$ m/z 649.4171. Found: [M+H]$^+$ m/z 649.4187.

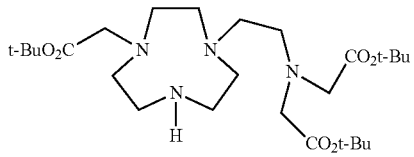

Tert-Butyl 2-{[2-(tert-butoxy)-2-oxoethyl](2-{4-[2-(tert-butoxy)-2-oxoethyl]-1,4,7-triazonan-1-yl}ethyl)amino}acetate (11)

To a solution of 10 (170 mg, 0.262 mmol) in ethanol (50 mL) at room temperature was added 10% Pd/C (45 mg) under Ar (g). The reaction mixture was placed under hydrogenation apparatus (20 Psi) for 14 h. The resulting mixture was filtered via celite bed and washed thoroughly with ethanol. The filtrate was concentrated to dryness. The crude product was treated with 0.1M HCl solution (20 mL) and extracted with CHCl$_3$ (20 mL×3). The aqueous layer was further treated with 2M NaOH solution and adjusted pH to 13, then extracted with CHCl$_3$ (20 mL×3). The combined organic layers from the extractions of the aqueous solution at pH 13 were dried over MgSO$_4$, filtered, and concentrated in vacuo to the dryness to provide product to provide 11 (120 mg, 89%) as a yellowish oil. $^1$H NMR (CDCl$_3$, 300 MHz) δ 1.45 (s, 27H), 2.52-2.91 (m, 10H), 2.93-3.18 (m, 6H), 3.20-3.60 (m, 7H); $^{13}$C NMR (CDCl$_3$, 300 MHz) δ 28.2 (q), 44.6 (t), 48.7 (t), 49.6 (t), 51.3 (t), 52.3 (t), 52.8 (t), 53.5 (t), 55.3 (t), 56.5 (t), 81.2 (s), 81.5 (s), 170.4 (s), 170.9 (s). HRMS (Positive ion ESI) Calcd for $C_{26}H_{51}N_4O_6$ [M+H]$^+$ m/z 515.3803. Found: [M+H]$^+$ m/z 515.3814.

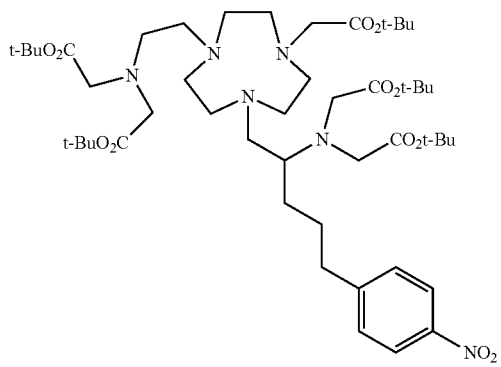

tert-butyl-2-({2-[4-(2-{bis[2-(tert-butoxy)-2-oxoethyl]amino}-5-(4-nitrophenyl)pentyl}-7-[2-(tert-butoxy)-2-oxoethyl]-1,4,7-triazonan-1-yl]ethyl}[2-(tert-butoxy)-2-oxoethyl]amino) acetate (14)

From 12-I: To a solution of 12-I (60.2 mg, 0.107 mmol) in CH$_3$CN (1 mL) at 0° C. was added compound 11 (55.0 mg, 0.107 mmol) and DIPEA (41.4 mg, 0.321 mmol). The resulting mixture was stirred for 14 d at room temperature, while monitoring the reaction progress using analytical HPLC (method 1, t$_R$=41.5 min). The reaction mixture was concentrated to dryness. The residue was purified via column chromatography on silica gel (60-220 mesh). The column was first eluted with 50% ethyl acetate in hexanes, then dried and eluted with 3% CH$_3$OH in CH$_2$Cl$_2$ to provide crude product. The crude product was further purified by semi-prep HPLC (method 3) to afford 14 (39 mg, 38%). $^1$H and $^{13}$C NMR data of 14 obtained in this reaction is essentially same as those of 14 described above.

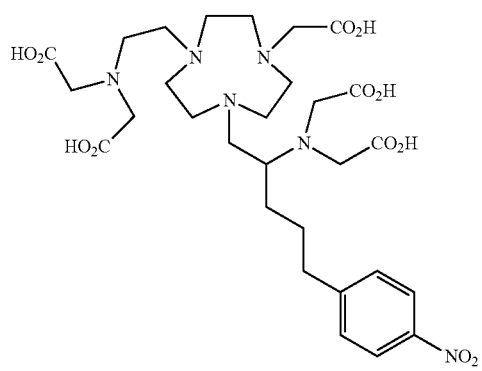 [SMILES: O=C(O)CN1CCN(CCN(CC(=O)O)CC(=O)O)CCN(CC(CCCc2ccc([N+](=O)[O-])cc2)N(CC(=O)O)CC(=O)O)CC1]

2-{[2-(4-{2-[bis(carboxymethyl)amino]-5-(4-nitrophenyl)pentyl}-7-(carboxymethyl)-1,4,7-triazonan-1-yl)ethyl](carboxymethyl)amino}acetic acid) (1)

To a flask containing compound 14 (17 mg, 0.0179 mmol) at 0-5° C. was added dropwise 4M HCl (g) in 1,4-dioxane (2 mL) over 5 min. The resulting mixture was gradually warmed to room temperature and continuously stirred for 24 h. Ether (30 mL) was added to the reaction mixture which was then stirred for 10 min. The resulting precipitate was filtered and washed with ether. The solid product was quickly dissolved in deionized water. The aqueous solution was concentrated in vacuo to provide product 1 (15 mg, 98%) as an off-white solid. $^1$H NMR (D$_2$O, 300 MHz) δ 1.19-1.83 (m, 4H), 2.68 (s, 2H), 2.81-3.78 (m, 21H), 3.93 (s, 6H), 7.33 (s, 2H), 8.04 (s, 2H). C-13 NMR HRMS (Negative ion ESI) Calcd for $C_{29}H_{43}N_6O_{12}$ [M−H]$^-$ m/z 667.2944. Found: [M−H]$^-$ m/z 667.2976.

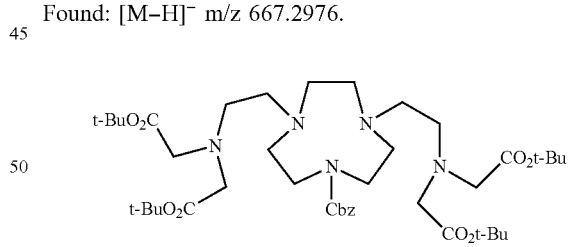

Benzyl 4,7-bis(2-{bis[2-(tert-butoxy)-2-oxoethyl]amino}ethyl)-1,4,7-triazonane-1-carboxylate (6)

To a solution of 4 (250 mg, 0.949 mmol) in CH$_3$CN (5 mL) was added 5 (669.04 mg, 1.90 mmol) and DIPEA (245.4 mg, 1.90 mmol) in CH$_3$CN (3 mL). The resulting mixture was stirred for 24 h at room temperature, while monitoring the reaction progress using TLC. The reaction mixture was concentrated to dryness. The residue was purified via column chromatography on silica gel (60-230 mesh) eluting with 3-5% CH$_3$OH in CH$_2$Cl$_2$ to afford pure 6 (459, mg, 60%).

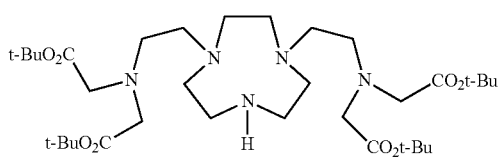

Tert-Butyl 2-({2-[4-(2-{bis[2-(tert-butoxy)-2-oxo-ethyl]amino}ethyl)-1,4,7-triazonan-1-yl]ethyl}[2-(tert-butoxy)-2-oxoethyl]amino)acetate (7)

To a solution of 6 (459 mg, 0.507 mmol) in ethanol (100 mL) at room temperature was added 10% Pd/C (100 mg) under Ar (g). The reaction mixture was placed under hydrogenation apparatus (20 Psi) for 16 h. The resulting mixture was filtered via celite bed and washed thoroughly with ethanol. The filtrate was concentrated to dryness. The crude product was treated with 0.1M HCl solution (20 mL) and extracted with $CHCl_3$ (3×20 mL). The aqueous layer was further treated with 2M NaOH solution and adjusted pH to 13, then extracted with $CHCl_3$ (3×20 mL). The combined organic layers from the extractions of the aqueous solution at pH 13 were dried over $MgSO_4$, filtered, and concentrated in vacuo to the dryness to provide product 7 (287 mg, 84.2%).

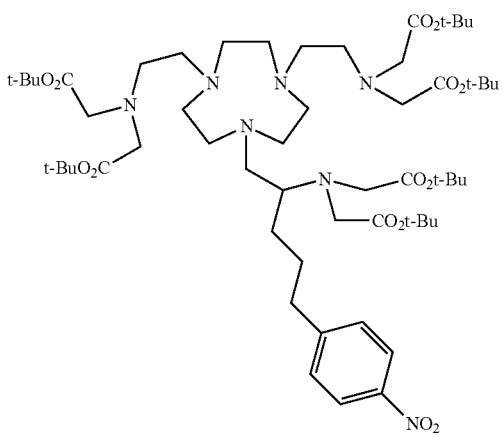

Tert-Butyl 2-({2-[4-(2-{bis[2-(tert-butoxy)-2-oxo-ethyl]amino}-5-(4-nitrophenyl) pentyl)-7-(2-{bis[2-(tert-butoxy)-2-oxoethyl]amino}ethyl)-1,4,7-triazonan-1-yl]ethyl}[2-(tert-butoxy)-2-oxoethyl]amino)acetate (10)

To a solution of 7 (100 mg, 0.149 mmol) in $CH_3CN$ (1 mL) at 0° C. was added compound 8 (86.22 mg, 0.149 mmol) and DIPEA (19.23 mg, 0.149 mmol). The resulting mixture was stirred for 20 d at room temperature, while monitoring the reaction progress using analytical HPLC (method 1, $t_R$=42.5 min). The reaction mixture was concentrated to dryness. The residue was purified via column chromatography on silica gel (60-220 mesh). The column was eluted with 3% $CH_3OH$ in $CH_2Cl_2$. Then the column was washed with 30% ethyl acetate in hexanes (200 mL) and 50% ethyl acetate in hexanes (200 mL) to provide crude product. The crude product was further purified by semi-prep HPLC (0-100% B/160 min; solvent A, 0.05 M AcOH/ $Et_3N$, pH 6.0; solvent B, $CH_3OH$, 137-148 min) to afford 10 (28 mg, 17%) as a yellowish oil.

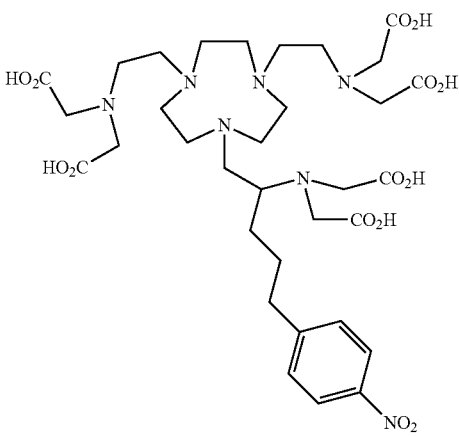 [SMILES: O=C(O)CN(CCN1CCN(CCN(CC(=O)O)CC(=O)O)CCN(CC(CCCc2ccc([N+](=O)[O-])cc2)N(CC(=O)O)CC(=O)O)CC1)CC(=O)O]

2-{[2-(4-{2-[bis(carboxymethyl)amino]-5-(4-nitrophenyl)pentyl}-7-{2-[bis(carboxy-methyl)amino]ethyl}-1,4,7-triazonan-1-yl)ethyl](carboxymethyl)amino}acetic acid 2)

To a flask containing compound 10 (4.36 mg, 3.94 μmol) at 0-5° C. was added dropwise 4M HCl (g) in 1,4-dioxane (1 mL) over 5 min. The resulting mixture was gradually warmed to room temperature and continuously stirred for 18 h. Diethyl ether (20 mL) was added to the reaction mixture which was then stirred for 15 min. The resulting precipitate was filtered and washed with ether. The solid product was quickly dissolved in deionized water. The aqueous solution was concentrated in vacuo to provide product 2 (2.25 mg, 75%) as light yellow oil. Compound 2 was further purified by semi-prep HPLC (0-100% B/40 min; solvent A, 0.1% TFA in $CH_3CN$; solvent B, 0.1% TFA in $H_2O$, 29.5-30.5 min) at a flow rate of 3 mL/min to afford extra pure sample for analysis. Analytical HPLC (0-100% B/20 min; solvent A, 0.1% TFA in $CH_3CN$; solvent B, 0.1% TFA in $H_2O$, $t_R$=8.75 min).

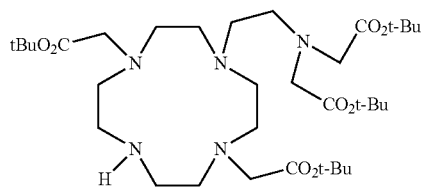 [SMILES: CC(C)(C)OC(=O)CN1CCNCCN(CC(=O)OC(C)(C)C)CCN(CCN(CC(=O)OC(C)(C)C)CC(=O)OC(C)(C)C)CC1]

Tert-Butyl 2-[(2-{4,10-bis[2-(tert-butoxy)-2-oxo-ethyl]-1,4,7,10-tetraazacyclododecan-1-yl}ethyl)[2-(tert-butoxy)-2-oxoethyl]amino]acetate (6)

To a solution of 4 (200 mg, 0.499 mmol) in $CH_3CN$ (20 mL) was added 5 (175.94 mg, 0.499 mmol) and DIPEA (64.53 mg, 0.499 mmol) in $CH_3CN$ (10 mL). The resulting mixture was stirred for 24 h at room temperature. The reaction mixture was concentrated to dryness to afford reaction mixture (452 mg). The residue was not purified to proceed to next step directly.

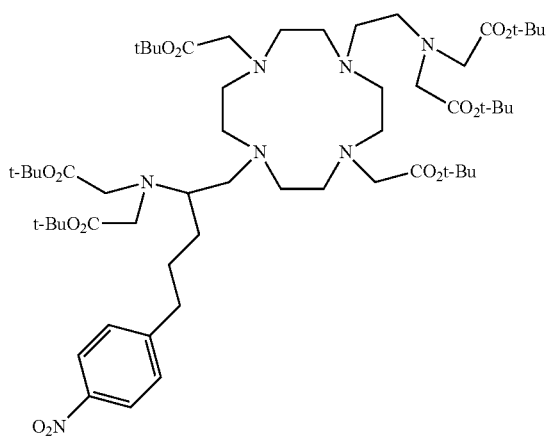

Tert-Butyl 2-({2-[7-(2-{bis[2-(tert-butoxy)-2-oxo-ethyl]amino}-5-(4-nitrophenyl) pentyl)-4,10-bis[2-(tert-butoxy)-2-oxoethyl]-1,4,7,10-tetraazacyclodo-decan-1-yl]ethyl}[2-(tert-butoxy)-2-oxoethyl]amino) acetate (8)

To a solution of 6 mixture (452 mg) in CH$_3$CN (5 mL) at 0° C. was added compound 7 (289.23 mg, 0.499 mmol) and DIPEA (64.53 mg, 0.499 mmol). The resulting mixture was stirred for 21 d at room temperature, while monitoring the reaction progress using analytical HPLC (0-100% B/40 min; solvent A, 0.05 M AcOH/Et$_3$N, pH 6.0; solvent B, CH$_3$OH, $t_R$=40.5 min). The reaction mixture was concentrated to dryness. The residue was purified via column chromatography on silica gel (60-220 mesh). The column was eluted with 3%-5% CH$_3$OH in CH$_2$Cl$_2$ to provide crude product. The crude product was further purified by semi-prep HPLC (0-100% B/160 min; solvent A, 0.05 M AcOH/Et$_3$N, pH 6.0; solvent B, CH$_3$OH, 139-148 min) to afford 8 (24 mg).

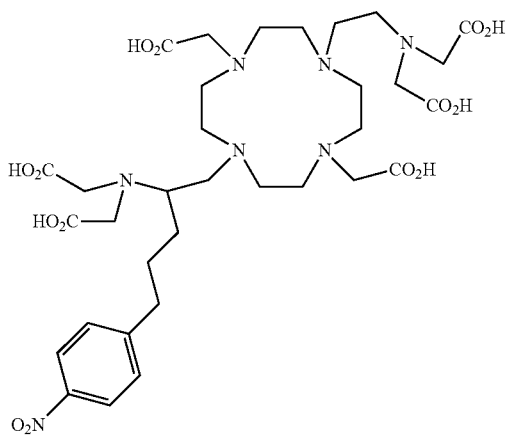 [SMILES: O=C(O)CN1CCN(CCN(CC(=O)O)CC(=O)O)CCN(CC(=O)O)CCN(CC(CCCc2ccc([N+](=O)[O-])cc2)N(CC(=O)O)CC(=O)O)CC1]

2-{[2-(7-{2-[bis(carboxymethyl)amino]-5-(4-nitrop-henyl)pentyl}-4,10-bis (carboxy methyl)-1,4,7,10-tetraazacyclododecan-1-yl)ethyl](carboxymethyl) amino}acetic acid (3)

To a flask containing compound 8 (4.5 mg, 4.1 μmol) at 0-5° C. was added dropwise 4M HCl (g) in 1,4-dioxane (1 mL) over 5 min. The resulting mixture was gradually warmed to room temperature and continuously stirred for 18 h. Diethyl ether (20 mL) was added to the reaction mixture which was then stirred for 15 min. The resulting precipitate was filtered and washed with ether. The solid product was quickly dissolved in deionized water. The aqueous solution was concentrated in vacuo to provide crude product 9 (3.10 mg, 98.7%). Compound 3 was further purified by semi-prep HPLC (0-100% B/40 min; solvent A, 0.1% TFA in CH$_3$CN; solvent B, 0.1% TFA in H$_2$O, 33.2-34.0 min) at a flow rate of 3 mL/min to afford extra pure sample for analysis. Analytical HPLC (0-100% B/20 min; solvent A, 0.1% TFA in CH$_3$CN; solvent B, 0.1% TFA in H$_2$O, $t_R$=9.3 min).

Radiolabeling of new chelators with $^{90}$Y and $^{177}$Lu. All HCl solutions were prepared from ultra-pure HCl (JT baker, #6900-05). For metal-free radiolabeling, plasticware including pipette tips, tubes, and caps was soaked in 0. lN HCl overnight and washed thoroughly with Milli-Q (18.2MΩ) water, and air-dried overnight. Ultra-pure ammonium acetate (Aldrich, #372331) was purchased from Aldrich and used to prepare buffer solutions (0.25 M) at pH 5.5. After adjusting pH using 0.1 M/1 M HCl or NaOH solution, 0.25M NH$_4$OAc buffer solutions were treated with Chelex-100 resin (Biorad, #142-2842, 1 g/100 ml buffer solution), shaken overnight at room temperature, and filtered through 0.22 μM filter (Corning, #430320) prior to use. To a buffer solution (0.25M NH$_4$OAc, pH 5.5) in a capped microcentrifuge tube (1.5 mL, #05-408-129) was sequentially added a solution of each chelator in water solution (20 μg/20 μL). $^{90}$Y in HCl or $^{177}$Lu in HCl (0.05M, 60 μCi) was added and the total volume of the resulting solution was brought up to 40 μL by adding the buffer solution. The reaction mixture was agitated on the thermomixer (Eppendorf, #022670549) set at 1,000 rpm at room temperature for 1 h. The labeling efficiency was determined by ITLC eluted with acetonitrile/water (3:2 v/v) as the mobile phase. A solution of radiolabeled complexes (2 μL) was withdrawn at the designated time points (1 min, 10 min, 20 min, 30 min, and 60 min), spotted on a TLC plate, and then eluted with the mobile phase. After completion of elution, the TLC plate was warmed and dried on the surface of a heater maintained at 35° C. and scanned using TLC scanner (Bioscan, #FC-1000). Unbound and bound radioisotope appeared around 30 mm and 50 mm from the bottom of the TLC plate, respectively.

TABLE 6

Radiolabeling efficiency (%) of chelators with $^{90}$Y (pH 5.5, RT)*

| Time (min) | Radiolabeling efficiency (%) Chelator (1) |
|---|---|
| 1 | 97.0 ± 1.0 |
| 10 | 99.0 ± 0.4 |
| 20 | 99.7 ± 0.1 |
| 30 | 99.7 ± 0.06 |
| 60 | 99.8 ± 0.2 |

*Radiolabeling efficiency (mean ± standard deviation %) was measured in triplicate at pH 5.5 using ITLC.

TABLE 7

Radiolabeling efficiency (%) of chelators with $^{177}$Lu (pH 5.5, RT)*

| Time (min) | Radiolabeling efficiency (%) Chelator 1 | Radiolabeling efficiency (%) Chelator 2 |
|---|---|---|
| 1 | 97.4 ± 0.10 | 81.6 ± 0.35 |
| 10 | 98.6 ± 0.10 | 99.4 ± 0.07 |
| 20 | 99.3 ± 0.10 | |
| 30 | 99.4 ± 0.10 | 99.8 ± 0.14 |
| 60 | 99.5 ± 0.06 | 99.8 ± 0.14 |

*Radiolabeling efficiency (mean ± standard deviation %) was measured in triplicate at pH 5.5 using ITLC.

In Vitro Stability of $^{90}$Y- or $^{177}$Lu-Radiolabeled Complexes.

Human serum was purchased from Gemini Bioproducts (#100110). The radiolabeled complexes was prepared and directly used for serum stability studies without further purification. The stability of the pure radiolabeled complexes in human serum was evaluated at 37° C. for 2 weeks. The serum stability of the radiolabeled complexes was assessed by measuring the transfer of the radionuclide from each complex to serum proteins using ITLC (acetonitrile/water (3:2 v/v). A solution of the radiolabeled complex in serum (5-16 µL for ITLC) was withdrawn at the designated time point and evaluated by ITLC. At each of the time points, the percentage of $^{90}$Y released from each of the radiolabeled complexes into serum was assessed by ITLC.

TABLE 8

In vitro serum stability of $^{177}$Lu- or $^{90}$Y-radiolabeled complexes (pH 7 and 37° C.)

| Time (hour) | $^{177}$Lu-Chelator 1 Bound radiolabeled complex (%) | Time (hour) | $^{90}$Y-Chelator 1 Bound radiolabeled complex (%) | Time (hour) | $^{177}$Lu-Chelator 2 Bound radiolabeled complex (%) |
|---|---|---|---|---|---|
| 0 | 100 ± 0.07 | 0 | 100 ± 0.00 | 0 | 99.9 ± 0.0 |
| 24 | 100 ± 0.07 | 24 | 100 ± 0.06 | 24 | 99.6 ± 0.07 |
| 48 | 100 ± 0.00 | 48 | 100 ± 0.00 | 72 | 99.7 ± 0.14 |
| 72 | 100 ± 0.00 | 96 | 100 ± 0.00 | 120 | 99.9 ± 0.07 |
| 96 | 100 ± 0.07 | 111 | 100 ± 0.00 | 168 | 99.9 ± 0.14 |
| 120 | 100 ± 0.07 | 118 | 99.8 ± 0.06 | 240 | 99.9 ± 0.0 |
| 144 | 100 ± 0.00 | 144 | 99.9 ± 0.06 | 288 | 99.8 ± 0.0 |
| 168 | 100 ± 0.00 | 168 | 99.8 ± 0.06 | 336 | 99.8 ± 0.0 |
| 192 | 100 ± 0.00 | 191 | 99.9 ± 0.00 | | |
| 240 | 100 ± 0.00 | 213 | 99.9 ± 0.06 | | |
| 264 | 100 ± 0.00 | 262 | 98.9 ± 1.34 | | |
| 288 | 100 ± 0.00 | 286 | 97.3 ± 2.92 | | |
| 312 | 100 ± 0.00 | 313 | 97.2 ± 2.46 | | |
| 336 | 100 ± 0.00 | 336 | 98.4 ± 0.67 | | |

*Radiolabeling efficiency (mean ± standard deviation %) was measured in triplicate at pH 5.5 using ITLC radiolanthanides can be very toxic when deposited into normal tissue, the application of an optimal bifunctional chelator to hold tightly the metals in vivo is critical to minimize toxic side effects related to dissociation of a radiolabeled complex during radiotherapy.

Figure 16:
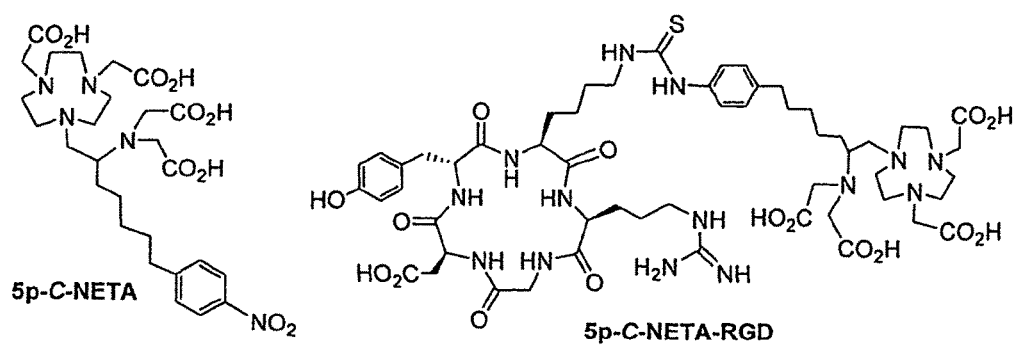
FIG. 16 illustrates a NETA-based functionalized ligand and NETA-RGD conjugate, according to one embodiment of this invention.

A bifunctional chelator 5p-C-NETA (2-({1-[4,7-bis(carboxymethyl)-1,4,7-triazonan-1-yl]-7-(4-nitrophenyl)heptan-2-yl}(carboxy-methyl)amino)acetic acid, as shown in FIG. 16, was synthesized and evaluated for use in molecular targeted radiotherapy of bone metastases. The bifunctional chelator was evaluated for complexation with $^{90}$Y and $^{177}$Lu and conjugated to a macrocyclic peptide c(RGDyK) targeting integrin $\alpha_v\beta_3$ receptor in cancers. The corresponding $^{177}$Lu-radiolabeled NETA-c(RGDyK) conjugates were further evaluated in vivo.

The bifunctional chelator instantly bound to $^{90}$Y or $^{177}$Lu at room temperature, and $^{90}$Y or $^{177}$Lu-radiolabeled complexes possess an excellent serum stability profile with no loss of the radioactivity over 14 days. The bifunctional chelator was conjugated to the cyclic Arg-Gly-Asp-D-Tyr-Lys (RGDyK) peptide targeting integrin $\alpha_v\beta_3$ that is overexpressed on many cancer cells. The corresponding 5p-C-NETA-c(RGDyK) conjugate rapidly bound to $^{90}$Y or $^{177}$Lu, and the radiolabeled 5p-C-NETA-RGD conjugate remained quite stable in human serum for 2 weeks. The in vitro binding affinities of c(RGDyK) and the 5p-C-NETA-c(RGDyK) conjugate were compared in competitive binding assays using U87MG human glioblastoma cells. The result of the binding assay showed that conjugation of c(RGDyK) peptide with the chelator had no significant effect on the binding affinity of the peptide to the receptor. $^{177}$Lu-NETA-RGD was shown to target tumors in mice and produced a favorable biodistribution profile with rapid blood clearance and low organ uptake. The result indicates that $^{90}$Y- and $^{177}$Lu-labeled 5p-C-NETA-c(RGDyK) conjugate are promising radiopharmaceuticals for integrin $\alpha_v\beta_3$-targeted radiotherapy for bone metastases.

The bifunctional chelator (5p-C-NETA) contains the functional group (p-NO$_2$-Bn) connected to the NETA backbone via a pentyl chain. The design of the NETA chelator with the longer alkyl chain was intended for providing sufficient spacing between the RGD peptide and chelating NETA backbone and thereby minimizing steric hindrance in NETA-c(RGDyK) Peptide Conjugate for Integrin $\alpha_v\beta_3$-Targeted Radiotherapy Using β-Emitting Radionuclides Many cancer cells including prostate and breast cancers develop bone metastases. Metastatic breast and prostate cancer remain essentially incurable, and better drugs to detect, stage, and cure the disease are in critical need. α- or β-emitting cytotoxic radionuclides have been successfully applied to therapy of bone metastases. There would be great interest in molecular targeted radiopharmaceuticals containing a bifunctional chelator and a receptor targeting vector that can function independently and effectively for complexation of a β-emitting radiolanthanide and specific targeting to receptors in bone metastases, respectively. Since the binding of RGD conjugate to the receptor and maintaining high binding affinity to the receptor.

Figure 17:
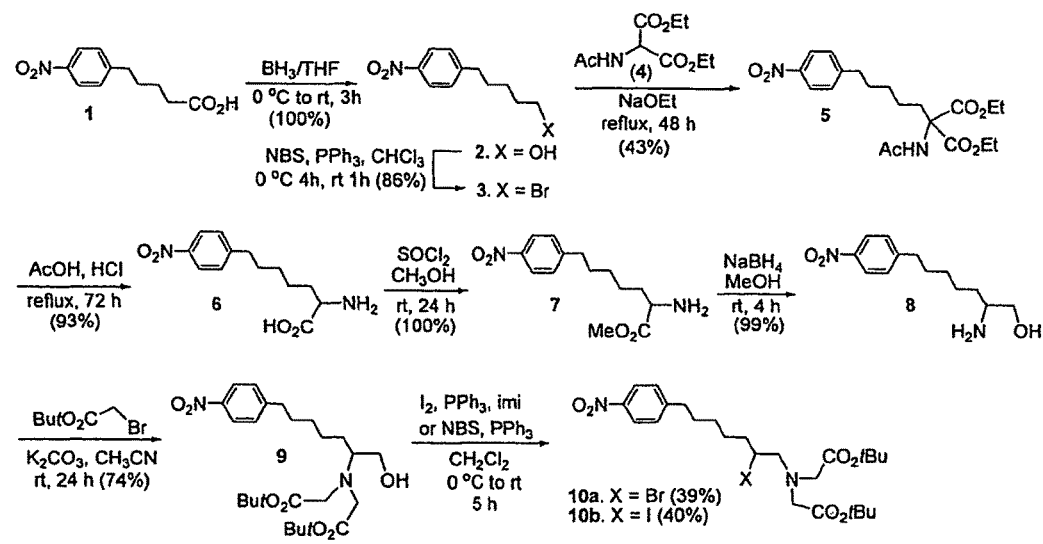
FIG. 17 is a reaction scheme of chelator N,N-bisubstituted secondary β-haloamine (10), according to one embodiment of this invention.
Figure 18:
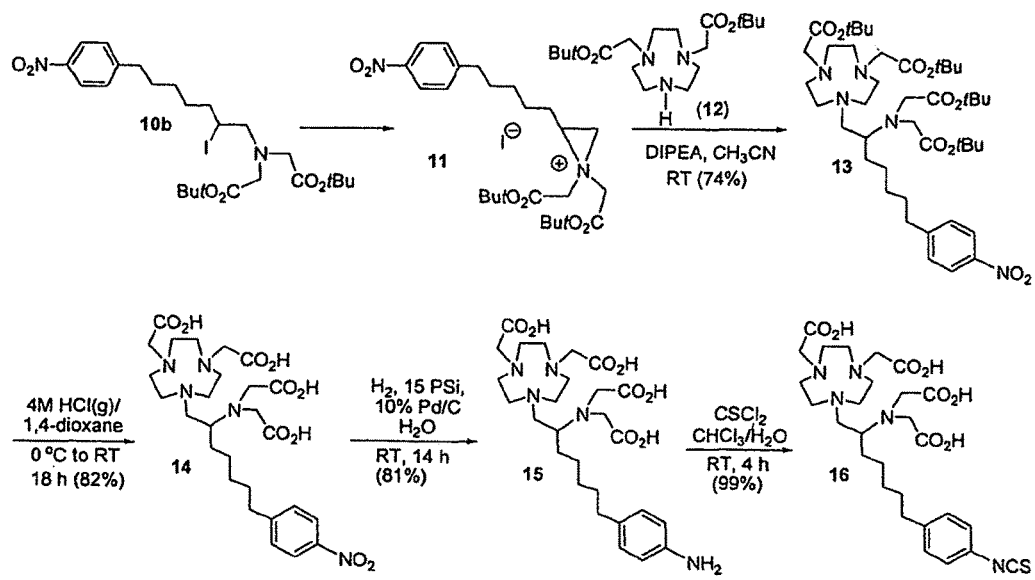
FIG. 18 is a reaction scheme of bifunctional 5p-C-NETA chelators, according to one embodiment of this invention.
Figure 19:
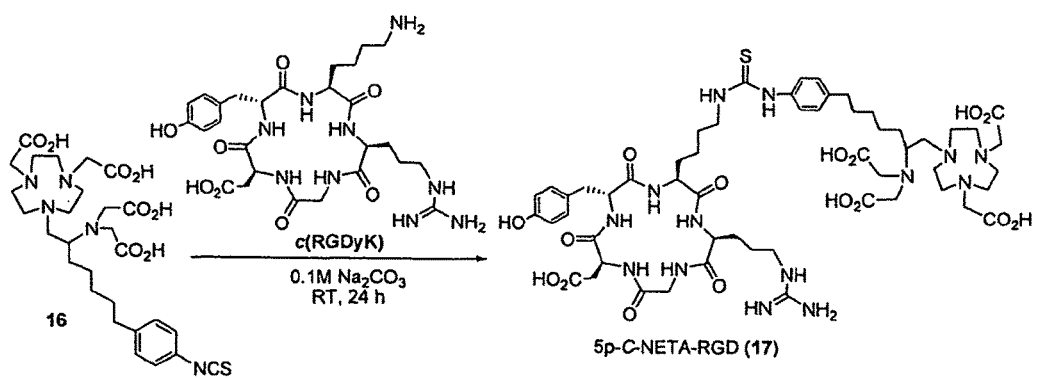
FIG. 19 shows conjugation of 5p-C-NETA chelator to c(RGDyK) peptide, according to one embodiment of this invention.

The synthesis of precursor molecules and the bifunctional chelator is shown in FIGS. 17-18. The key step in the synthesis of the bifunctional chelators is the regiospecific ring opening of aziridinium ions (11, FIG. 17) by bisubstituted 1,4,7-triazacyclononane (12, FIG. 18). Aziridinium salts can be initially formed from intramolecular rearrangement of primary N,N-bisubstituted β-amino bromides via neighboring group participation of nitrogen, and ring opening of aziridinium ion by the counter anion bromide can occur at the more hindered carbon leading to secondary β-bromoamines. Synthesis of the secondary N,N-bisubstituted β-iodoamine (11) as the key precursor molecule is shown in FIG. 17. Reduction of carboxylic acid 1 using $BH_3$/THF afforded alcohol 2 in quantitative yield. Bromination of 2 using NBS and $PPh_3$ produced 3 which was reacted with sodium salt of diethyl acetamido malonate (4) afforded compound 5. Racemic p-nitrophenylpropylalanine 6 was prepared from decarboxylation and removal of the acetyl protection group in 5 and further converted to amino methyl ester 7. Reduction of 7 with $NaBH_4$ followed by alkylation of 8 with t-butyl bromoacetate provided 9. Halogenation of 9 using $NBS/PPh_3$ and $I_2/PPh_3$ provided the secondary β-haloamine 10a and 10b, respectively. Synthesis of the bifunctional chelator 5p-C-NETA is shown in the scheme of FIG. 18. Intromolecular rearrangement of β-iodoamine 10b for formation of aziridinium ion 11 followed by regiospecific ring opening with 12 provided the desired product 13 in a good isolated yield (74%). Initially, the ring opening reaction of 10a with 12 provided 13 in a lower yield. The t-butyl groups in 13 were removed by the treatment of 13 with 4M HCl/1,4-dioxane to produce 5p-C-NETA (14). The nitro group in 14 was converted to the amino group to afford the bifunctional chelator 15 which was subsequently reacted with thiophosgene to provide the desired bifunctional chelator 16 containing an isothiocyanate group for conjugation to a peptide containing an amino group. The bifunctional chelator 16 was conjugated to cyclic RGDyK (Arg-Gly-Asp-D-Tyr-Lys) peptide to produce 5p-C-NETA-c(RGDyK) (17) (FIG. 19). The base-promoted reaction of 16 with c(RGDyK) provided the desired NETA-RGD conjugate 18 which was purified by semi-prep HPLC.

5p-C-NETA and 5p-C-NETA-RGD conjugate were evaluated for radiolabeling efficiency with the β-emitting radioisotopes, $^{90}Y$ and $^{177}Lu$. Radiolabeling of 5p-C-NETA with $^{90}Y$ or $^{177}Lu$ was performed at room temperature and pH 5.5 and evaluated using ITLC. 5p-C-NETA instantly bound to $^{90}Y$ or $^{177}Lu$ at pH 5.5 (>99%, 1 min, Table 9). In particular, radiolabeling of 5p-C-NETA with $^{90}Y$ was significantly faster relative to C-DOTA (>84%, 1 h). C-DOTA is known to form a complex with $^{90}Y$ or $^{177}Lu$ with slow complexation kinetics. The 5p-C-NETA-c(RGDyK) conjugate was evaluated for radiolabeling with $^{90}Y$ or $^{177}Lu$ at room temperature (pH 5.5, RT). Radiolabeling of the NETA-RGD conjugate with $^{90}Y$ or $^{177}Lu$ was slightly slower than that of 5p-C-NETA. It appears that conjugation of the chelator to the RGD peptide affected complexation of the conjugate with the metal (the respective radiolabeling efficiency of 71% and 90% for $^{90}Y$ and $^{177}Lu$). However, the NETA-RGD conjugate almost completely bound to $^{90}Y$ or $^{177}Lu$ at 5 min time point (>99% radiolabeling efficiency, Table 9). In vitro serum stability of 5p-C-NETA and NETA-RGD conjugates radiolabeled with $^{90}Y$ or $^{177}Lu$ was performed to determine if NETA chelators or NETA-RGD conjugates radiolabeled with $^{90}Y$ or $^{177}Lu$ remained stable without loss of $^{90}Y$ or $^{177}Lu$ in human serum. This was assessed by measuring the transfer of $^{90}Y$ or $^{177}Lu$ from the complex to serum proteins over the course of 14 days using ITLC. $^{90}Y$ or $^{177}Lu$-radiolabeled complexes was prepared from the reactions of the bifunctional chelators with $^{90}Y$ or $^{177}Lu$ at room temperature and directly used for serum stability studies (37° C., pH 7). Both $^{90}Y$-5p-C-NETA and $^{177}Lu$-5p-C-NETA remained stable in human serum without releasing the radioactivity into the serum. The sample of the $^{90}Y$- or $^{177}Lu$-NETA-RGD conjugate in serum was withdrawn and challenged with 1 mM DTPA solution, and the mixture was incubated for 20 min. $^{90}Y$-NETA-RGD and $^{177}Lu$-NETA-RGD conjugates remained quite stable in human serum over 2 weeks period (Supporting Information). Even after the challenge of the mixture with the DTPA solution, only a small amount of the radioactivity (<5%) was lost from the complex. The serum stability data indicate that conjugation of NETA chelator with RGD peptide via the pentyl alkyl spacer has little impact on complexation kinetics and stability of the NETA chelator with $^{90}Y$ and $^{177}Lu$.

TABLE 9

*Radiolabling efficiency (%) of 5p-C-NETA or 5p-C-NETA-RGD conjugate with $^{90}Y$ or $^{177}Lu$ (RT, 0.25M $NH_4OAC$, pH 5.5).

| Time (min) | 5p-C-NETA | | 5p-C-NETA-RGD | |
|---|---|---|---|---|
| | $^{90}Y$ | $^{177}Lu$ | $^{90}Y$ | $^{177}Lu$ |
| 1 | 99.3 ± 0.1 | 99.6 ± 0.1 | 70.8 ± 7.0 | 90.0 ± 4.0 |
| 5 | 99.7 ± 0.3 | 99.7 ± 0.3 | 98.5 ± 0.5 | 99.9 ± 0.2 |
| 10 | 99.8 ± 0.1 | 99.6 ± 0.1 | 99.6 ± 0.1 | 99.9 ± 0.0 |
| 20 | 99.8 ± 0.1 | 99.7 ± 0.1 | 99.8 ± 0.1 | 99.9 ± 0.0 |
| 30 | 99.9 ± 0.1 | 99.8 ± 0.2 | 99.9 ± 0.1 | 100.0 ± 0.0 |
| 60 | 100.0 ± 0.0 | 99.9 ± 0.1 | 100.0 ± 0.1 | 100.0 ± 0.1 |

*Radiolabeling efficiency (mean ± standard deviation %) was measured in triplicate using ITLC.

In summary, the bifunctional chelator 5p-C-NETA was efficiently prepared and evaluated for complexation with $^{90}Y$ and $^{177}Lu$. The new chelator instantly bound to $^{90}Y$ or $^{177}Lu$ in excellent radiolabeling efficiency, and the corresponding $^{90}Y$- or $^{177}Lu$-radiolabeled 5p-C-NETA remained intact without a measurable loss of the radioactivity in human serum over 14 days. Conjugation of the chelator to the tumor targeting cyclic RGDyK peptide had no significant impact on radiolabeling efficiency, binding affinity, and in vitro serum stability. The results indicate that $^{90}Y$- and $^{177}Lu$-radiolabeled NETA-c(RGDyK) conjugate are promising radiopharmaceuticals for integrin $\alpha_v\beta_3$.targeted radiotherapy using β-emitting radionuclides.

Pyridyl-Containing Bifunctional Chelators for PET Imaging Using Cu-64

Figure 20:
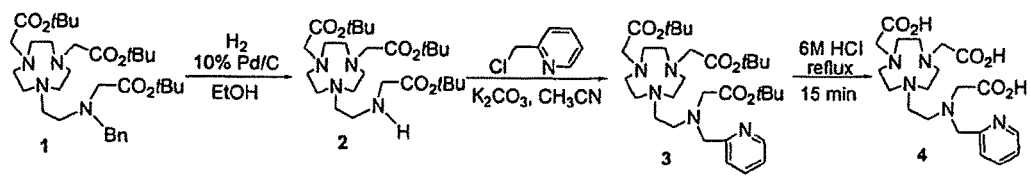
FIG. 20 is a reaction scheme of chelator pyridyl-containing octadentate chelator (4), according to one embodiment of this invention.
Figure 21:
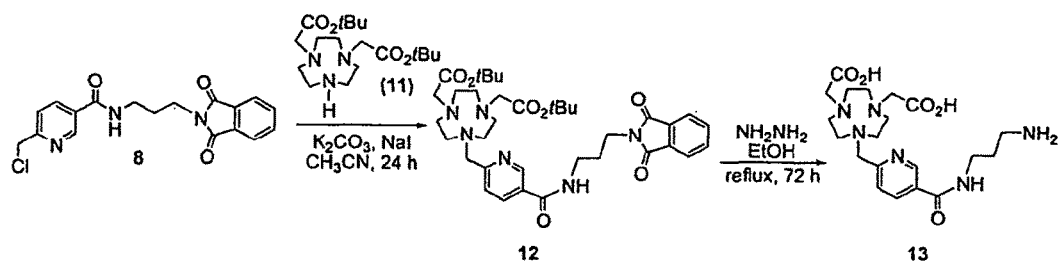
FIG. 21 is a reaction scheme of a chelator (14) according to one embodiment of this invention.
Figure 22:
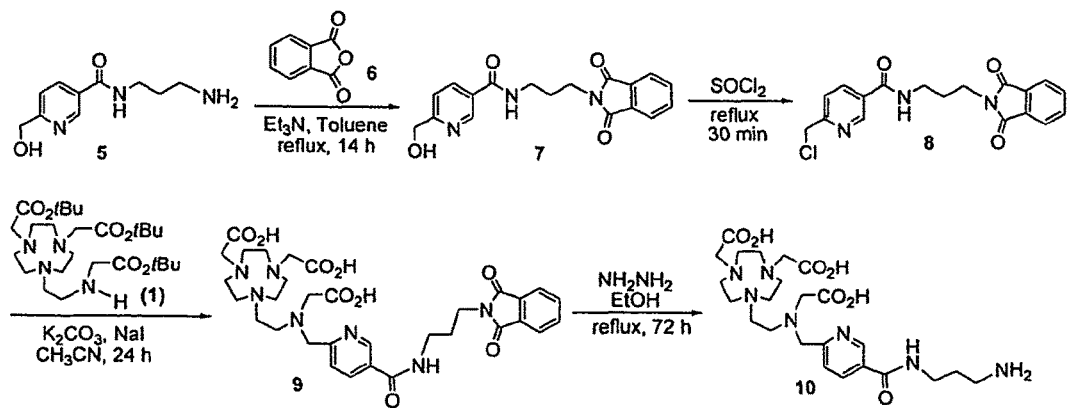
FIG. 22 is a reaction scheme of a chelator (10) according to one embodiment of this invention.

The following bifunctional chelators were prepared, with reaction schemes shown in FIGS. 20-22.

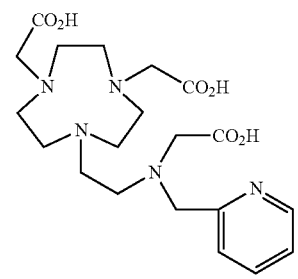

4

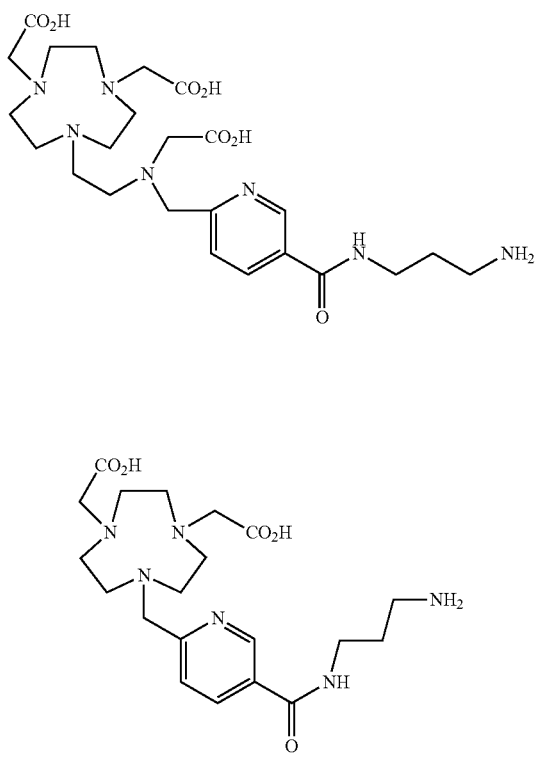

The pyridyl-containing chelators were synthesized and evaluated as chelators of $^{64}$Cu, $^{177}$Lu, and $^{90}$Y. The chelators were evaluated for complex kinetics and stability with the radionuclides, and the corresponding radiolabeled complexes were challenged by EDTA. The results are summarized in Tables 10-13.

Radiolabeling Kinetics.

Chelators 4, 10, and 13 were evaluated for radiolabeling efficiency with $^{64}$Cu and $^{177}$Lu (Tables 11 and 12). A chelator (30 μg) in 0.25M NH$_4$OAc buffer solution was radiolabeled with $^{64}$Cu or $^{177}$Lu (60 μCi) at room temperature (RT). During the reaction time (1 h), the radiolabeling kinetics was determined using ITLC as described above. Radiolabeling of all chelators with $^{64}$Lu was nearly complete at the starting point of radiolabeling. Octadentate chelators 4 and 10 were faster in binding $^{177}$Lu as compared to hexadentate chelator 13.

TABLE 10

Radiolabeling of new chelators with
$^{64}$Cu (RT, pH 5.5, ITLC and HPLC)*

| Time (min) | Chelator 10 Labeling Efficiency (%) | Chelator 4 Labeling Efficiency (%) | Chelator 13 Labeling Efficiency (%) |
|---|---|---|---|
| 1 | 99.8 ± 0.14 | 99.9 ± 0.0 | 100 ± 0.07 |
| 10 | 100 ± 0.0 | 99.9 ± 0.0 | 100 ± 0.0 |
| 30 | 99.9 ± 0.14 | 99.9 ± 0.07 | 100 ± 0.0 |

TABLE 11

Radiolabeling efficiency (%) of Pyridyl-based chelators with $^{177}$Lu (RT, pH 5.5)

| | Lu-177 Labeling Efficiency (%) | | Y-90 labeling efficiency (%) |
|---|---|---|---|
| Time | Chelator 10 | Chelator 4 | Chelator 13 |
| 1 min | 15.6 ± 1.9 | 38.4 ± 2.4 | 11.3 ± 0.49 |
| 5 min | | 94.8 ± 0.35 | 53.4 ± 0.21 |
| 10 min | 76.4 ± 0.14 | | |
| 20 min | | | |
| 30 min | 97.9 ± 0.42 | 99.5 ± 0.35 | 82.1 ± 0.07 |
| 60 min | 99.5 ± 0.35 | 99.6 ± 0.28 | 92.6 ± 0.78 |

In Vitro Serum Stability.

In vitro serum stability of the radiolabeled complexes was performed to determine if the chelators radiolabeled with $^{64}$Cu remained stable without loss of the radioactivity in human serum as described above. All $^{64}$Cu-radiolabeled chelators remained intact in human serum for 2 days as evidenced by ITLC and HPLC analysis. When the complexes were checked for complex stability using HPLC, $^{64}$Cu-radiolabeled with chelator 4 was slightly more stable than the complexes of chelators 10 and 13.

TABLE 12

Complex Stability of $^{64}$Cu-radiolabeled complexes
in human serum (37° C., pH 7, ITLC and HPLC)

| Time (hour) | Chelator 10 Bound complex (%) | Chelator 4 Bound complex (%) | Chelator 13 Bound complex (%) |
|---|---|---|---|
| 0 | 99.9 ± 0.07 | 99.9 ± 0.0 | 100.0 ± 0.07 |
| | (98.3 ± 2.0) | (99.9 ± 0.0) | (100 ± 0.0) |
| 19 | 99.8 ± 0.14 | 100 ± 0.0 | 100.0 ± 0.0 |
| | (96.7 ± 0.0) | (99.9 ± 0.07) | (100 ± 0.0) |
| 48 | 99.9 ± 0.0 | 100 ± 0.07 | 99.9 ± 0.07 |
| | (97.2 ± 0.21) | (100.0 ± 0.0) | (100 ± 0.0) |

Bound complex (%) was measured in triplicate using ITLC (HPLC).

EDTA Challenge.

$^{64}$Cu- or $^{177}$Lu-radiolabeled complexes were prepared by reaction of each chelator (20 μg) with $^{64}$Cu or $^{177}$Lu (60 μCi) in 0.25M NH$_4$OAc buffer (pH 5.5) for 2 h at room temperature. The radiolabeled complexes were prepared as described above and directly used for the experiments. The radiolabeled complex was mixed with EDTA at a 100-fold molar excess. The resulting mixture was incubated for 24 h at 37° C. The stability of $^{64}$Cu-radiolabeled complexes in the solution was evaluated using ITLC (20 mM EDTA in 0.15M NH$_{40}$OAc). A solution of the radiolabeled complex in serum (3~20 μL) was withdrawn at the designated time points and evaluated by ITLC as described above. $^{177}$Lu-radiolabeled chelators 4 and 10 remained stable in EDTA solution without releasing significant amount of the radioactivity. $^{64}$Cu-radiolabeled chelator 13 was extremely stable in EDTA challenge.

TABLE 13

| | Stability of radiolabeld complexes in EDTA solution (37° C., pH 5.5) | | |
|---|---|---|---|
| | Lu-177 Bound (%) | | Cu-64 Bound (%) |
| Time (hour) | Chelator 4 | Chelator 10 | Chelator 13 |
| 0 | 99.8 | 99.8 | 100 ± 0.07 |
| 1 | 99.5 | 95.7 | 99.9 ± 0.07 |
| 6 | 99.2 | 94.9 | — |
| 24 | 98.3 | 94.6 | 99.2 ± 0.42 |

Preparation of Chelator 10-Cy5.5 Conjugate.

Figure 23:
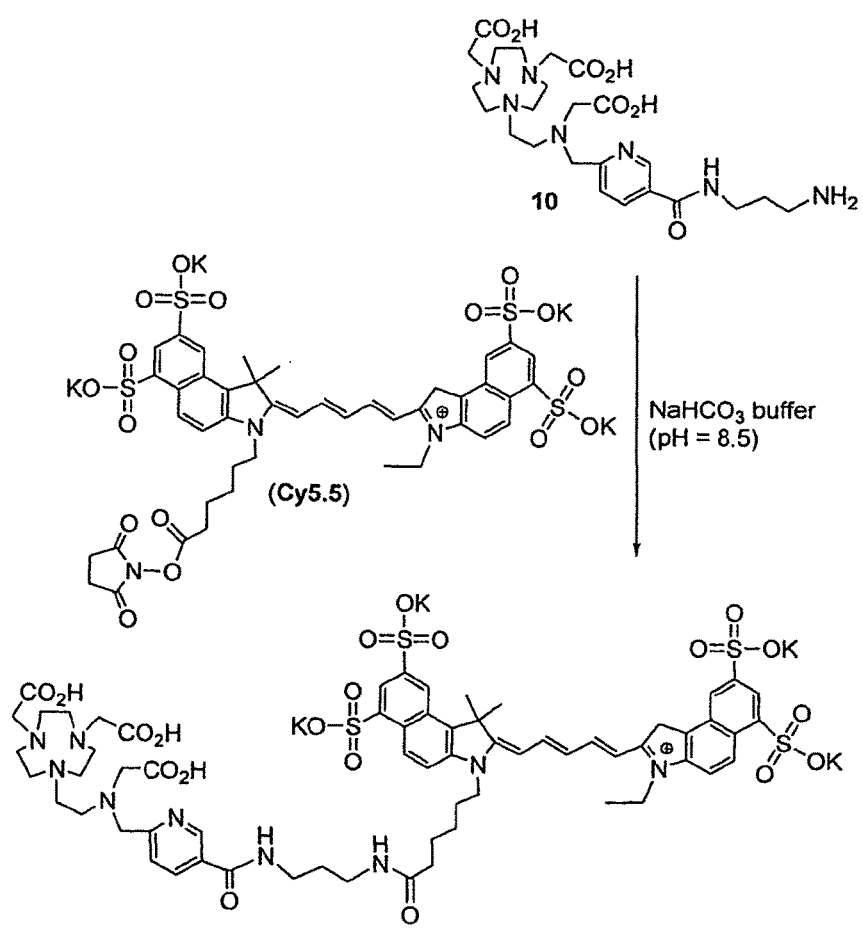
FIG. 23 shows development of dual imaging agents Cu-64-based PET imaging and Cy5.5-based Near IR fluorescence imaging, according to one embodiment of this invention.

Chelator 10 was conjugated with a near IR fluorescent dye Cy5.5 that can be used for dual optical and PET imaging to provide fluorescent conjugate as shown in FIG. 23. Chelator 10 in PBS was reacted with Cy5.5 for 16 h at RT. The conjugate was purified by RP-HPLC and evaluated for radiolabeling with $^{177}$Lu using TLC (solvent: 20 mM EDTA/ 0.15 M NH$_4$OAc) and HPLC (solvent: 0.1% TFA in H$_2$O and 0.1% TFA in ACN, ACN 0% to 100%, 15 min, C-18 column). The conjugate was labeled with $^{177}$Lu in 97% efficiency at 2 h time point.

Thus the invention provides new ligands and/or chelators for biomedical and/or environmental applications. The chelators have great promise for use in broad applications of cancer therapy, for example, decorporation therapy of radionuclides and iron chelation therapy, and imaging, such as, without limitation, magnetic resonance imaging (MRI), radioimmunotherapy (RIT), fluorescence imaging, positron emission tomography (PET).

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A compound of formula (I):

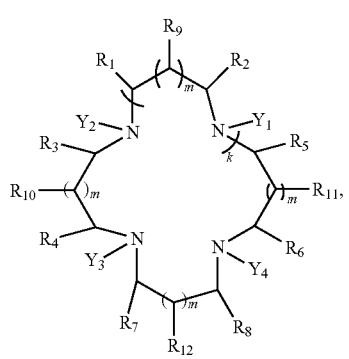

where k is 0 or 1; m is 0 or 1; and each of $Y_1$-$Y_4$ independently is one of a structure of formula (a-1), (a-2), or (a-3):

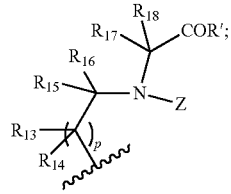

(a-1)

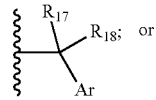

(a-2)

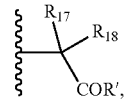

(a-3)

where p is 1 or 2; Z is hydrogen, formula (a-2), formula (a-3), Ar, a pyridylalkyl, a protecting group, an aryl containing group, an alkynyl containing group, an amine containing group, an azide containing group, or an amide containing group; Ar is or includes an aromatic ring or a heteroaromatic ring; and each R' independently is OH, NH$_2$, OR", NR$_2$" wherein each R" is one of alkyl, tert-butyl, allyl, benzyl, benzyloxy, or a protecting group; and wherein each of R$_{1-18}$ independently is or includes hydrogen, carboxyalkyl, alkylamido, alkyl, allyl, benzyl, benzyloxyalkyl, cycloalkyl, alkoxy, hydroxyalkyl, aryl, aryloxy, hydroxyaryl, heteroaryl, phenyl, vinyl, alkynyl, alkenyl, furannylalkyl, alkylthioalkyl, arylhydroxyalkyl, indanyl, inolylalkyl, naphthylalkyl, imidazolylalkyl, pyridiylalkyl, benzothiophenylalkyl, thiophenylalkyl, thioalkyl, thioaryl, thiobenzyl, hydroxy, an alkynyl containing group, substituted carbonyl, hydroxyalkyl, triazolylalkyl, aminoalkyl, benzothiophenylalkyl, carboxyl, carboxyalkyloxy, amine, a protected amine, carboxylic acid, holoalkylamido, aldehyde, ester, amido, tosyl, phthalimidyl, maleimidyl, trityl, tert-butyloxycarbonyl, carbobenzyloxy, o-nosyl, acetyl, fluoroacetyl, dimethoxybenzyl, p-methoxybenzyl, an amide containing group, a thioamide containing group, an amino acid-containing group, an ester containing group, a protecting group, an amine protecting group or:

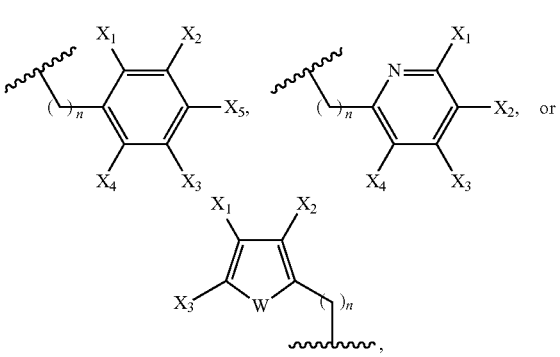

where W is NH, oxygen, or sulfur, n is 1-5, and each of $X_1$-$X_5$ independently is or includes hydrogen, halo, cyano, alkyl, hydroxy, nitro, amino, alkylamino, thiocyano, isothiocyano, alkoxy, aryloxy, carboxyl, carboxyalkyl, carboxyalkyloxy, ester, amido, aldehydo, alkylamido, holoalkylamido, an ester containing group, an carbonyl containing group, an amide containing group, an amine containing group, a thioamide containing group, an alkynyl containing group, or an amino acid-containing group;

wherein more than one of $Y_1$-$Y_4$ is formula (a-1); and wherein at least one of $Y_1$-$Y_4$ comprises:

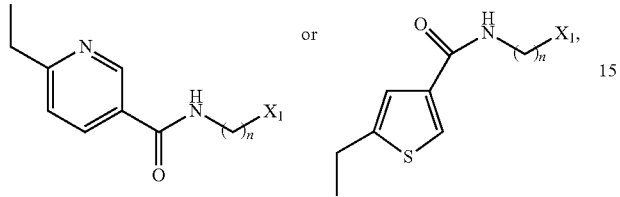

where $X_1$ is described above or comprises $NH_2$, NHBoc, NCS or NPhth.

2. The compound of claim 1, wherein at least one Z of $Y_1$-$Y_4$ is hydrogen.

3. The compound of claim 1, wherein Ar is selected from:

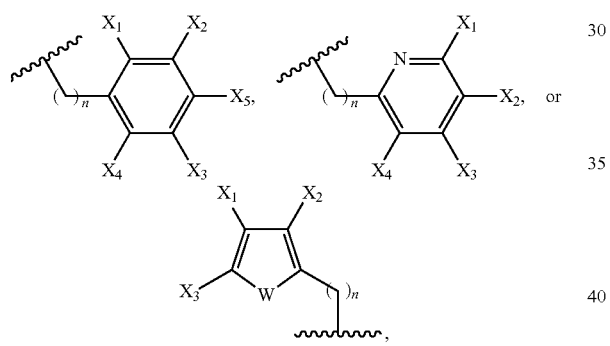

where W is NH, oxygen, or sulfur, n is 0-5, and each of $X_1$-$X_5$ independently is or includes hydrogen, halo, cyano, alkyl, hydroxy, nitro, amino, alkylamino, thiocyano, isothiocyano, alkoxy, aryloxy, carboxyl, carboxyalkyl, carboxyalkyloxy, ester, amido, aldehydo, alkylamido, holoalkylamido, an ester containing group, an carbonyl containing group, an amide containing group, an amine containing group, a thioamide containing group, an alkynyl containing group, or an amino acid-containing group.

4. The compound of claim 1, wherein one of $R_{13}$-$R_{18}$ comprises:

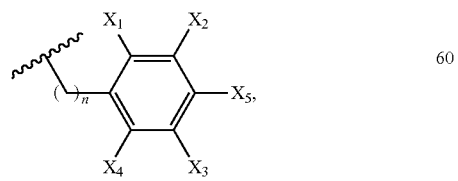

where n is 1-5.

5. The compound of claim 1, wherein $X_5$ comprises $NO_2$.

6. The compound of claim 1, wherein at least three of $Y_1$-$Y_4$ is formula (a-1).

7. The compound of claim 1, wherein an other of $Y_1$-$Y_4$ is formula (a-3) with one of $R_{17-18}$ comprising:

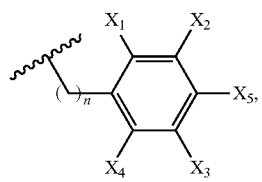

and n is 1-5.

8. The compound of claim 1, wherein Z is selected from:

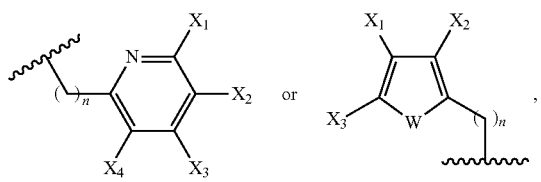

where W is NH, oxygen, or sulfur and n is 1-5.

9. The compound of claim 8, wherein an other of $Y_1$-$Y_4$ is formula (a-3) with one of $R_{17-18}$ comprising:

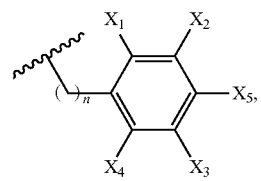

and n is 1-5.

10. A compound of formula (I):

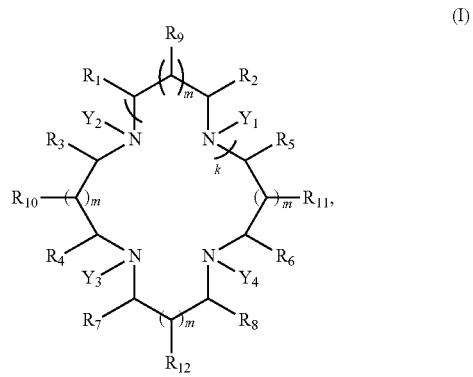

where k is 0 or 1; m is 0 or 1; and each of $Y_1$-$Y_4$ independently is one of a structure of formula (a-1), (a-2), or (a-3):

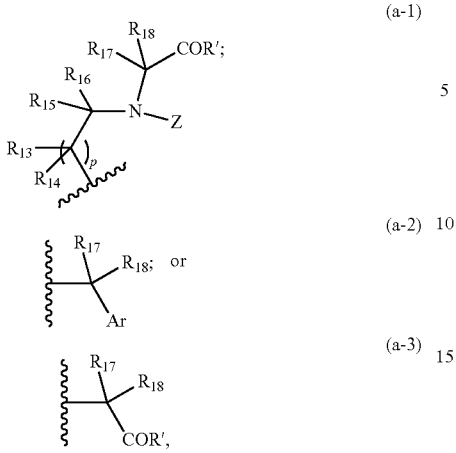

(a-1)

(a-2)

(a-3)

where p is 1 or 2; Z is hydrogen, formula (a-2), formula (a-3), Ar, a pyridylalkyl, a protecting group, an aryl containing group, an alkynyl containing group, an amine containing group, an azide containing group, or an amide containing group; Ar is or includes an aromatic ring or a heteroaromatic ring; and each R' independently is OH, $NH_2$, OR", $NR_2$" wherein each R" is one of alkyl, tert-butyl, allyl, benzyl, benzyloxy, or a protecting group;

wherein each of $R_{1-18}$ independently is or includes hydrogen, carboxyalkyl, alkylamido, alkyl, allyl, benzyl, benzyloxyalkyl, cycloalkyl, alkoxy, hydroxyalkyl, aryl, aryloxy, hydroxyaryl, heteroaryl, phenyl, vinyl, alkynyl, alkenyl, furannylalkyl, alkylthioalkyl, arylhydroxyalkyl, indanyl, inolylalkyl, naphthylalkyl, imidazolylalkyl, pyridiylalkyl, benzothiophenylalkyl, thiophenylalkyl, thioalkyl, thioaryl, thiobenzyl, hydroxy, an alkynyl containing group, substituted carbonyl, hydroxyalkyl, triazolylalkyl, aminoalkyl, benzothiophenylalkyl, carboxyl, carboxyalkyloxy, amine, a protected amine, carboxylic acid, holoalkylamido, aldehyde, ester, amido, tosyl, phthalimidyl, maleimidyl, trityl, tert-butyloxycarbonyl, carbobenzyloxy, o-nosyl, acetyl, fluoroacetyl, dimethoxybenzyl, p-methoxybenzyl, an amide containing group, a thioamide containing group, an amino acid-containing group, an ester containing group, a protecting group, an amine protecting group or:

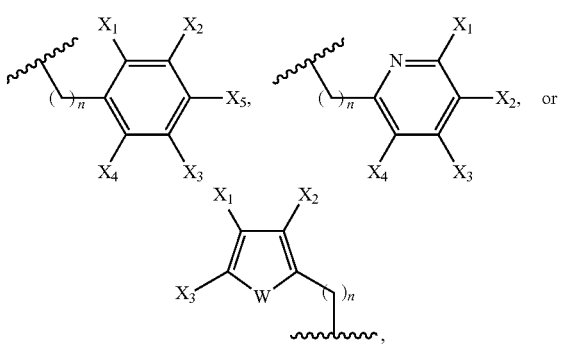

where W is NH, oxygen, or sulfur, n is 1-5, and each of $X_1$-$X_5$ independently is or includes hydrogen, halo, cyano, alkyl, hydroxy, nitro, amino, alkylamino, thiocyano, isothiocyano, alkoxy, aryloxy, carboxyl, carboxyalkyl, carboxyalkyloxy, ester, amido, aldehydo, alkylamido, holoalkylamido, an ester containing group, an carbonyl containing group, an amide containing group, an amine containing group, a thioamide containing group, an alkynyl containing group, or an amino acid-containing group;

wherein more than one of $Y_1$-$Y_4$ is formula (a-1); and wherein at least one Z comprises:

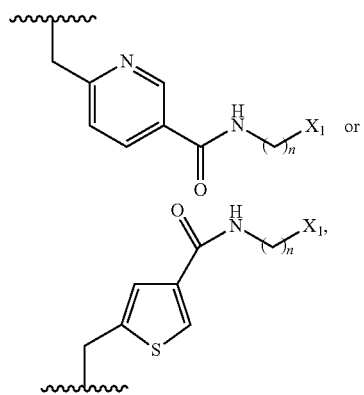

where $X_1$ is described above or comprises $NH_2$, NHBoc, NCS or NPhth.

11. The compound of claim 1, wherein k is 1.

12. A complex comprising the compound of claim 1 and a metal ion, a radioactive isotope of the metal ion, or a radioactive isotope of carbon, nitrogen, iodine, fluorine, oxygen, or helium.

13. The complex of claim 12, wherein the metal ion is selected from the group consisting of Ac, Al, Bi, Pb, Y, Mn, Cr, Fe, Co, Zn, Ni, Tc, Gd, In, Ga, Cu, Re, Sm, Pm, Ho, Zr, Am, Ce, U, a lanthanide, and an actinide.

14. A conjugate comprising the compound of claim 1 and a targeting moiety, a fluorescence moiety, or a nanoparticle.

15. The conjugate according to claim 14, wherein the targeting moiety comprises a biomolecule selected from a hormone, a bile acid, an amino acid, a peptide, a peptidomimetic, a protein, a deoxyribonucleic acid (DNA), a ribonucleic acid (RNA), a lipid, an albumin, a receptor molecule, a receptor binding molecule, a hapten, a monoclonal antibody, a polyclonal antibody, a peptide, an aptamer, a folic acid, an estrogen, or a transferrin.

16. A pharmaceutical composition comprising the compound of claim 1 and a pharmaceutically acceptable carrier.

17. A method of generating a diagnostic image or measurement, the method comprising:
administering to an animal a composition comprising the compound of claim 1; and
imaging or measuring an amount of the composition in a tissue or organ of the animal using magnetic resonance imaging (MRI), fluorescence imaging (FI), x-ray contrast imaging, transmission electron microscopy imaging, a positron emission tomography (PET) imaging, or single photon emission computed spectroscopy (SPECT).

18. The method of claim 17, wherein the composition includes complex comprising $^{90}Y$, $^{86}Y$, $^{111}In$, $^{213}Bi$, $^{212}Bi$, $^{212}Pb$, $^{225}Ac$, $^{177}Lu$, $^{68}Ga$, $^{166}Ho$, $^{153}Sm$, $^{149}Pm$, $^{64}Cu$, $^{89}Zr$, $^{18}F$ or $^{67}Cu$.

19. A method of preparing the compound of claim 1, comprising:
reacting a compound of formula (Ib-1):

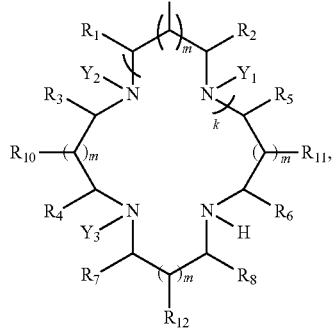
(Ib-1)

wherein: m is 0 or 1; each of $R^{1-12}$ and $Y^{1-3}$ is as defined above, with a compound of formula (Ib-2) or (Ib-3):

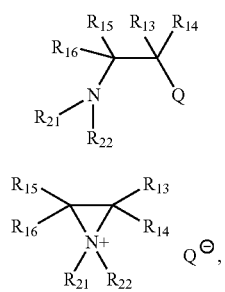
(b-2)

(b-3)

where m is 0 or 1; p is 0 or 1; each of $R^{21-22}$ independently is as defined for $R^{1-20}$; and Q is a counter anion or a leaving group comprising halide, perchlorate, tetrafluoroborate, hexafluoroantimonate, mesylate, triflate, tosylate, carbonate, nitrate, phthalimide, or succinimide.

20. The method of claim 19, further comprising providing a compound of formula (f-1):

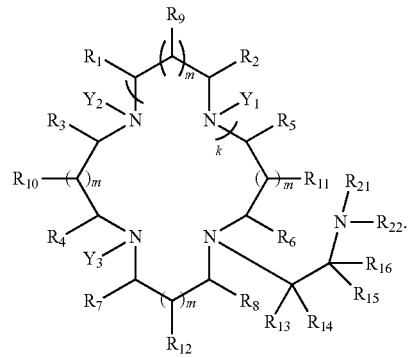
(f-1)

21. The method of claim 20, further comprising: converting (b-2) to (b-3) in the presence of halosequestering agent comprising $AgClO_4$, $AgOTf$, $Ag_2CO_3$, $AgOTs$, $AgNO_3$, $AgSbF_6$, or $AgBF_4$; and reacting (b-3) in situ with (1b-1) to obtain (f-1).

22. The compound of claim 10, wherein one of $R_{15}$-$R_{16}$ comprises:

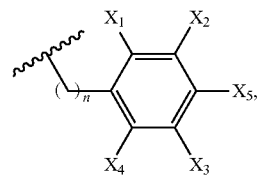

where n is 1-5.

23. The compound of claim 10, wherein k is 1.

24. A complex comprising the compound of claim 10 and a metal ion, a radioactive isotope of the metal ion, or a radioactive isotope of carbon, nitrogen, iodine, fluorine, oxygen, or helium.

25. A conjugate comprising the compound of claim 10 and a targeting moiety, a fluorescence moiety, or a nanoparticle.

* * * * *